United States Patent
Barry et al.

(10) Patent No.: US 8,952,221 B2
(45) Date of Patent: *Feb. 10, 2015

(54) ENZYMES THAT SYNTHESIZE ZINGIBERENE

(75) Inventors: Cornelius Barry, Haslett, MI (US); Eliana Gonzales-Vigil, Vancouver (CA)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/130,890

(22) PCT Filed: Sep. 21, 2011

(86) PCT No.: PCT/US2011/052607
§ 371 (c)(1),
(2), (4) Date: Apr. 11, 2014

(87) PCT Pub. No.: WO2013/006190
PCT Pub. Date: Jan. 10, 2013

(65) Prior Publication Data
US 2014/0230101 A1    Aug. 14, 2014

Related U.S. Application Data

(60) Provisional application No. 61/505,004, filed on Jul. 6, 2011.

(51) Int. Cl.
| | | |
|---|---|---|
| C07H 21/04 | (2006.01) | |
| C12N 5/04 | (2006.01) | |
| C12N 5/10 | (2006.01) | |
| C12N 1/20 | (2006.01) | |
| A01H 9/00 | (2006.01) | |
| A01H 11/00 | (2006.01) | |
| C12N 9/88 | (2006.01) | |
| C12P 5/00 | (2006.01) | |

(52) U.S. Cl.
CPC ............ *C12N 9/88* (2013.01); *C12Y 402/03012* (2013.01); *C12P 5/00* (2013.01); *C12P 5/007* (2013.01)
USPC ........ 800/295; 536/23.6; 435/252.3; 435/419

(58) Field of Classification Search
USPC ................................................ 800/302, 295
See application file for complete search history.

(56) References Cited

U.S. PATENT DOCUMENTS

2010/0138954 A1* 6/2010 Sallaud et al. ................ 800/278
2013/0263329 A1 10/2013 Barry et al.

FOREIGN PATENT DOCUMENTS

WO    WO-2012165961        12/2012
WO    WO-2013006190 A1     1/2013

OTHER PUBLICATIONS

"International Application Serial No. PCT/US2011/052607, International Preliminary Report on Patentability mailed Jan. 16, 2014", 6 pgs.
Meinkoth, J., et al., "Hybridization of Nucleic Acids Immobilized on Solid Supports", *Analytical Biochemistry*, 138(2), (1984), 267-284.
Sallaud, C., et al., "A Novel Pathway for Sesquiterpene Biosynthesis from Z,Z-Farnesyl Pyrophosphate in the Wild Tomato *Solanum habrochaites*", *The Plant Cell*, 21(1), (2009), 301-317.
Schilmiller, A. L., et al., "Monoterpenes in the glandular trichomes of tomato are synthesized from a neryl diphospate precursor rather than geranyl diphosphate", *Proc. Natl. Acad. Sci. USA*, 106(26), (2009), 10865-10870.
Trapp, S. C., et al., "Genomic Organization of Plant Terpene Synthases and Molecular Evolutionary Implications", *Genetics* 158(2), (2001), 811-832.
"Echelon", Available on the internet: http://www.echelon-inc.com/content/EBI/product/files/2076_I-0170%20ZZ-FPP%20TDS%20rev%201.pdf, 1 pg, Mar. 26, 2009.
"International Application Serial No. PCT/US2011/52607, Search Report mailed Jan. 20, 2012", 4 pgs.
"International Application Serial No. PCT/US2011/52607, Written Opinion mailed Jan. 20, 2012", 4 pgs.
"Swiss-Prot: B8XA41.1", Available at <http://www.ncbi.nlm.nih.gov/protein/B8XA41.1>, (Sep. 21, 2011).
"U.S. Appl. No. 13/787,029, Supplemental Preliminary Amendment filed Apr. 9, 2014", 4 pgs.
"Evolution of a Complex Locus for Terpene Biosynthesis in Solanum", The Plant Cell, vol. 25: 2022-2036, Jun. 2013, www.plantcell.org ã 2013 American Society of Plant Biologists. All rights reserved., (Jun. 1, 2013), 228 pgs.

* cited by examiner

*Primary Examiner* — Ashwin Mehta
*Assistant Examiner* — Rebecca Coobs
(74) *Attorney, Agent, or Firm* — Schwegman Lundberg & Woessner, P.A.

(57) ABSTRACT

The invention relates to nucleic acids encoding a zingiberene synthase that enables host cells and plants to make zingiberene that is useful in fragrances and for repelling or killing insects. The invention also relates to isolated zingiberene synthases and to methods for making zingiberenes.

10 Claims, 15 Drawing Sheets

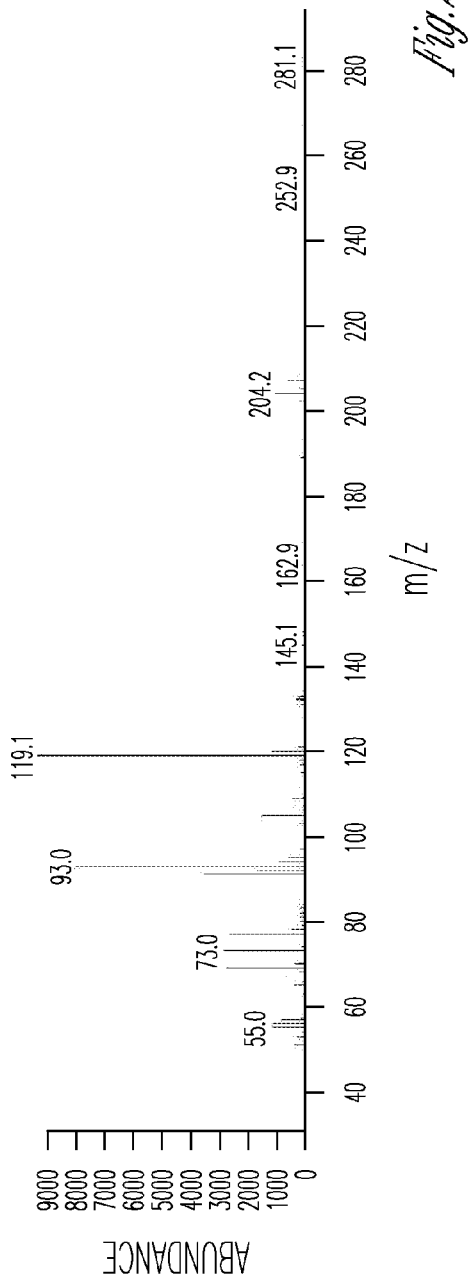
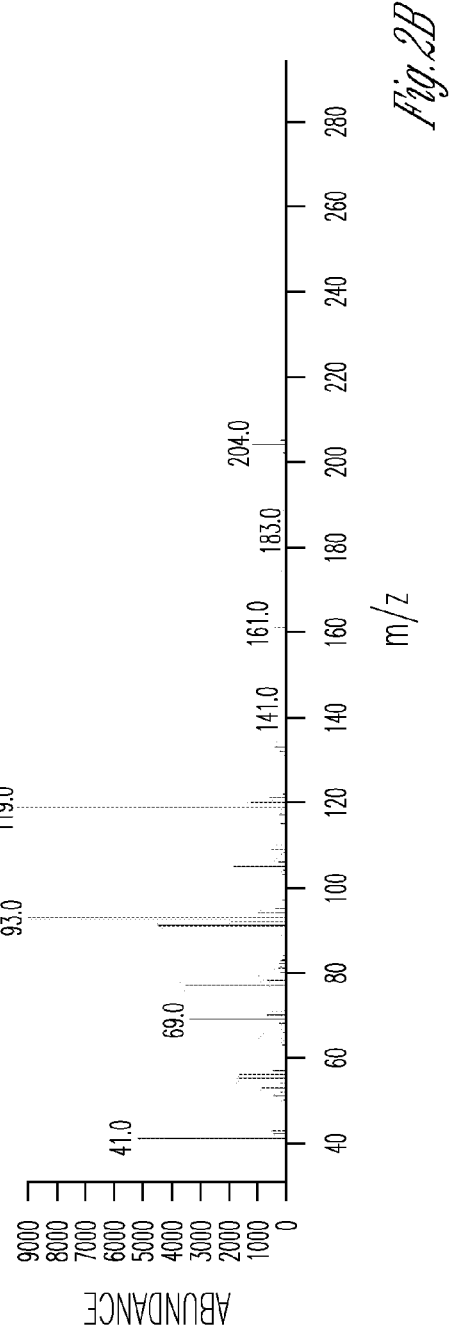

ATGGATAGTTGGCTATAGAGAAGCACAATCATAACCCTTTCTCATCCTAAGCTAGGCAATGGGAAAACAATTCATCC
AATGCAATTTTCCGGAGATCATGTAGAGTAAGATGCAGCCACAGTACCCCTTCATCAATGAATGGTTCGAAGAT
GCAAGGGATAGAATAAGGGAAAGTTTGGGAAAGTAGAGTTATCTCCTTCTCCTATGACACAGGATGGGTAGCT
ATGGTCCCTCAAAACATTCACTAAATGAGCCATGTTTTCCACAATGTTTGGATTATTGAAAATCAAAGAG
AAGATGGATCTTGGGGACTAAACCCTAGCCATCCATTGCTTCTTAAGGACTCACTTCTTCCACTCTTGCATGTT
GCTTGCACTAACCAAATGGAGAGTGGAGATGGACAAATGAAAGAGGCCTTGGCTTTATTGAAACCGAGAGTT
GGGCAATTGATAACAAGGATCAAATTTCACCTCTAGGATTTGAAATTATATTCCCAGTATGATCAAGTCTCCACA
AAAACTAAACTTAAATCTAGCAATTAACAAAAGAGATTCAACAATTAAAAGAGCATTACAGAATGAGTTCACGAGG
AATATTGAATATATGAGTGAAGGATTGGTGAATTATGTGATTGGAAGGAAATAATAAGTTACATCAAAGGCAAA
ATGGTTCATTATTTGATTCACGAGCCACTACTGCAGCTGCCTTGATTACCATCAGCATGATCAGAAAATGCTATGA
ATATCTTAATTCAATCTTGCAACAACACAAAAATTGGGTTCCCACTATGTATCCAACAAAGATACATTCATTGCTTT
GCTTGGTTGATACACTTCAAATCTCAAAAATCTTGGAGTACATCGGCATTTTCTCAAATGTCACCCATTGTGCTATGGCTTTCGACTTCTA
ATACAGCCTATGCCAACAAAGAATGAAGAAATTTCTCAGACAGAATTTGTGAAGAACATTTCTTTGCAACAAGT
AGGATAAGCTACTATGATGTCTCTCAGATGAACTAGCCCTTATAGGTCACCTAACATTAACAATAAGGACT
GGGAAATATACAAGTCATGTTGAAACTCTTGATCATGAGCATCACCAATTGGCTATTGATCATGAGAAAGATG
ACATTGGATAAGAGATTAACAATTGGACAAGAACAATCTTAAACAATGGCTTAAACAATGGCCTTCATAGATAG
GATGTCAAAAAGGAGTGGAACTTGCTTGAGGAACTTGGTCTTTGAAAATCTGATCTAGCAGAAATAGAAGATAT
ATAAGTCATACGAAGAGAACAATTTTAAAATCTAAAAGCAGCTATAGGTCACCTAACATTAAGGACT
TGTTTATATTTTCAATACAGCAGAGTTTGAATTATGCCAAAGCTTGGAACAACAATTTATATCTGCTAGTTACTATGTGCTATTCCT
GTTTGAAGATTGTAGATTGGAACCAACTGGATTATCCGATGCTGTCGTTCTCGTCGGAACTTCAACAACTCAAGAGGTG
ATTGTCCCGGGCCTGAATTTATACGGACTTGGAGTTTTGCATCTACAGATGAATCTCAACATCATGAATTAGTAGAAAGGTGGGATGACTATG
GATCATTTCGAGAGTTTTGCATCTACAGATGAATCTCAACATCATGAATTAGTAGAAAGGTGGGATGACTATG
CAAGTGTAGGTTATAAATCTGAGAGGGTCTAAAGTTTATTTTACAAATCAACATTATTATTCACCTTATTAATTGTGCCTAAAGTGATGAAGTTGATG
AATTGCTGAAATTAACAAGGATGGACAGTAGAGTCGTGTCTGCCAAGCAACAATATTACCAAAGAAGAGTATTTGATCTTAGTCTATA
TTGATGAACGAGTAGAGTTACGGTGTTCTGTCCACACAACAACATATTTATTGGAGCCTCCCTGAGAAATAGAAGAGAGAGTATTTAGAAG
ACATTTGTCAGATTGATTCCTCTCAACAACAATATTTATTGGAGCCTCCCTGAGGCTTTGAAAATATCCAAAGATCTTTAGAAAG
TGATGAAATTTATGGTTTATCCAATTTACCGGTATAGTCTTGAGCCTCCCAATGATGAAAATGTTACAAGATTCCAAGAGA
GAACAAAAGGAGGGCTCAATAAATTAGTCACATTACTAATGAGAAGAATCTGGAGGAAGAAGCTATAATGAAG
ATGAAGGAAATCTTGGAAATGAAAAGAAAAGAAGTTATTTAAAATGGTTTTCAAAAAAAGGGAAGCCAATTGC
CTCAATTATGCAAAGAAAATATTTTGGAGGACATGCAAATGGGCTCATTTCACTTATTCACAACCACTCAATCATTAA

ATTTCCAGGAGGAAATGGAGAATCACATTGATGAAGTCTTTTACAAACCACTACTGAAGAAGTCTTTTACAAACCACTACTGAATCATGATGAAGTCTTTTACAAACCACTGAAGTCTTTTACAAACCACTACTTAA

*Fig. 3A*

MIVGYRSTITLSHPKLGNGKTISSNAIFRRSCRVRCSHSTPSSMNGFEDARDRIRESFGKVELSPSSYDTAWWAMVPS
KHSLNEPCFPQCLDWIIENQREDGSWGLNPSHPLLLKDSLSSTLACLLALTKWRVGDEQIKRGLGFIETQSWAIDNKD
QISPLGFEIFPSMIKSAEKLNLNLAINKRDSTIKRALQNEFTRNIEYMSEGFGELCDWKEIIKLHQRQNGSLFDSPATTA
AALIYHQHDKKCYEYLNSILQQHKNWVPTMYPTKIHSLLCLVDTLQNLGVHRHFKSEIKKALDEIYRLWQQKNEEIFSN
VTHCAMAFRLLRISYYDVSSDELAEFVDEEHFFATSGKYTSHVEILELHKASQLAIDHEKDDILDKINNWTRTFMEQKLL
NNGFIDRMSKKEVELALRNFYIISDLAENRRYIKSYEENNFKILKAAYRSPNINNKDLFIFSIRDFELCQAQHQEELQQLK
RWFEDCRLDQLGLSEQFISASYLCAIPIVPGPELSDARLVYAKYVMLLTIVDDHFESFASTDECLNIIELVERWDDYASV
GYKSERVKVLFSMFYKSIEEIATIAEIKQGRSVKNHLINLWLKVMKLMLMERVEWCSGKTIPRIEEYLYVSSITFGSRLIP
LTTQYFIGIKISKDLLESDEIYGLCNFTGIVLRLLNDLQDSKREQKEGSINLVTLLMKSISEEAIMKKEILEMKRRELFK
MVLVQKKGSQLPQLCKEIFWRTCKWAHFTYSQTDRYRFPEEMENHIDEVFYKPLNH

MNGFEDARDRIRESFGKVELSPSSYDTAWVAMVPSKHSLNEPCFPQCLDWIENQREDGSWGLNPSHPLLLKDSLSS
TLACLLALTKWRVGDEQIKRGLGFIETQSVVAIDNKDQISPLGFEIIFPSMIKSAEKLNLNLAINKRDSTIKRALQNEFTRNI
EYMSEGFGELCDWKEIIKLHQRQNGSLFDSPATTAAALIYHQHDKKCYEYLNSILQQHKNIWVPTMYPTKIHSLLCLVD
TLQNLGVHRHFKSEIKKALDEIYRLWQQKNEEIFSNVTHCAMAFRLLRISYDVSSDELAEFVDEEHFFATSGKYTSHV
EILELHKASQLAIDHEKDDILDKINNWTRTFMEQKLLNNGFIDRMSKKEVELALRNFYIISDLAENRRYIKSYEENNFKILK
AAYRSPNINNKDLFIFSIRDFELCQAQHQEELQQLKRWFEDCRLDQLGLSEQFISASYLCAIPIVGPELSDARLVYAKY
VMLLTIVDDHFESFASTDECLNIIELVERWDDYASVGYKSERVKVLFSMFYKSIEEIATAEIKQGRSVKNHLINLWLKVM
KLMLMERVEWCSGKTIPRIEEYLYVSSITFGSRLIPLTTQYFIGIKISKDLLESDEIYGLCNFTGIVLRLLNDLQDSKREQK
EGSINLVTLLMKSISEEEAIMKEILEMKRRELFKMVLVQKKGSQLPQLCKEIFWRTCKWAHFTYSQTDRYRFPEEM
ENHIDEVFYKPLNH

*Fig. 4B*

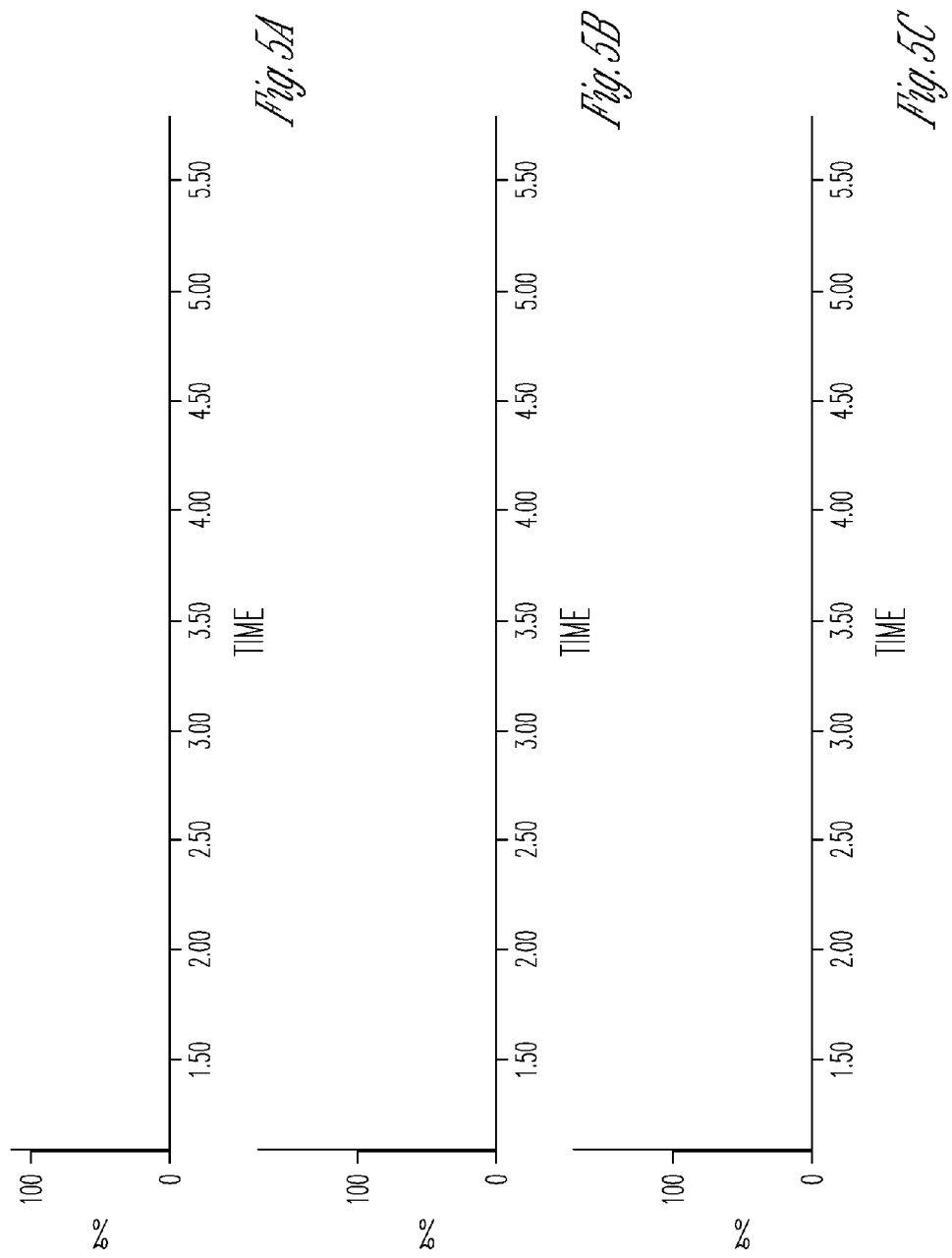

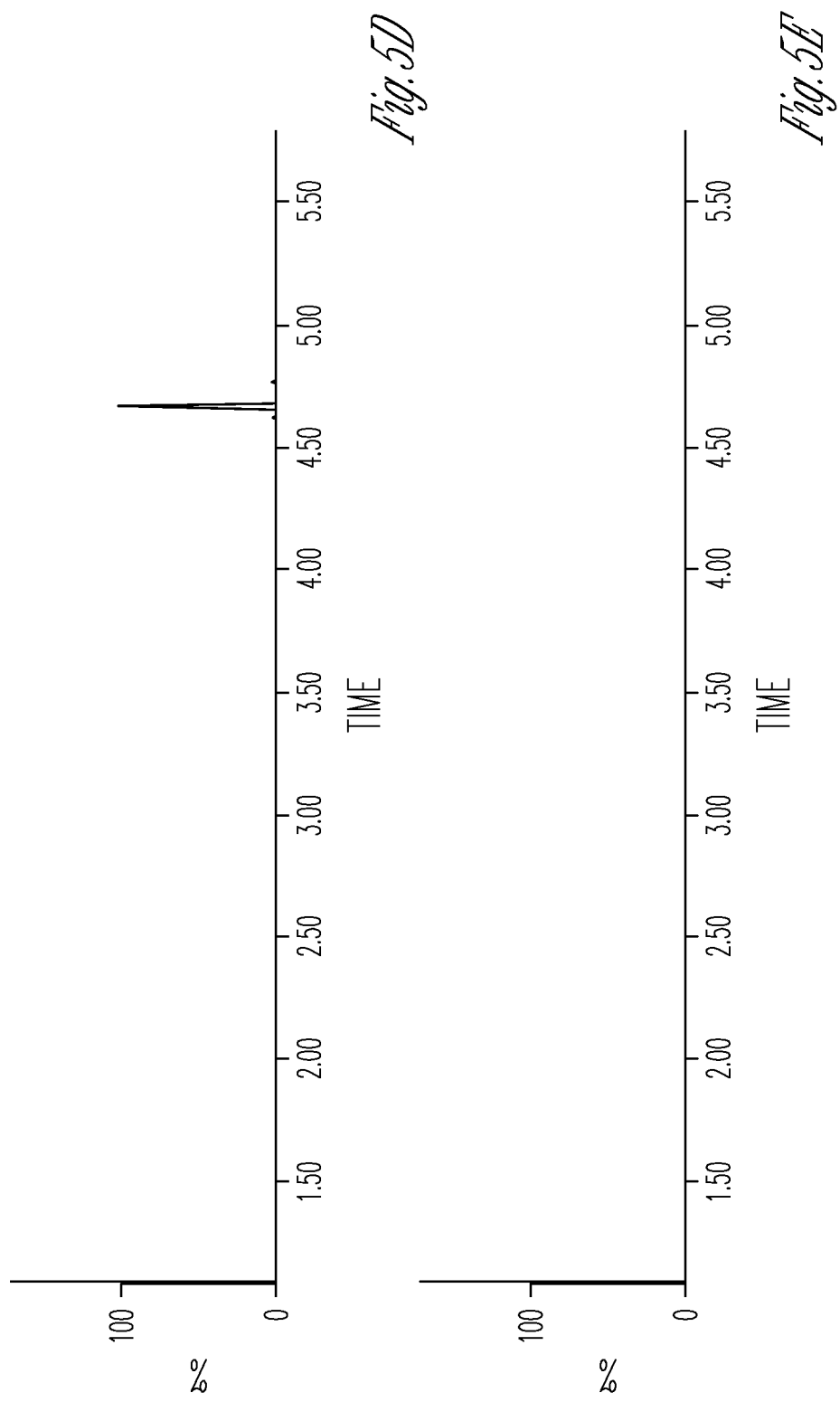

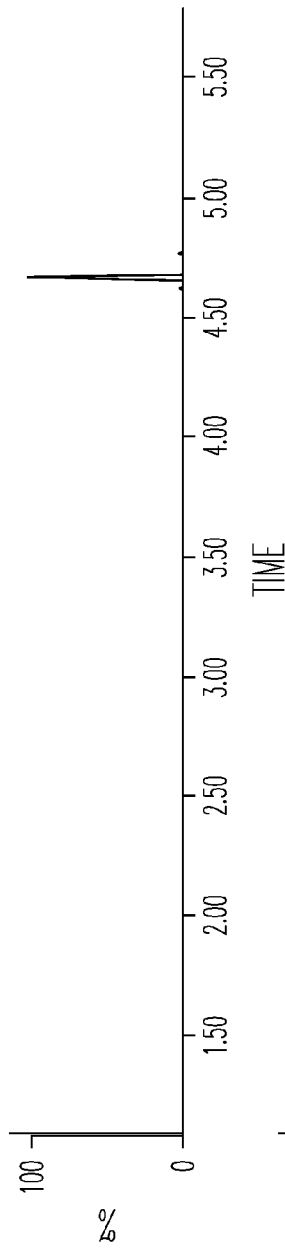
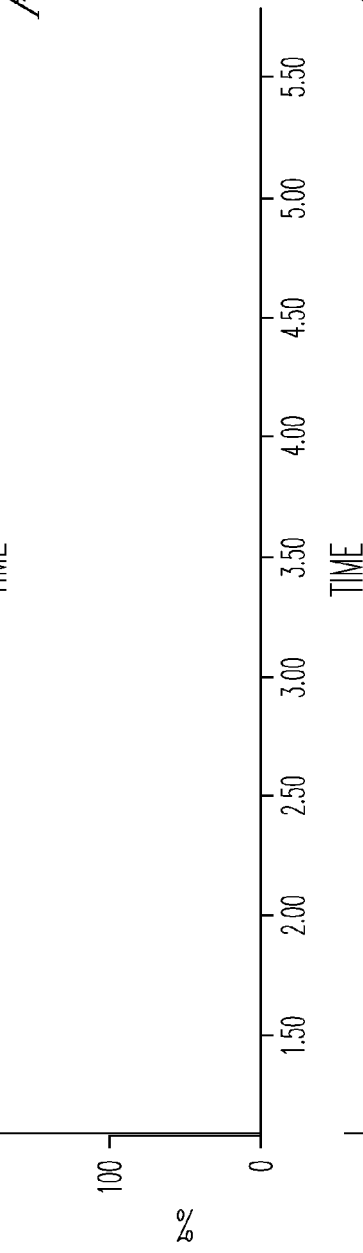
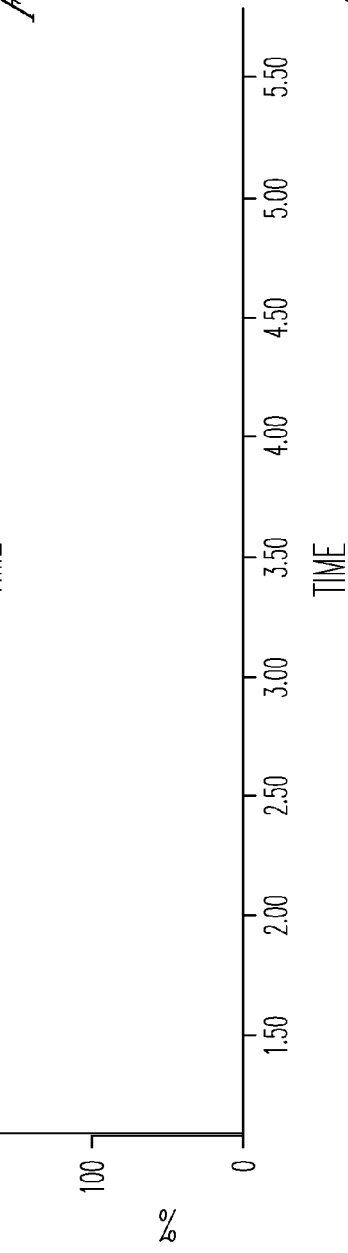
Fig. 6A
Fig. 6B
Fig. 6C

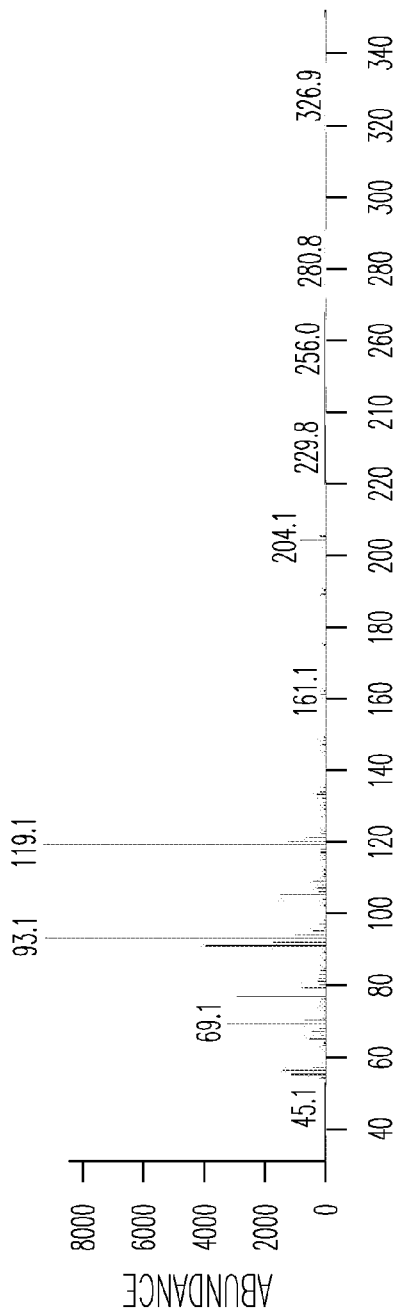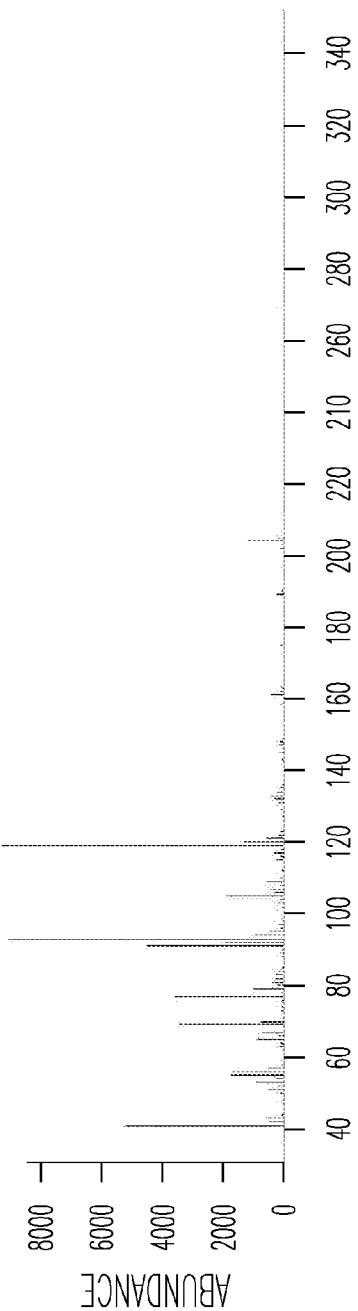
Fig. 8A
Fig. 8B

|      | PHS1 | SBS  | ZIS |
|------|------|------|-----|
| PHS1 |      | 87   | 96  |
| SBS  | 89%  |      | 67  |
| ZIS  | 88%  | 91%  |     |

ENZYMES THAT SYNTHESIZE ZINGIBERENE

This application is a U.S. National Stage Application under 35 U.S.C. §371 of PCT/US2011/052607 filed on Sep. 21, 2011, and published on Jan. 10, 2013 as WO 2013/006190, which claims benefit of the priority filing date of U.S. patent application Ser. No. 13/787,029, filed on Mar. 6, 2013 and U.S. Patent Application Ser. No. 61/505,004, filed Jul. 6, 2011, the contents of which are specifically incorporated herein by reference in their entirety.

BACKGROUND OF THE INVENTION

Common approaches for the control of crop-destroying insects involve chemical treatments with pesticides and insecticides. However, public concern over the toxicity of pesticides and insecticides and/or the use of industrial processes that generate these pesticides/insecticides, as well as their environmentally incompatible side products, raise concerns about the sustainability of these approaches.

Therefore, researchers continue to search for products and processes that will enable humans to effectively control insects or modify their behavior without negative effects.

SUMMARY OF THE INVENTION

The invention relates to the identification and isolation of new *Solanum habrochaites* nucleic acids encoding zingiberene synthases. The zingiberene made by the synthases described are useful in fragrances, insect repellents and insecticide compositions. Zingiberene can act as a natural insect repellant to protect cultivated crops, for example, from whiteflies and thrips. As described herein, plants can be generated to synthesize zingiberene and thereby acquire resistance to insect-mediated damage. Zingiberene can also be efficiently manufactured recombinantly or in vitro, thereby providing a source of zingiberene for incorporation into fragrances, insect repellent and/or insecticidal compositions. Such compositions can be used on crops, parks, trees, lawns, structures, and mammals.

One aspect of the invention is an isolated nucleic acid encoding a zingiberene synthase. For example, the nucleic acids can encode any zingiberene synthase with an amino acid sequence selected from the group consisting of SEQ ID NOs: 2, 4, 6, 8, 11, 12, 14, 16, 18, an amino acid sequence with at least 90% sequence identity to any of SEQ ID NOs: 2, 4, 6, 8, 11, 12, 14, 16, 18, and any combination thereof. The synthase nucleic acids can, for example, have any of nucleotide sequence SEQ ID NOs: 1, 3, 5, 7, 13, 15, 17, 19, or any nucleotide sequence with at least 80% sequence identity to any of SEQ ID NOs: 1, 3, 5, 7, 13, 15, 17, 19, or a combination thereof. The percent sequence identity of related synthase nucleotide and amino acid sequences can also be lower or higher, as explained below.

Another aspect of the invention is an expression cassette that includes any of the zingiberene synthase nucleic acids described herein, where the nucleic acid is operably linked to a promoter functional in a host cell. For example, the expression cassette can include a zingiberene synthase nucleotide sequence selected from the group consisting of SEQ ID NOs: 1, 3, 5, 7, 13, 15, 17, 19, or a nucleotide sequence with at least 80% sequence identity to any of SEQ ID NOs: 1, 3, 5, 7, 13, 15, 17, 19, or a combination thereof. The percent sequence identity of related synthase nucleotide and amino acid sequences can also be lower or higher, as explained below. The zingiberene synthase nucleic acids and/or expression cassettes can be present in a host cell, for example, in a recombinant host cell or in a genetically modified host cell. In some embodiments, the host cell is a plant cell. In other embodiments, the host cell is a microorganism.

A further aspect of the invention is a plant tissue that includes an expression cassette or a nucleic acid described herein.

Another aspect of the invention is a plant that includes an expression cassette or a nucleic acid described herein.

A further aspect of the invention is a method of making zingiberene that includes:
 a) culturing the host cell that includes one of the nucleic acids or expression cassettes, or expression vectors described herein under conditions sufficient for expression of the encoded zingiberene synthase; and
 b) providing the host cell with a substrate for the zingiberene synthase to thereby make the zingiberene.

For example, the substrate can be 2Z,6Z-farnesyl diphosphate. As described herein, the host cell can, for example, be a bacterial or yeast cell. In some embodiments, the microorganism is *E. coli*.

Another aspect of the invention is an isolated zingiberene synthase. Such an isolated terpene synthase can have any amino acid sequence selected from the group SEQ ID NOs: 2, 4, 6, 8, 11, 12, 14, 16, 18, an amino acid sequence with at least 90% sequence identity to any of SEQ ID NOs: 2, 4, 6, 8, 11, 12, 14, 16, 18, or a combination thereof. The percent sequence identity of related synthase nucleotide and amino acid sequences can also be lower or higher, as explained below.

Another aspect of the invention is a method of manufacturing zingiberene comprising contacting an isolated zingiberene synthase having any amino acid sequence selected from the group SEQ ID NOs: 2, 4, 6, 8, 11, 12, 14, 16, 18, an amino acid sequence with at least 90% sequence identity to any of SEQ ID NOs: 2, 4, 6, 8, 11, 12, 14, 16, 18, or a combination thereof, with a substrate for the zingiberene synthase to thereby manufacture the terpene. For example, the substrate can be 2Z,6Z-farnesyl diphosphate. The percent sequence identity of related synthase nucleotide and amino acid sequences can also be lower or higher, as explained below.

Other aspects and embodiments of the invention are described throughout this application.

DESCRIPTION OF THE FIGURES

FIGS. 2A and 2B show ion fragmentation patterns of the peak eluting at 10 minutes from LA2167 (FIG. 2A) as compared with the ion fragmentation pattern of a control zingiberene (FIG. 2B).

FIGS. 3A and 3B show the nucleotide sequence of LA2167-ZIS open-reading frame (FIG. 3A, SEQ ID NO:5) and the amino acid sequence of the LA2167-ZIS enzyme (FIG. 3B, SEQ ID NO:6). Bold designation denotes the start and stop codons, respectively.

FIGS. 4A and 4B show the nucleotide (FIG. 4A, SEQ ID NO:7) and the amino acid (FIG. 4B, SEQ ID NO:8) sequences, respectively, of a codon optimized synthetic version of LA2167-ZIS that lacks a chloroplast transit sequence. Bold designations denote the start and stop codons.

FIG. 5A-5E show GC-MS profiles (extracted ion 93) of products synthesized by *E. coli* cultures that express the recombinant LA2167-ZIS zingiberene synthase after incubation with the following isoprenoid diphosphate substrates: no substrate (FIG. 5A), geranyl diphosphate (GPP; FIG. 5B), neryl diphosphate (NPP, FIG. 5C), (2Z,6Z)-farnesyl diphosphate (2Z,6Z-FPP, FIG. 5D) and (E,E)-α-farnesyl diphosphate (E,E-FPP, FIG. 5E). As illustrated, the zingiberene peak at about 4.65 is only observed when 2Z,6Z-farnesyl diphosphate is used as substrate (FIG. 5D).

FIG. 6A-C show GC-MS profiles (extracted ion 93) of products synthesized by E. coli cultures expressing: the recombinant LA2167-ZIS zingiberene synthase+2Z,6Z-FPP as a substrate (FIG. 6A), empty-vector+2Z,6Z-FPP (FIG. 6B) and 2Z,6Z-FPP alone (FIG. 6C). As illustrated, the zingiberene peak at about 4.65 is only observed when the recombinant zingiberene synthase LA2167-ZIS is expressed and when the substrate 2Z,6Z)-farnesyl diphosphate is present (FIG. 6A).

FIG. 8A-8B shows the ion fragmentation pattern of zingiberene produced by recombinantly expressed LA2167-ZIS (FIG. 8A) compared with that of the fragmentation pattern for zingiberene obtained from a library of reference compounds (FIG. 8B). Note that fragment ions 45 to 350 were collected in the experimental sample, hence the absence of the ion fragment at mass 41.0 in FIG. 8A.

FIG. 9A-9C shows a sequence alignment and percent sequence identity of terpene synthases from different tomato species. FIGS. 9A and 9B show an amino acid alignment of phellandrene synthase (PHS1) (Schilmiller et al., Proc Natl Acad Sci USA 106, 10865-10870 (2009); SEQ ID NOs: 9, 20), santalene and bergamotene synthase (SBS) (Sallaud et al., Plant Cell 21, 301-317 (2009); SEQ ID NOs: 10, 21), and zingiberene synthase (ZIS; SEQ ID NOs:2, 22). Shaded regions indicate conserved amino acids. FIG. 9C shows the percent amino acid identity between PHS1, SBS and ZIS (⊐⊐ symbols) and the number of amino acids that differ across the protein sequence length between PHS1, SBS and ZIS (xx symbols). Thus, PHS1 and SBS are 89% identical in their amino acid sequences but have 87 different amino acids. PHS1 and ZIS are 88% identical in their amino acid sequences but have 96 different amino acids, while SBS and ZIS are 91% identical in their amino acid sequences but have 67 different amino acids These amino acid differences can be responsible for the different enzyme activities of each protein.

DETAILED DESCRIPTION OF THE INVENTION

Figure 1A:
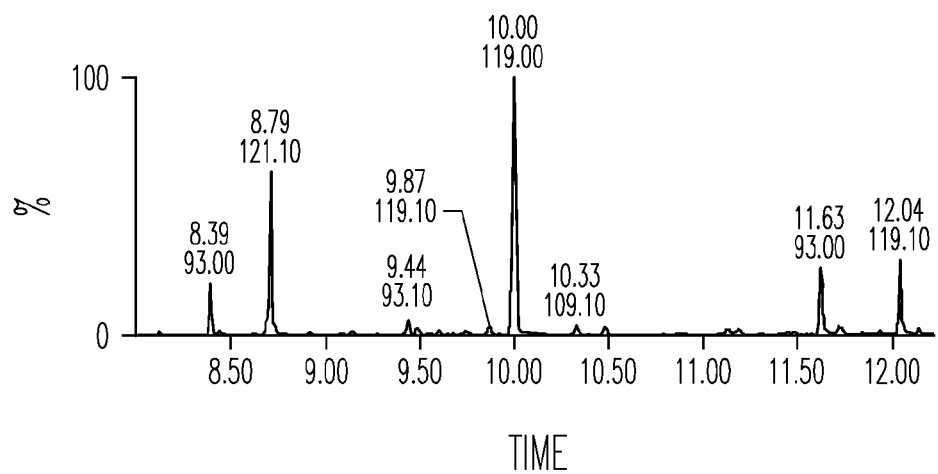
FIGS. 1A and 1B show gas chromatography-mass spectroscopy (GC-MS) profiles (extracted ion 93) of leaf dip extracts of *Solanum habrochaites* accession LA2167. The major peak eluting at 10 minutes corresponds to zingiberene. Data from two separate leaf extracts are presented FIGS. 1A and 1B).

Zingiberene is a fragrant sesquiterpene that exhibits potent insect repellent and insecticidal activities. As described herein, the inventors have isolated nucleic acids that encode such zingiberene synthases from various accessions of the wild tomato species, Solanum habrochaites. Although zingiberene is generated by different plant species including ginger, turmeric, and cultivated tomatoes, the ratio of zingiberene synthesized in the trichomes of certain accessions of the wild tomato species Solanum habrochaites relative to other sesquiterpenes is particularly high. As described herein, the inventors have screened numerous accessions of Solanum habrochaites and have isolated and characterized new sesquiterpene synthase genes, which provide plants with the ability to synthesize zingiberene.

The fragrant, insecticidal and insect repellent compounds made by these zingiberene synthases are terpenoids. Terpenoids are the largest, most diverse type of product made by plants. For example, there are an estimated 15,000 or more terpenoids made by plants. Terpenoids can be cyclic or acyclic compounds. While some terpenoids are key components of the plants' machinery (e.g., the phytol side chains of chlorophyll, various carotenoid pigments and the like), many terpenoids are classified as secondary metabolites that are not directly involved in plant growth and development. These secondary metabolites are thought to have a role in the interaction of the plant with the environment, for example, in plant communication or defense (Harborne, Recent advances in the ecological chemistry of plant terpenoids, pp. 396-426 in ECOLOGICAL CHEMISTRY AND BIO CHEMISTRY OF PLANT TERPENOIDS, Clarendon Press, Oxford (1991)).

The zingiberene synthases are encoded by a superfamily of terpene synthase genes (see, e.g., Trapp & Croteau, Genomic Organization of Plant Terpene Synthases and Molecular Evolutionary Implications, GENETICS 158: 811-32 (2001)). While there are some structural similarities between terpene synthases, the genomic organization, as well as the sequences of terpene synthases can vary significantly from one species, or plant accession, to the next. Moreover, a single plant species can have a multitude of different terpene synthases because different terpene synthases have different activities, operate on different substrates, are localized in different parts of the plant cell and synthesize different types of terpenoids.

The sesquiterpenes are the most diverse group of isoprenoids. They perform a variety of functions in plants. For example, some sesquiterpenes function as pheromones and juvenile hormones in plants while others act as insect repellents. Sesquiterpenes can be acyclic, monocyclic, bicyclic, tricyclic or tetracyclic compounds. Sesquiterpenes are 15 carbon compounds that are formed from three isoprenoid units. Intermediates that may be used for formation of some sesquiterpenes include isopentenyl diphosphate (IPP), dimethylallyl diphosphate (DMAPP) and (E,E)-α-farnesyl diphosphate (FPP).

IPP and DMAPP can be the precursors of isoprene, monoterpenoids (with 10 carbons), sesquiterpenes (with 15 carbons), diterpenoids (with 20 carbons), carotenoids (with 40 carbons), chlorophylls and plastoquinone-9 (with 45 carbons). In fact, terpene synthases are often highly promiscuous both in terms of the substrates that they utilize and the products that they produce. A terpene synthase enzyme that predominantly synthesizes one type of terpene is unusual.

Zingiberene Synthases

Zingiberene synthases make zingiberene, a sesquiterpene that exhibits potent insect repellent and insecticidal activities. Although zingiberene is generated by different plant species including ginger, turmeric, and cultivated tomatoes, the ratio of zingiberene synthesized in the trichomes of certain accessions of the wild tomato species Solanum habrochaites relative to other sesquiterpenes is particularly high. As described herein, the inventors have screened many different accessions of the wild tomato species Solanum habrochaites and have identified particular Solanum habrochaites accessions that synthesize zingiberene.

Different isomers of zingiberene exist and zingiberene can spontaneously convert to curcumene. As used herein, the term "zingiberene" refers to zingiberene, 7-epi-zingiberene, curcumene and/or alpha-zingiberene. The LA2167-ZIS synthase described herein can synthesize any one or any combination of these compounds. The structures of 7-epi-zingiberene, zingiberene and curcumene are shown below.

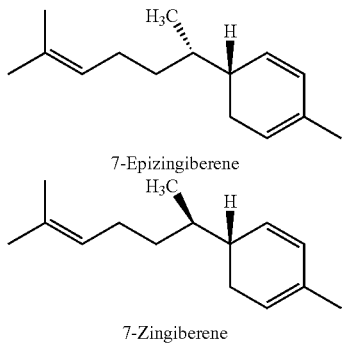

7-Epizingiberene

7-Zingiberene

The structures of S-curcumene and R-curcumene are shown below.

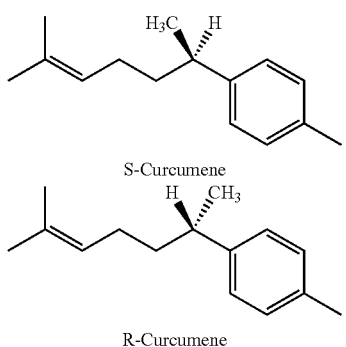

S-Curcumene

R-Curcumene

Zingiberene is made via reaction mediated by a zingiberene synthase using 2Z, 6Z-farnesyl diphosphate as a substrate.

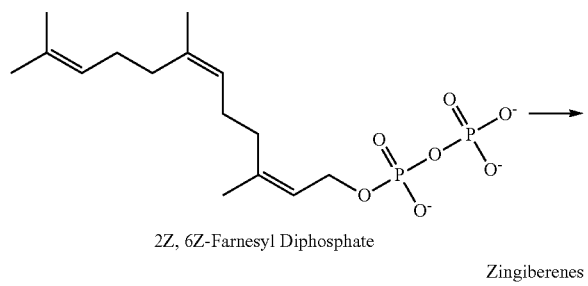

2Z, 6Z-Farnesyl Diphosphate

Zingiberenes

The zingiberene synthases typically do not make zingiberene using neryl diphosphate (NPP) as a substrate. This is illustrated by results obtained with the LA2167-ZIS zingiberene synthase (FIG. 5).

Figure 10:
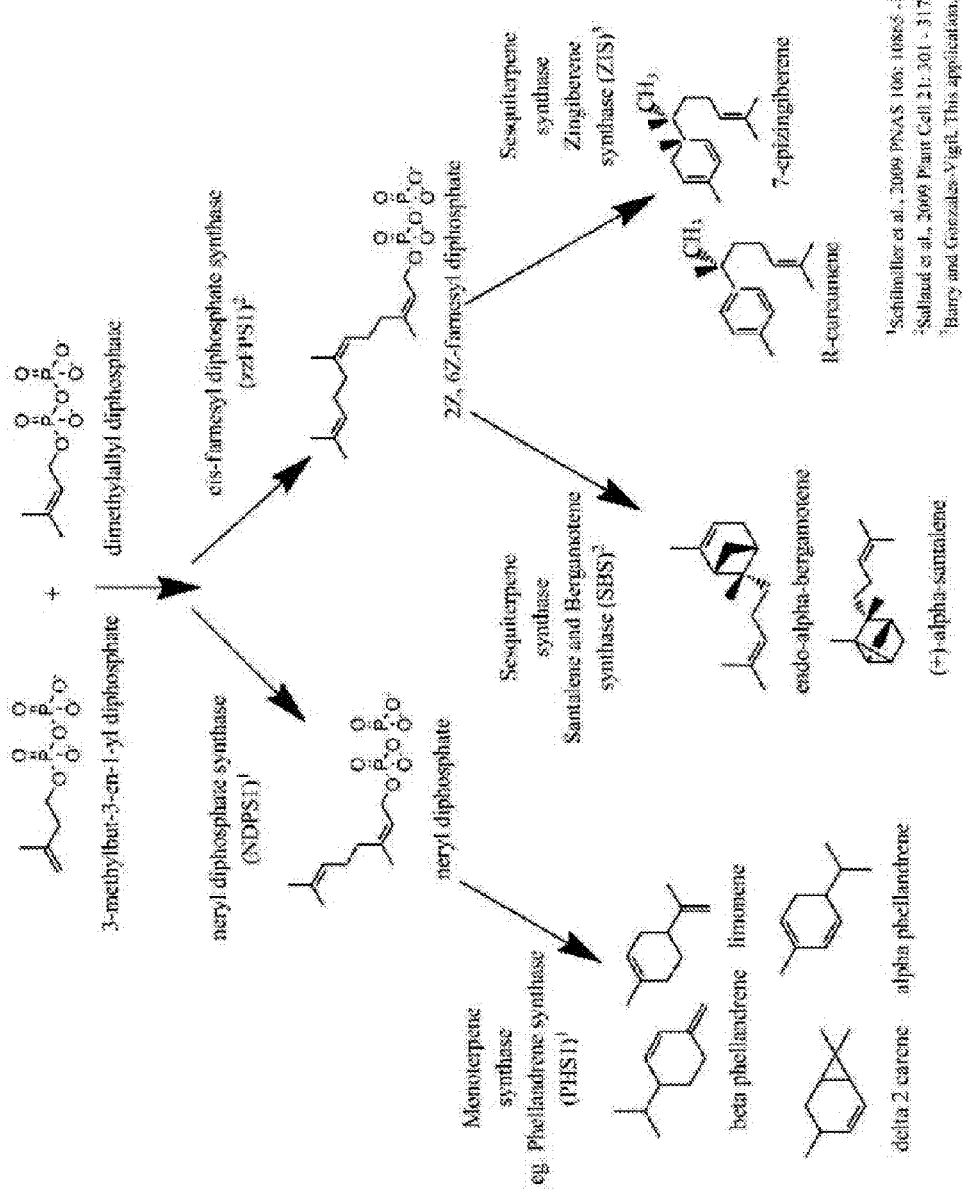
FIG. 10 illustrates the biosynthetic pathway for various terpenes. As shown, zingiberene is made from the cis substrate 2Z,6Z-farnesyl diphosphate rather than EE-FPP (a common substrate for sesquiterpenes). This newly identified pathway operates in tomato and closely related species.

FIG. 10 shows a proposed pathway for synthesis of terpenes in the glandular trichomes of *solanum* species that use the substrate 2Z,6Z-farnesyl diphosphate (2Z,6Z-FPP). As illustrated herein, the zingiberene synthase from accession LA2167 is very specific in the substrate it employs—it only uses 2Z,6Z-farnesyl diphosphate (2Z,6Z-FPP).

The percent of sesquiterpene product that is synthesized as zingiberene can vary. For example, one type of sesquiterpene synthase may synthesize substantially all zingiberene (i.e., one of zingiberene, 7-epi-zingiberene, S-curcumene, R-curcumene, alpha-zingiberene or a combination thereof). Another type of sesquiterpene synthase may synthesize a high percentage of zingiberene (i.e., one of zingiberene, 7-epi-zingiberene, S-curcumene, R-curcumene, alpha-zingiberene or a combination thereof) as well as other types of sesquiterpenes. Thus, the percent zingiberene in the mixture of sesquiterpenes made by a zingiberene synthase can vary from about 50% to about 99%, or about 55% to about 98%, or about 60% to about 97%, or about 65% to about 96%, or about 70% to about 95%, or any numerical range or percentage therein. As illustrated herein, about 95% of the sesquiterpene product synthesized by the LA2167-ZIS enzyme is zingiberene (e.g., one of zingiberene, 7-epi-zingiberene, S-curcumene, R-curcumene, alpha-zingiberene or a combination thereof).

The wild tomato species *Solanum habrochaites* has documented resistance to insect pests. Researchers have shown that such resistance is mediated in part by the volatile sesquiterpenes synthesized in the trichomes present on the leaves of this plant species. Zingiberene is one such insect repelling sesquiterpene.

In some embodiments, organisms are generated that have the sesquiterpene synthase nucleic acids and/or enzymes described herein. The sesquiterpene synthase nucleic acids and/or enzymes can supply zingiberene to the organism and/or the organism can be used to efficiently and inexpensively manufacture zingiberene. Thus, the invention relates to plants and other organisms (e.g., microorganisms) that can synthesize zingiberene because they have been modified to contain the sesquiterpene synthase nucleic acids and/or enzymes described herein. Such plants are resistant to insects. The invention also relates to methods of producing insect repellents and insecticides by use of nucleic acids and/or enzymes described herein.

Pursuant to the present disclosure, new sesquiterpene synthase genes have been isolated and characterized that provide plants with the ability to synthesize zingiberene. For example, the LA2167 strain of *Solanum habrochaites* was identified as having a sesquiterpene synthase gene, named herein the LA2167-ZIS gene, which expresses an enzyme that primarily synthesizes zingiberene.

Therefore, one aspect of the invention is a LA2167-ZIS nucleic acid with the sequence shown below (SEQ ID NO:1), where the bold and underlined codons are the start and stop codons.

```
  1 ATGATAGTTG GCTATAGAAG CACAATCATA ACCCTTTCTC

41 ATCCTAAGCT AGGCAATGGG AAAACAATTT CATCCAATGC

81 AATTTTCCGG AGATCATGTA GAGTAAGATG CAGCCACAGT

121 ACCCCTTCAT CAATGAATGG TTTCGAAGAT GCAAGGGATA

161 GAATAAGGGA AAGTTTTGGG AAAGTAGAGT TATCTCCTTC

201 TTCCTATGAC ACAGCATGGG TAGCTATGGT CCCTTCAAAA

241 CATTCACTAA ATGAGCCATG TTTTCCACAA TGTTTGGATT

281 GGATTATTGA AAATCAAAGA GAAGATGGAT CTTGGGGACT

321 AAACCCTAGC CATCCATTGC TTCTTAAGGA CTCACTTTCT

361 TCCACTCTTG CATGTTTGCT TGCACTAACC AAATGGAGAG

401 TTGGAGATGA GCAAATCAAA AGAGGCCTTG GCTTTATTGA
```

```
 441 AACCCAGAGT TGGGCAATTG ATAACAAGGA TCAAATTTCA
 481 CCTCTAGGAT TTGAAATTAT ATTTCCCAGT ATGATCAAGT
 521 CTGCAGAAAA ACTAAACTTA AATCTAGCAA TTAACAAAAG
 561 AGATTCAACA ATTAAAAGAG CATTACAGAA TGAGTTCACG
 601 AGGAATATTG AATATATGAG TGAAGGATTT GGTGAATTAT
 641 GTGATTGGAA GGAAATAATA AAGTTACATC AAAGGCAAAA
 681 TGGTTCATTA TTTGATTCAC CAGCCACTAC TGCAGCTGCC
 721 TTGATTTACC ATCAGCATGA TAAAAAATGC TATGAATATC
 761 TTAATTCAAT CTTGCAACAA CACAAAAATT GGGTTCCCAC
 801 TATGTATCCA ACAAAGATAC ATTCATTGCT TTGCTTGGTT
 841 GATACACTTC AAAATCTTGG AGTACATCGG CATTTTAAAT
 881 CAGAAATAAA GAAAGCCCTA GATGAAATAT ACAGGCTATG
 921 GCAACAAAAG AATGAAGAAA TTTTCTCAAA TGTCACCCAT
 961 TGTGCTATGG CTTTTCGACT TCTAAGGATA AGCTACTATG
1001 ATGTCTCCTC AGATGAACTA GCAGAATTTG TGGATGAAGA
1041 ACATTTCTTT GCAACAAGTG GGAAATATAC AAGTCATGTT
1081 GAAATTCTTG AACTCCACAA AGCATCACAA TTGGCTATTG
1121 ATCATGAGAA AGATGACATT TTGGATAAGA TTAACAATTG
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACAA TTTTAAAATC
1321 TTAAAAGCAG CTTATAGGTC ACCTAACATT AACAATAAGG
1361 ACTTGTTTAT ATTTTCAATA CGCGACTTTG AATTATGCCA
1401 AGCTCAACAC CAAGAAGAAC TTCAACAACT CAAGAGGTGG
1441 TTTGAAGATT GTAGATTGGA CCAACTCGGA CTTTCGGAAC
1481 AATTTATATC TGCTAGTTAC TTATGTGCTA TTCCTATTGT
1521 CCCCGGGCCT GAATTATCCG ATGCTCGTCT CGTGTACGCG
1561 AAATACGTCA TGCTCTTGAC TATTGTCGAT GATCATTTCG
1601 AGAGTTTTGC ATCTACAGAT GAATGTCTCA ACATCATTGA
1641 ATTAGTAGAA AGGTGGGATG ACTATGCAAG TGTAGGTTAT
1681 AAATCTGAGA GGGTTAAAGT TTTATTTTCA ATGTTTTACA
1721 AATCAATAGA GGAGATTGCA ACAATTGCTG AAATTAAACA
1761 AGGACGATCT GTCAAAAATC ACCTTATTAA TTTGTGGCTT
1801 AAAGTGATGA AGTTGATGTT GATGGAACGA GTAGAGTGGT
1841 GTTCTGGCAA GACAATACCA AGAATAGAAG AGTATTTGTA
1881 TGTTAGTTCT ATAACATTTG GTTCAAGATT GATTCCTCTC
1921 ACAACACAAT ATTTTATTGG AATAAAAATA TCCAAAGATC
1961 TTTTAGAAAG TGATGAAATT TATGGTTTAT GCAATTTTAC
2001 CGGTATAGTC TTGAGGCTCC TCAATGATTT ACAAGATTCC
2041 AAGAGAGAAC AAAAGGAGGG CTCAATAAAT TTAGTCACAT
2081 TACTAATGAA AAGTATCTCT GAGGAAGAAG CTATAATGAA
2121 GATGAAGGAA ATCTTGGAAA TGAAAGAAG AGAGTTATTT
2161 AAAATGGTTT TAGTTCAAAA AAAGGGAAGC CAATTGCCTC
2201 AATTATGCAA AGAAATATTT TGGAGGACAT GCAAATGGGC
2241 TCATTTCACT TATTCACAAA CTGATAGATA TAGATTTCCA
2281 GAGGAAATGG AGAATCACAT TGATGAAGTC TTTTACAAAC
2321 CACTCAATCA TTAA
```

The SEQ ID NO:1 nucleotide sequence encodes the following amino acid sequence (SEQ ID NO:2), which is a sequence for the LA2167-ZIS sesquiterpene synthase.

```
  1 MIVGYRSTII TLSHPKLGNG KTISSNAIFR RSCRVRCSHS
 41 TPSSMNGFED ARDRIRESFG KVELSPSSYD TAWVAMVPSK
 81 HSLNEPCFPQ CLDWIIENQR EDGSWGLNPS HPLLLKDSLS
121 STLACLLALT KWRVGDEQIK RGLGFIETQS WAIDNKDQIS
161 PLGFEIIFPS MIKSAEKLNL NLAINKRDST IKRALQNEFT
201 RNIEYMSEGF GELCDWKEII KLHQRQNGSL FDSPATTAAA
241 LIYHQHDKKC YEYLNSILQQ HKNWVPTMYP TKIHSLLCLV
281 DTLQNLGVHR HFKSEIKKAL DEIYRLWQQK NEEIFSNVTH
321 CAMAFRLLRI SYYDVSSDEL AEFVDEEHFF ATSGKYTSHV
361 EILELHKASQ LAIDHEKDDI LDKINNWTRT FMEQKLLNNG
401 FIDRMSKKEV ELALRNFYII SDLAENRRYI KSYEENNFKI
441 LKAAYRSPNI NNKDLFIFSI RDFELCQAQH QEELQQLKRW
481 FEDCRLDQLG LSEQFISASY LCAIPIVPGP ELSDARLVYA
521 KYVMLLTIVD DHFESFASTD ECLNIIELVE RWDDYASVGY
561 KSERVKVLFS MFYKSIEEIA TIAEIKQGRS VKNHLINLWL
601 KVMKLMLMER VEWCSGKTIP RIEEYLYVSS ITFGSRLIPL
641 TTQYFIGIKI SKDLLESDEI YGLCNFTGIV LRLLNDLQDS
681 KREQKEGSIN LVTLLMKSIS EEEAIMKMKE ILEMKRRELF
721 KMVLVQKKGS QLPQLCKEIF WRTCKWAHFT YSQTDRYRFP
761 EEMENHIDEV FYKPLNH
```

A codon optimized version of LA2167-ZIS open reading frame that lacks the predicted chloroplast targeting sequence from the N'-terminus was generated for expression in *E. coli*. The nucleotide sequence of this codon-optimized sequence is shown below as SEQ ID NO:3, where the bold and underlined codons are the start and stop codons.

```
  1 GGATCcATGA ATGGTTTTGA AGATGCCCGT GACCGTATCC
 41 GTGAATCGTT TGGTAAAGTG AACTGAGCC CGTCCTCGTA
 81 TGACACCGCC TGGGTTGCAA TGGTCCCGTC AAAACATTCG
121 CTGAACGAAC CGTGCTTTCC GCAATGTCTG GATTGGATTA
161 TCGAAAACCA GCGTGAAGAC GGCAGCTGGG GTCTGAATCC
```

-continued

```
 201 GTCTCACCCG CTGCTGCTGA AAGATAGCCT GAGCTCTACC
 241 CTGGCCTGTC TGCTGGCACT GACGAAATG GCGTGTGGGCG
 281 ACGAACAGAT TAAACGCGGC CTGGGTTTTA TCGAAACCCA
 321 AAGCTGGGCG ATCGATAACA AAGACCAGAT TTCTCCGCTG
 361 GGTTTTGAAA TTATCTTCCC GAGTATGATC AAATCCGCCG
 401 AAAAACTGAA CCTGAATCTG GCAATTAATA AACGTGATAG
 441 TACCATCAAA CGCGCCCTGC AGAACGAATT CACGCGTAAC
 481 ATCGAATACA TGTCCGAAGG CTTCGGTGAA CTGTGCGATT
 521 GGAAAGAAAT TATCAAACTG CACCAGCGCC AAAACGGCTC
 561 ACTGTTTGAT TCGCCGGCAA CCACGGCAGC AGCACTGATC
 601 TATCATCAGC ACGACAAAAA ATGTTACGAA TACCTGAACT
 641 CAATCCTGCA GCAACATAAA AATTGGGTTC CGACCATGTA
 681 CCCGACGAAA ATTCACTCGC TGCTGTGCCT GGTCGATACC
 721 CTGCAGAATC TGGGTGTGCA TCGTCACTTT AAAAGCGAAA
 761 TCAAAAAAGC CCTGGATGAA ATCTATCGCC TGTGGCAGCA
 801 GAAAAACGAA GAAATCTTTA GCAATGTGAC CCATTGTGCC
 841 ATGGCATTCC GTCTGCTGCG CATTTCTTAT TACGATGTTA
 881 GTTCCGACGA ACTGGCTGAA TTCGTCGATG AAGAACATTT
 921 CTTTGCGACC AGCGGCAAAT ACACGTCTCA TGTTGAAATC
 961 CTGGAACTGC ACAAAGCTAG CCAACTGGCG ATTGATCACG
1001 AAAAAGATGA CATCCTGGAC AAAATTAACA ATTGGACCCG
1041 TACGTTTATG GAACAGAAAC TGCTGAACAA CGGTTTCATC
1081 GATCGTATGA GTAAAAAAGA AGTGGAACTG GCCCTGCGCA
1121 ACTTTTATAT TATCAGTGAC CTGGCAGAAA ATCGTCGCTA
1161 CATCAAATCC TACGAAGAAA ACAACTTCAA AATCCTGAAA
1201 GCTGCGTACC GTTCACCGAA CATCAACAAC AAAGACCTGT
1241 TTATCTTCTC GATTCGCGAC TTTGAACTGT GCCAGGCGCA
1281 ACATCAGGAA GAACTGCAGC AACTGAAACG TTGGTTTGAA
1321 GATTGTCGCC TGGACCAACT GGGCCTGTCC GAACAGTTCA
1361 TCAGCGCCTC TTATCTGTGC GCAATTCCGA TCGTTCCGGG
1401 TCCGGAACTG TCTGATGCTC GCCTGGTGTA TGCGAAATAC
1441 GTTATGCTGC TGACCATTGT CGATGACCAC TTTGAAAGCT
1481 TCGCTTCTAC GGATGAATGC CTGAATATTA TCGAACTGGT
1521 GGAACGTTGG GATGACTATG CGAGTGTTGG CTACAAATCC
1561 GAACGCGTGA AAGTTCTGTT TTCAATGTTC TACAAATCGA
1601 TCGAAGAAAT TGCTACCATC GCGGAAATTA AACAGGGCCG
1641 TAGCGTCAAA AACCATCTGA TTAATCTGTG GCTGAAAGTC
1681 ATGAAACTGA TGCTGATGGA ACGTGTGGAA TGGTGTTCTG
1721 GTAAAACCAT CCCGCGCATT GAAGAATATC TGTACGTTTC
1761 ATCGATTACG TTTGGCAGTC GCCTGATCCC GCTGACCACG
```

-continued

```
1801 CAGTACTTCA TCGGTATCAA AATCAGTAAA GATCTGCTGG
1841 AATCCGACGA AATTTACGGC CTGTGCAACT TTACCGGTAT
1881 CGTGCTGCGT CTGCTGAATG ATCTGCAAGA CTCAAAACGC
1921 GAACAGAAAG AAGGCTCGAT TAATCTGGTT ACGCTGCTGA
1961 TGAAAAGTAT CTCCGAAGAA GAAGCGATCA TGAAAATGAA
2001 AGAAATCCTG GAAATGAAAC GTCGCGAACT GTTCAAAATG
2041 GTCCTGGTGC AGAAAAAAGG TAGCCAACTG CCGCAGCTGT
2081 GCAAAGAAAT CTTTTGGCGC ACCTGTAAAT GGGCCCATTT
2121 CACCTATAGC CAGACGGATC GTTACCGCTT CCCGGAAGAA
2161 ATGGAAAATC ACATTGACGA AGTGTTCTAC AAACCGCTGA
2201 ATCATTGAGT CGAC
```

The SEQ ID NO:3 nucleotide sequence encodes the following LA2167-ZIS 'codon optimized' amino acid sequence that lacks a chloroplast transit sequence (SEQ ID NO:4).

```
  1 MNGFEDARDR IRESFGKVEL SPSSYDTAWV AMVPSKHSLN
 41 EPCFPQCLDW IIENQREDGS WGLNPSHPLL LKDSLSSTLA
 81 CLLALTKWRV GDEQIKRGLG FIETQSWAID NKDQISPLGF
121 EIIFPSMIKS AEKLNLNLAI NKRDSTIKRA LQNEFTRNIE
161 YMSEGFGELC DWKEIIKLHQ RQNGSLFDSP ATTAAALIYH
201 QHDKKCYEYL NSILQQHKNW VPTMYPTKIH SLLCLVDTLQ
241 NLGVHRHFKS EIKKALDEIY RLWQQKNEEI FSNVTHCAMA
281 FRLLRISYYD VSSDELAEFV DEEHFFATSG KYTSHVEILE
321 LHKASQLAID HEKDDILDKI NNWTRTFMEQ KLLNNGFIDR
361 MSKKEVELAL RNFYIISDLA ENRRYIKSYE ENNFKILKAA
401 YRSPNINNKD LFIFSIRDFE LCQAQHQEEL QQLKRWFEDC
441 RLDQLGLSEQ FISASYLCAI PIVPGPELSD ARLVYAKYVM
481 LLTIVDDHFE SFASTDECLN IIELVERWDD YASVGYKSER
521 VKVLFSMFYK SIEEIATIAE IKQGRSVKNH LINLWLKVMK
561 LMLMERVEWC SGKTIPRIEE YLYVSSITFG SRLIPLTTQY
601 FIGIKISKDL LESDEIYGLC NFTGIVLRLL NDLQDSKREQ
641 KEGSINLVTL LMKSISEEEA IMKMKEILEM KRRELFKMVL
681 VQKKGSQLPQ LCKEIFWRTC KWAHFTYSQT DRYRFPEEME
721 NHIDEVFYKP LNH
```

Additional zingiberene synthase cDNAs from *Solanum habrochaites* accessions LA1731, LA2196, LA2106 and LA1352 have been isolated as described herein (see, Example 3). Thus, a number of zingiberene synthase enzymes are described herein, including zingiberene synthases with amino acid sequence SEQ ID NOs: 2, 4, 6, 8, 11, 12, 14, 16, and 18. As also described herein, the nucleic acid sequences encoding such zingiberene synthases include those with SEQ ID NOs: 1, 3, 5, 7, 13, 15, 17, and 19.

Related Zingiberene Synthases

These new zingiberene synthase nucleic acids and enzymes described herein allow identification and isolation of related nucleic acids and their encoded enzymes that also provide a means for production of zingiberene in plants.

For example, related nucleic acids can be isolated and identified by procedures available in the art. Similarly, mutations can be introduced into any of zingiberene synthase nucleic acids described herein (SEQ ID NO:1, 3, 5, 7, 13, 15, 17, 19 and combinations thereof). Similarly, the amino acid sequences of any of the zingiberene synthases can be evaluated and selected amino acid replacements, deletions and/or additions can be made to any of the SEQ ID NO: 2, 4, 6, 8, 11, 12, 14, 16, 18 and combinations of such amino acid sequences.

Thus, the zingiberene synthase nucleic acid sequences described herein can be used to isolate or generate additional zingiberene synthase nucleic acids. For example, additional zingiberene synthase nucleic acids can be isolated by sequence mutation and/or by hybridization to DNA and/or RNA isolated from other plant species using any of the SEQ ID NO:1, 3, 5, 7, 13, 15, 17, and 19 nucleic acids, or fragments thereof, as probes. In some embodiments, the zingiberene synthase nucleic acids (e.g., SEQ ID NO:1, 3, 5, 7, 13, 15, 17, and 19) are used as probes or templates for mutation.

The term "selectively hybridize" includes hybridization, under stringent hybridization conditions, of a target nucleic acid sequence to a selected nucleic acid probe sequence (e.g., SEQ ID NO:1, 3, 5, 7, 13, 15, 17, 19, or a fragment thereof) to a detectably greater degree (e.g., at least 2-fold over background) than hybridization of the probe to a non-target nucleic acid sequence, and to the substantial exclusion of non-target nucleic acids. Selectively hybridizing sequences typically have about at least 70% sequence identity, or 75-90% sequence identity, or 90-95% sequence identity, or 91-99% sequence identity, or 92-99% sequence identity, or 95-99% sequence identity, or 97-99% sequence identity, or 98-99% sequence identity, or 100% sequence identity (or complementarity) with each other. In some embodiments, a selectively hybridizing sequence has about at least about 91%, at least about 92%, at least about 93%, at least about 94%, at least about 95%, at least about 96%, at least 97%, at least 98%, or at least 99% sequence identity with any of SEQ ID NO:1, 3, 5, 7, 13, 15, 17, 19, or a fragment thereof.

Thus, the nucleic acids of the invention include those with about 800 of the same nucleotides as SEQ ID NO:1, 3, 5, 7, 13, 15, 17, or 19; or about 1000 of the same nucleotides thereof; or about 1200 of the same nucleotides thereof; or about 1400 of the same nucleotides thereof; or about 1500 of the same nucleotides thereof; or about 1600 of the same nucleotides thereof; or about 1700 of the same nucleotides thereof; or about 1800 of the same nucleotides as thereof; or about 1800 of the same nucleotides thereof; or about 2000 of the same nucleotides thereof; or about 800-2000 of the same nucleotides as SEQ ID NO:1, 3, 5, 7, 13, 15, 17, or 19. The identical nucleotides or amino acids can be distributed throughout the nucleic acid, and need not be contiguous.

Such nucleic acids can express a zingiberene synthase with about 650 of the same amino acids as any of the SEQ ID NO: 2, 4, 6, 8, 11, 12, 14, 16, and 18 amino acid sequences; or about 655 of the same amino acids thereof; or about 660 of the same amino acids thereof; or about 665 of the same amino acids thereof; or about 670 of the same amino acids thereof; or about 675 of the same amino acids thereof; or about 680 of the same amino acids thereof; or about 685 of the same amino acids thereof; or about 690 of the same amino acids thereof; or about 695 of the same amino acids thereof; or about 700 of the same amino acids thereof; or about 705 of the same amino acids thereof; or about 708 of the same amino acids thereof; or about 710 of the same amino acids thereof; or about 712 of the same amino acids thereof; or about 715 of the same amino acids thereof; or about 716 of the same amino acids thereof; or about 717 of the same amino acids thereof; or about 718 of the same amino acids thereof; or about 719 of the same amino acids thereof; or about 720 of the same amino acids thereof; or about 722 of the same amino acids thereof; or about 724 of the same amino acids thereof; or about 725 of the same amino acids thereof; or about 726 of the same amino acids thereof; or about 727 of the same amino acids thereof; or about 728 of the same amino acids thereof; or about 729 of the same amino acids thereof; or about 730 of the same amino acids thereof; or about 731 of the same amino acids thereof; or about 732 of the same amino acids thereof.

Note that if a value of a variable that is necessarily an integer, e.g., the number of nucleotides or amino acids in a nucleic acid or protein, is described as a range, e.g., 90-99% sequence identity, what is meant is that the value can be any integer within that range, e.g. for 90-99% sequence identity, any integer between 90 and 99 inclusive, i.e., 90, 91, 92, 93, 94, 95, 96, 97, 98 or 99.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified which can be up to 100% complementarity to the probe (homologous probing). Alternatively, stringency conditions can be adjusted to allow some mismatching in sequences so that lower degrees of similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl (Anal. Biochem. 138:267-84 (1984)):

$T_m=81.5°$ C.$+16.6$ (log M)$+0.41$ (% GC)$-0.61$ (% formamide)$-500/L$ where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$). Moderately stringent conditions can utilize a hybridization reaction and/or a wash at 6, 7, 8, 9 or 10° C. lower than the thermal melting point ($T_m$). Low stringency conditions can involve hybridizations and/or washes at 11, 12, 13, 14, 15 or 20° C. lower than the thermal melting point ($T_m$). Using the equation, hybridization and wash compositions, and desired $T_m$, those of ordinary skill can identify and isolate nucleic acids with sequences related to SEQ ID NO: 1, 3, 5, 7, 13, 15, 17, and/or 19. Those of skill in the art also understand how to vary the hybridization and/or wash solutions. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison (e.g., any of nucleotide sequences SEQ ID NO:1, 3, 5, 7, 13, 15, 17, or 19; or any of amino acid sequences SEQ ID NO: 2, 4, 6, 8, 11, 12, 14, 16, or 18). A reference sequence may be a subset or the entirety of a specified sequence; for example, as a segment of a full-length cDNA or genomic DNA sequence, or the complete cDNA or genomic DNA sequence, a complete amino acid sequence or a domain of a polypeptide sequence.

As used herein, "comparison window" means includes reference to a contiguous and specified segment of a nucleic acid or an amino acid sequence, wherein the nucleic acid/amino acid sequence may be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States, Comput. Chem. 17:191-201 (1993)) low-complexity filters can be employed alone or in combination.

The terms "substantial identity" indicates that a polypeptide or nucleic acid comprises a sequence with between 85-100% sequence identity to a reference sequence, or at least 85% sequence identity, or at least 86% sequence identity, or at least 87%, or at least 88% sequence identity, or at least 89% sequence identity, or at least 90% sequence identity, or at least 91% sequence identity, or at least 92% sequence identity, preferably 93%, more preferably 94%, most preferably at least 95%, or 96%, or 97%, or 98% or 99% sequence identity to the reference sequence over a specified comparison window. Optimal alignment may be ascertained or conducted using the homology alignment algorithm of Needleman and Wunsch, supra.

An indication that two polypeptide sequences are substantially identical is that both polypeptides have zingiberene synthase activity, meaning that both polypeptides can synthesize the desired zingiberene. The polypeptide that is substantially identical to a zingiberene synthase with one of the SEQ ID NO sequences described herein may not have exactly the same level of activity as the zingiberene synthase with the exact SEQ ID NO sequence recited herein. Instead, the substantially identical polypeptide may exhibit greater or lesser levels of zingiberene synthase activity than the zingiberene synthases described herein, as measured by assays available in the art or described herein (see, e.g., Example 1). For example, the substantially identical polypeptide may have at least about 70%, or at least about 75%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of a zingiberene synthase with a sequence (SEQ ID NO) described herein when measured by similar assay procedures.

Alternatively, substantial identity is present when second polypeptide is immunologically reactive with antibodies raised against the first polypeptide (e.g., a polypeptide with any of amino acid sequences SEQ ID NO: 2, 4, 6, 8, 11, 12, 14, 16, and 18). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides, which are "substantially similar" share sequences as, noted above except that residue positions, which are not identical, may differ by conservative amino acid changes.

The zingiberene synthase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99 N-terminal amino acid residues of any of amino acid sequences SEQ ID NO: 2, 4, 6, 8, 11, 12, 14, 16, and/or 18. Alternatively, the zingiberene synthase polypeptides of the present invention may include the last 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of any of amino acid sequences SEQ ID NO: 2, 4, 6, 8, 11, 12, 14, 16, and/or 18.

Hosts and Host Cells Modified to Contain a Zingiberene Synthase

In order to engineer a cell or an organism to synthesize zingiberene, one of skill in the art can introduce a zingiberene synthase enzyme and/or a nucleic acid encoding such a zingiberene synthase into the cell or organism. In some embodiments, the cell or organism is a plant. In other embodiments, the cell or organism is a microorganism (e.g., a bacterial or yeast cell). Other eukaryotic and prokaryotic cells and organisms can also be modified to contain the zingiberene synthase enzymes and/or nucleic acids described herein.

Any plant that can benefit from the insect-repelling properties of zingiberene can be modified to express a nucleic acid encoding a zingiberene synthase that can synthesize zingiberene. Alternatively, the plant can be treated by introduction of a zingiberene synthase enzyme or by application of zingiberene. Examples of plants that can be treated with such a zingiberene and/or zingiberene synthase and/or that can be engineered to synthesize such zingiberenes include, but are not limited to, vegetable-producing plants, grain-producing plants, tuber-producing plants, sugar-producing plants, nut-producing, fruit-producing plants, flowering plants, fuel-producing plants and wood-producing plants. The plant can be an ornamental plant or a plant cultivated to repel insects, for example, near patios and barns. In some embodiments, the plant can be a tomato, broccoli, green bean, sweet pea, squash, eggplant, asparagus, artichoke, avocado, celery, carrot, radish, cucumber, potato, lettuce, spinach, soybean, grape, orange, lemon, grapefruit, corn, tobacco, cotton, canola, alfalfa, rice, wheat, oats, sorghum and/or flax plant. In some embodiments, one of skill in the art can inject a zingiberene synthase enzyme into young plants. Alternatively, one of skill in the art can generate genetically-modified plants that contain nucleic acids encoding zingiberene synthases within their somatic and/or germ cells.

Genetic modification of organisms can be accomplished by procedures available in the art. For example, one of skill in the art can prepare an expression cassette or expression vector that can express one or more encoded zingiberene synthase enzymes. Host cells can be transformed by such an expression cassette or expression vector, and organisms (including whole plants and their seeds) can be generated from the host cells that were successfully transformed with the zingiberene synthase nucleic acids. Some procedures for making such genetically modified organisms (including microorganisms and plants (and their seeds)) are described below.

Promoters: The zingiberene synthase nucleic acids and nucleic acids related to the zingiberene synthase nucleic acids set forth herein can be operably linked to a promoter, which provides for expression of mRNA from the nucleic acids. The promoter is typically a promoter functional in plants and/or seeds, and can be a promoter functional during plant growth and development. A nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the Ptac promoter can be induced to varying levels of gene expression depending on the level of isothiopropylgalactoside added to the transformed bacterial cells. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

Expression cassettes generally include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), Adh1 (Walker et al., *Proc. Natl. Acad. Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Mol. Cell. Biol*. 12:3399 (1992)), cab (Sullivan et al., *Mol. Gen. Genet*. 215:431 (1989)), PEPCase (Hudspeth et al., *Plant Molecular Biology*. 12:579-589 (1989)) or those associated with the R gene complex (Chandler et al., *The Plant Cell*. 1:1175-1183 (1989)). Further suitable promoters include cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J*. 3:1671 (1971)) and the actin promoter from rice (McElroy et al., *The Plant Cell*. 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are known to those of skill in the art.

Alternatively, novel tissue-specific promoter sequences may be employed in the practice of the present invention. Zingiberene synthase nucleic acids from a particular plant or plant tissue are isolated and selected nucleic acids (e.g., those that are expressed specifically in that tissue) are identified, for example, using Northern blotting. The zingiberene synthase nucleic acids are generally not present in a high copy number, but are relatively abundant in specific tissues (e.g., trichomes).

In some embodiments, the promoter and control elements of corresponding genomic clones of zingiberene synthase nucleic acids are used to generate genetically modified plants. The promoter and control elements of corresponding genomic clones can also be localized using techniques well known to those of skill in the art. In other embodiments, selected promoter and control elements are used, for example, to optimize expression in a selected organism or tissue.

A zingiberene synthase nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The zingiberene synthase nucleic acids can be subcloned downstream from the promoter using restriction enzymes and positioned to ensure that the DNA is inserted in proper orientation with respect to the promoter so that the DNA can be expressed as sense or antisense RNA. Once the zingiberene synthase nucleic acid is operably linked to a promoter, the expression cassette so formed can be subcloned into a plasmid or other vector (e.g., an expression vector).

In some embodiments, a cDNA clone encoding a zingiberene synthase protein is isolated from *Solanum habrochaites* trichome tissue. In other embodiments, cDNA clones from other species (that encode a zingiberene synthase protein) are isolated from selected plant tissues, or a nucleic acid encoding a mutant or modified zingiberene synthase protein is prepared by available methods or as described herein. For example, the nucleic acid encoding a mutant or modified zingiberene synthase protein can be any nucleic acid with a coding region that hybridizes to any of nucleotide sequences SEQ ID NO:1, 3, 5, 7, 13, 15, 17, and/or 19, and that has terpene synthase activity. Using restriction endonucleases, the entire coding sequence for the terpene synthase is subcloned downstream of the promoter in a 5' to 3' sense orientation.

Targeting Sequences: Additionally, expression cassettes can be constructed and employed to target the nucleic acids to an intracellular compartment within the host (e.g., plant) cells or to direct an encoded protein to the extracellular environment. This can generally be achieved by joining a DNA sequence encoding a transit or signal peptide sequence to the coding sequence of the nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences: When the expression cassette is to be introduced into a host cell, the expression cassette can also optionally include 3' nontranslated host regulatory DNA sequences that act as a signal to terminate transcription and allow for the polyadenylation of the resultant mRNA. The 3' nontranslated regulatory DNA sequence preferably includes from about 300 to 1,000 nucleotide base pairs. When the host cell is a plant cell, the 3' nontranslated regulatory DNA sequence can contain plant transcriptional and translational termination sequences. For example, 3' elements that can be used include those derived from the nopaline synthase gene of *Agrobacterium tumefaciens* (Bevan et al., *Nucleic Acid Research*. 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed, including those useful in bacteria and/or yeast. For example, some 3' non-translated regulatory sequences can be obtained as described in An (*Methods in Enzymology*. 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the zingiberene synthase nucleic acids by standard methods.

Selectable and Screenable Marker Sequences: In order to improve identification of transformants, a selectable or screenable marker gene can be employed with the expressible zingiberene synthase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, and which polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Stiefel et al., *The Plant Cell*. 2:785-793 (1990)) is well characterized in terms of molecular biology, expression, and protein structure and therefore can readily be employed. However, any one of a variety of extensins and/or glycine-rich wall proteins (Keller et al., *EMBO J*. 8:1309-1314 (1989)) could be modified by the addition of an antigenic site to create a screenable marker. Numerous other possible selectable and/or screenable marker genes will be apparent to those of skill in the art in addition to the one set forth herein below.

It will be understood that the discussion herein is exemplary rather than exhaustive. In light of the techniques disclosed herein and the general recombinant techniques which are known in the art, the present invention renders possible the introduction of any gene, including marker genes, into a recipient host cell, for example, to generate a transformed plant cell or a transformed microorganism.

Possible selectable markers for use in connection with the present invention include, but are not limited to, a neo gene (Potrykus et al., *Mol. Gen. Genet*. 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology*. 6:915-922 (1988)) thus conferring glyphosate resistance; a nitrilase gene such as bxn from *Klebsiella ozaenae* which confers resistance to bromoxynil (Stalker et al., *Science*. 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem*. 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet*. 205:42-50 (1986); Twell et al., *Plant Physiol*. 91:1270-1274 (1989)) causing rapid accumulation of ammonia and cell death. The success in using this selective system in conjunction with monocots was particularly surprising because of the major difficulties which have been reported in transformation of cereals (Potrykus, *Trends Biotech*. 7:269-273 (1989)).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts, 18th Stadler Genetics Symposium*, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green fluorescent protein gene (Niedz et al., *Plant Cell Reports.* 14:403 (1995).

For example, genes from the maize R gene complex can be used as screenable markers. The R gene complex in maize encodes a protein that acts to regulate the production of anthocyanin pigments in most seed and plant tissue. Maize strains can have one or as many as four, R alleles which combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene would be valuable in directing the expression of genes, e.g., insect resistance, drought resistance, herbicide tolerance or other protein coding regions. In some embodiments, any of the various R gene family members may be employed (e.g., P, S, Lc, etc.). For example, the Sn (particularly Sn:bol3) dominant member of the R gene complex can be used; Sn is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on cell or tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (for example, encoding antibiotic or herbicide resistance), unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153: 292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the co/E1 replication of origin and a wide host range replicon. The binary Ti vectors carrying an expression cassette of the invention can be used to transform both prokaryotic and eukaryotic cells. In some embodiments, the binary Ti vectors carrying an expression cassette of the invention can be used to transform dicot plant cells.

In Vitro Screening of Expression Cassettes: Once the expression cassette is constructed and subcloned into a suitable plasmid, it can be screened for the ability to synthesize zingiberene by standard methods. Suitable vectors include plasmids such as those described herein. Vectors containing expression cassettes that synthesize zingiberenes can be identified by transforming a bacterial host cell (e.g., *E. coli*) with the vector and observing whether the bacterial host cell synthesizes zingiberene when supplied with a suitable substrate (e.g., 2Z,6Z-Farnesyl diphosphate, when synthesizing zingiberene).

DNA Delivery of the DNA Molecules into Host Cells: The present invention generally includes steps directed to introducing a zingiberene synthase nucleic acids, such as a preselected cDNA encoding the selected synthase enzyme, into a recipient cell to create a transformed cell. The frequency of occurrence of cells taking up exogenous (foreign) DNA may be low. Moreover, it is most likely that not all recipient cells receiving DNA segments or sequences will result in a transformed cell wherein the DNA is stably integrated into the host cell genome and/or expressed. Some may show only initial and transient gene expression. However, certain cells from virtually any bacterial, yeast, dicot or monocot species may be stably transformed. The dicot and/or monocot plant cells can then regenerated into transgenic plants, through the application of the techniques disclosed herein.

Thus, one aspect of the invention is a host cell containing one of the synthase nucleic acids described herein, or a nucleic acid that hybridizes thereto. Such a host cell can be a microorganism or a plant cell.

Another aspect of the invention is a plant species with a zingiberene, for example, zingiberene, in the trichomes of its leaves, wherein the plant has an introduced zingiberene synthase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include vegetable-producing plants, grain-producing plants, sugar-producing plants, nut-producing, fruit-producing plants, flowering plants, fuel-producing plants and wood-producing plants. The plant can be an ornamental plant or a plant cultivated to repel insects, for example, near patios and barns. In some embodiments, the plant can be a tomato, broccoli, green bean, sweet pea, squash, eggplant, asparagus, artichoke, avocado, celery, carrot, radish, cucumber, potato, lettuce, spinach, soybean, grape, orange, lemon, grapefruit, corn, tobacco, cotton, canola, alfalfa, rice, wheat, oats, sorghum and/or flax plant.

For example, the plant or a plant cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Many of these procedures can also be employed for transformation of a bacterial or yeast host cell. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are useful tissue sources. Selection of tissue sources for transformation of monocots is described in detail in U.S. application Ser. No. 08/112,245 and PCT publication WO 95/06128. See also WO/2010/099985, which is specifically incorporated herein by reference in its entirety.

The transformation is carried out under conditions directed to the plant tissue of choice. The plant cells or tissue are exposed to the DNA or RNA carrying the synthase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target plant cells more susceptible to transformation by electroporation than untreated cells. Alternatively, recipient cells can be made more susceptible to transformation, by mechanical wounding.

To effect transformation by electroporation, one may employ either friable tissues such as a suspension host cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to host cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells.

It is contemplated that particles may contain DNA rather than be coated with DNA. Hence the particles may increase the level of DNA delivery but are not, in and of themselves, necessary to introduce DNA into plant cells.

An advantage of microprojectile bombardment, in addition to it being an effective means of reproducibly stably transforming plants, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with plant cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, host cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of a synthase nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible synthase nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the synthase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced synthase nucleic acids, the plant is self-pollinated at least once in order to produce a homozygous backcross converted inbred containing the synthase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the synthase nucleic acids (or the synthase enzyme). For example, transgenic plant and/or seed tissue can be analyzed for zingiberene synthase expression using standard methods such as SDS polyacrylamide gel electrophoresis and/or detection of a zingiberene in the leaves and/or trichomes of plants.

Once a transgenic seed expressing the synthase sequence and having increased zingiberene in the plant arising from the seed is identified, the seed can be used to develop true breeding plants. The true breeding plants are used to develop a line of plants with an increase in the percent of zingiberene in the plant while still maintaining other desirable functional agronomic traits. Adding the trait of increasing the percent of zingiberene in plants can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of zingiberene in the plant. The resulting progeny are then crossed back to the parent that expresses the increased zingiberene trait. The progeny from this cross will also segregate so that some of the progeny carry the trait and some do not. This back-crossing is repeated until an inbred line with the desirable functional agronomic traits, and with expression of the trait involving an increase in zingiberene, for example, within the trichomes of the plant. Such expression of the increased percentage of zingiberene in the plant can be expressed in a dominant fashion.

Subsequent to back-crossing, the new transgenic plants can be evaluated for an increase in the weight percent of zingiberene in the plant. This can be done, for example, by NMR, gas chromatography, mass spectroscopy and other analyses of leaf trichome isolates. The new transgenic plants can also be evaluated for a battery of functional agronomic characteristics such as yield, resistance to disease, resistance to insect pests, drought resistance, and/or herbicide resistance.

Determination of Stably Transformed Plant Tissues: To confirm the presence of the zingiberene synthase nucleic acids in the regenerating plants, or seeds or progeny derived from the regenerated plant, a variety of assays may be performed. Such assays include, for example, zingiberene detection assays and/or molecular biological assays available to those of skill in the art. Such assays can include Southern and Northern blotting and PCR; biochemical assays, such as detecting the presence of a protein product, e.g., by immunological means (ELISAs and Western blots) or by enzymatic function; plant part assays, such as leaf, trichome, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced zingiberene synthase nucleic acids. PCR also be used to reverse transcribe RNA into DNA, using enzymes such as reverse transcriptase, and then through the use of conventional PCR techniques amplify the DNA. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the zingiberene synthase nucleic acid in question, they do not provide information as to whether the preselected DNA segment is being expressed. Expression may be evaluated by specifically identifying the protein products of the introduced zingiberene synthase nucleic acids, by detecting synthesis of zingiberene or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the zingiberene synthase such as evaluation by amino acid sequencing following purification. The Examples of this application also provide assay procedures for detecting and quantifying zingiberene synthase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Figure 7:
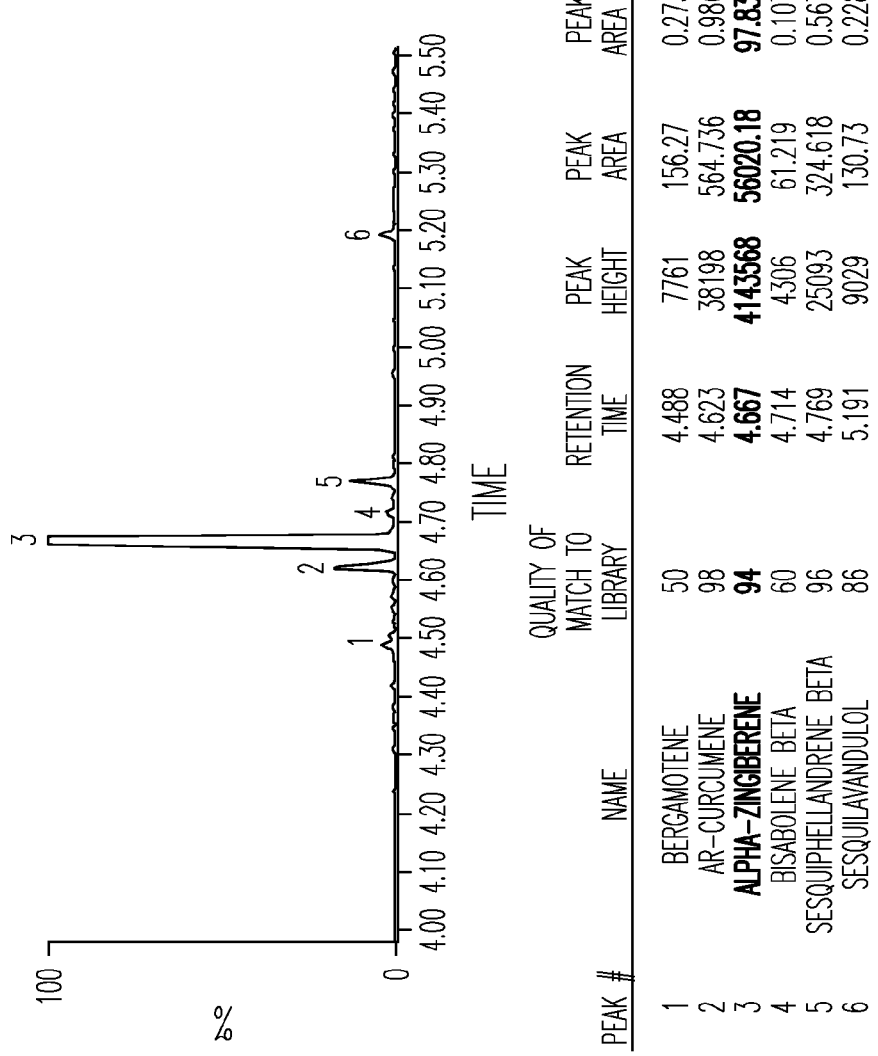
FIG. 7 illustrates the identification of products synthesized by E. coli cultures expressing the recombinant LA2167-ZIS zingiberene synthase+2Z,6Z-FPP as a substrate. Note that zingiberene constitutes greater than 95 percent of the total products synthesized. The extracted ion chromatogram of ion 93 is shown.

As illustrated herein, the SEQ ID NO:3 open reading frame was cloned into an expression vector pHIS8 and expressed in *E. coli* BL21 DE3 cells. While several zingiberenes were synthesized in cultures of these *E. coli* cells (FIG. 6), zingiberene constituted greater than 95% of the products that were obtained (FIG. 7). The Examples further illustrate some aspects of the invention.

Making Zingiberene

In another embodiment, the zingiberene synthase nucleic acids and enzymes described herein can be used to make zingiberene. Compositions of zingiberene can also be prepared that are useful as fragrances, insect repellents and/or insecticides.

For example, zingiberene compounds can be synthesized in recombinant microorganisms, such as bacteria (e.g. *E. coli*) or fungi (e.g. yeasts, including *Saccharomyces*, *Pichia* or *Hansenula*), or in algae. Thus, for example, the nucleic acids encoding one or more zingiberene synthases can be incorporated into a convenient host cell and the synthase expressed within these host cells can make the zingiberene. These methods allow large quantities of substantially pure zingiberene compounds to be made that are substantially free of other types of monoterpenes and sesquiterpenes.

Recombinant expression of zingiberene synthases can be accomplished using procedures, and expression systems available in the art. The expression systems can contain control sequences, such as promoters, and preferably enhancers and termination controls for expressing the zingiberene synthases in a variety of hosts. Such control sequences and other regulatory elements include those described herein and those available in the art. See e.g., Sambrook et al., Molecular Cloning a Laboratory Manual, Second Ed. Cold Spring Harbor Press (1989) and Sambrook et al., Molecular Cloning a Laboratory Manual, Third Ed. Cold Spring Harbor Press (2001).

Thus, the zingiberene synthase nucleic acids can be incorporated into prokaryotic and/or eukaryotic systems to provide a system that generates large quantities of zingiberenes. The most commonly used prokaryotic system is *E. coli*, although other systems such as *B. subtilis* and *Pseudomonas* can also be used. Suitable control sequences for prokaryotic systems include both constitutive and inducible promoters including the lac promoter, the trp promoter, hybrid promoters such as tac promoter, the lambda phage P1 promoter. In general, the zingiberene synthase may be produced in these hosts either as a fusion or mature protein. When the desired zingiberene synthase sequences are produced as mature proteins, the sequence produced may be preceded by a methionine which is not necessarily efficiently removed. So long as the zingiberene synthase efficiently produces zingiberene, there may be no need to remove the methionine or otherwise alter the zingiberene synthase sequence. Accordingly, the zingiberene synthase claimed herein may be preceded by an N-terminal Met when produced in bacteria. Moreover, constructs may be made wherein the coding sequence for the zingiberene synthase is preceded by an operable signal peptide which results in the secretion of the zingiberene synthase protein. When produced in prokaryotic hosts in this matter, the signal sequence is removed upon secretion.

A wide variety of eukaryotic hosts are also now available for production of recombinant foreign proteins. As with bacterial host cells, eukaryotic hosts may be transformed with expression systems which produce the zingiberene synthase. Eukaryotic systems have the additional advantage that they are able to process introns which may occur in the genomic sequences encoding proteins of higher organisms. Eukaryotic systems also provide a variety of processing mechanisms which result in, for example, glycosylation, oxidation or derivatization of certain amino acid residues, conformational control, and so forth.

Commonly used eukaryotic systems include yeast, insect cells, mammalian cells, avian cells, and cells of higher plants. Suitable promoters are available which are compatible and operable for use in each of these host types as well as are termination sequences and enhancers, as e.g. the baculovirus polyhedrin promoter. As above, promoters can be either constitutive or inducible.

Zingiberene Compositions

The zingiberene compounds generated from genetically modified organisms can be incorporated into a fragrance, insect repellent and/or insecticidal composition. The composition can comprise, or consist essentially, or consist of a zingiberene. The composition can include an effective amount of such a zingiberene compound. In some embodiments, the zingiberene compositions contain significant amounts of zingiberene.

In the context of insect repellent and/or insecticidal compositions, an "effective amount" of a zingiberene refers to an amount sufficient to significantly decrease the infestation and/or damage caused by insect pests (especially by one or more sap-sucking insect pests such as whiteflies) on treated plants compared to untreated plants. In the context of mammalian insect pests, an effective amount of a zingiberene refers to an amount sufficient to significantly repel the insects compared to an untreated mammal.

The composition can be in the form of a volatile/gas, a liquid, a semi-solid (e.g., gel beads, creams, foams, etc.) or as a solid (granules, powders, etc.). The composition can contain an inert carrier, such as a solvent. The carrier or solvent can be an aqueous carrier or solvent. In other embodiments, the carrier or solvent is an organic carrier or solvent. Examples of carriers and/or solvents include an alcohol (e.g. ethanol) or ether (e.g. pentane ether) or another organic solvent (e.g. hexane), which does preferably not have any effect on whitefly behavior. The carrier can also be oil-based. The zingiberene(s) can be dissolved in a solvent, such as alcohol, ether or alcohol/ether mixture. The carrier (e.g., an oil) can be added to the solvent-zingiberene mixture. In some embodiments, water may not be a very suitable solvent because the zingiberenes are lipophilic and may not be miscible in water.

The composition of the zingiberene(s) is generated so that it can easily be applied to the target location in an effective manner, for example, so that insect behavior is affected. The insect distribution in the applied area can be significantly affected, or significantly diminished.

In some embodiments, the compositions are formulated for topical application to an animal such as a human, a zoo animal or a domesticated animal. For topical administration, the zingiberenes may be formulated as is known in the art for direct application to a target area. Compositions for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include ointments, creams, lotions, pastes, jellies, sprays, and aerosols. Alternatively, the zingiberene can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a zingiberene of the invention present in a topical formulation will depend on various factors, but generally will be from 0.01% to 95% of the total weight of the formulation, and typically 0.1-85% by weight.

The repellent compounds and/or compositions are in one embodiment applied to crop plants. When applied to plants, e.g. in the field or in greenhouses, a gas, liquid (e.g. which evaporates upon contact with air) or semi-solid form may be preferred, which can be sprayed or dispersed onto the aerial plant surface. Solid compositions include granules, powders, slow-release matrices (e.g. coatings or matrices surrounding the active ingredient and releasing the ingredient slowly) and the like. The active ingredient and carrier (e.g. the solvent) may also be placed into a solid container from which the volatiles are released slowly.

The skilled person will know how to make an appropriate composition, for example, by taking the following factors into consideration: 1. percent of active ingredient, 2. ease in handling and mixing, 3. safety for humans and non-target animals (such as insect pest predators or parasites), 4. environment where the composition is to be applied (field, greenhouse, park, woodland, etc.), 5. habits of the target insect (e.g. whiteflies and/or other insect pests), 6. the crop to be protected and possible injury to the crop.

The types of composition can vary. For example, the compositions can include the following: a) Emulsified Concentrates (EC) compositions, which are liquid compositions wherein the active ingredient(s) is/are dissolved in oil or another solvent and wherein an emulsifier is added so that the composition can be mixed with oil or water for spraying; b) High concentrate liquids, spray concentrates and ULVs (ultra low volume concentrates), which contain high concentrations of active ingredient(s) and are generally diluted by mixing with oil or water, or are used without dilution directly; c) Low concentrate liquids or oil solutions, which generally require no further dilution and comprise the active ingredient(s) in the appropriate application dosage; d) Flowable liquids can be made for active ingredients that do not dissolve well in water or oil. The active ingredient can be a solid, which is ground or in fine powder form. The fine solid is then suspended in liquid (together with suspending agents, adjuvants and/or other ingredients); e) Solutions, or water soluble concentrates, which are liquid compositions, made by dissolving the active ingredient(s) in a solvent (e.g. water or organic solvents); f) Encapsulated compositions, whereby the active ingredient/s is/are contained in small capsules or coatings, which in turn can be for example suspended in a liquid (e.g. to be sprayed); g) Dust compositions, which are applied dry. They include the active ingredient(s) as solid, e.g. finely ground, optionally mixed with other powders, such as talc, etc.; h) Granules, which are made of dry, porous material to which the active ingredients have been applied. Often granule compositions are applied to the soil, but they can also be applied to the plants; i) Wettable powders, which are dry, powdered compositions. In contrast to Dust compositions, wetting agents and/or dispersing agents are present in the composition. Often they contain higher concentrations of active ingredients than Dust compositions, e.g. 15%-95% active ingredient; j) Soluble powders, which are similar to wettable powders, but dissolve completely in solution; k) Dry flowables, which look like granules, but are used in the same way as wettable powders.

Zingiberenes made from host cells and plants generated as described herein can therefore be used in fragrances, insect repellents and/or insecticides. Thus, one embodiment of the invention is a composition that includes one or more volatile hydrocarbon compounds isolated from a recombinant plant that has been modified to contain the zingiberene synthase nucleic acids described herein (e.g., any with SEQ ID NO:1, 3, 5, 7, 13, 15, 17, 19, or a nucleic acid that hybridizes to a nucleic acid with any of SEQ ID NO:1, 3, 5, 7, 13, 15, 17, 19 and, when incorporated into a plant or bacterial cell can synthesize a zingiberene).

A composition containing volatile hydrocarbon compounds such as zingiberene is suitable for repelling insect pests, such as whiteflies and thrips. The compositions are also suitable for controlling plant insect pests, in particular sap-sucking insects of the suborder *Sternorrhyncha*. Insects of the suborder *Stemorrhyncha* include psyllids, whiteflies, aphids, mealybugs and scale insects and share a common property, namely the utilization of plant sap as their food source. Other plant insect pests which can be controlled are thrips, mites (e.g. spider mites) and leaf hoppers. In some embodiments, the methods and compositions are useful for controlling whitefly infestation and whitefly damage of crop plants. In other embodiments, the compounds and/or compositions can be used for repelling insects of the family Culicidae, especially species belonging to the genera *Anopheles* (of which about 400 species exist, 30-40 of which transmit malaria, such as the species of the *A. gambiae* complex), *Culex* and/or *Aedes*. Also members of the family Ceratopogonidae, biting midges, can be attracted or repelled according to the invention, for examples the vertebrate blood sucking genera *Culicoides, Forcipomyia* (*Lasiohelea*), and *Leptoconops*, such as *Culicoides impunctatus* (the highland midge or Scottish biting midge).

Definitions

As used herein, "isolated" means a nucleic acid or polypeptide has been removed from its natural or native cell. Thus, the nucleic acid or polypeptide that is physically isolated from its natural or native cell need not be purified. Instead, the nucleic acid or polypeptide that is physically isolated from its natural or native cell can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, mutated and/or amplified.

The following Examples illustrate certain experiments performed during development of the invention.

EXAMPLE 1

Solanum habrochaites Trichomes Synthesize Zingiberene

This Example describes analysis of the volatile zingiberenes synthesized by various accessions of the wild tomato species *Solanum habrochaites*. The trichomes of the wild tomato species *S. habrochaites* predominantly synthesize sesquiterpenes, rather than monoterpenes that are characteristic of the cultivated tomato *S. lycopersicum*. Approximately 80 accessions of *S. habrochaites* were evaluated to ascertain what types of volatile terpenes are synthesized in the trichomes of these plants. One accession of *S. habrochaites* was identified that synthesizes significant quantities of zingiberene: LA2167.

Plant Material and Growth Conditions

Seeds from 80 accessions of *Solanum habrochaites*, together with a single accession of *Solanum lycopersicum* cv. M82 (LA3475) were obtained from the C. M. Rick Tomato Genetics Resource Center (see website at tgrc.ucdavis.edu/). Plants were grown in Jiffy-7 Peat Pellets (Hummert International, Earth City, Mo.) for 3 weeks in a growth chamber maintained for 16 h at 28° C. in the light (300 µE m$^{-2}$ sec$^{-1}$, mixed cool white and incandescent light bulbs) and 8 h at 20° C. in the dark.

Metabolite Extraction and Terpene Analysis

Three-week old plants were used for the chemical analysis. Briefly, a leaflet from the second newly emerging leaf was dipped in 1 mL of MTBE with 5 ng/µL of tetradecane as internal standard, and allowed to rock for 1 min. GC-MS analysis was performed as described by Schilmiller et al. (Proc Natl Acad Sci USA 106, 10865-10870 (2009)). The resulting relative abundances for each terpene in a sample were normalized to the amount of internal standard and leaflet dry weight. Terpene identification was based on comparison of mass spectra and retention times with those of authentic standards and by comparison with mass spectra from an essential oil library (Adams, IDENTIFICATION OF ESSENTIAL OIL COMPONENTS BY GAS CHROMATOGRAPHY/MASS SPECTROMETRY (Carik Stream: Allured books, 2009). Compounds were quantified based on their abundance relative to the internal standard (tetradecane) and by using standard curves of caryophyllene E and γ-terpinene.

Figure 1B:
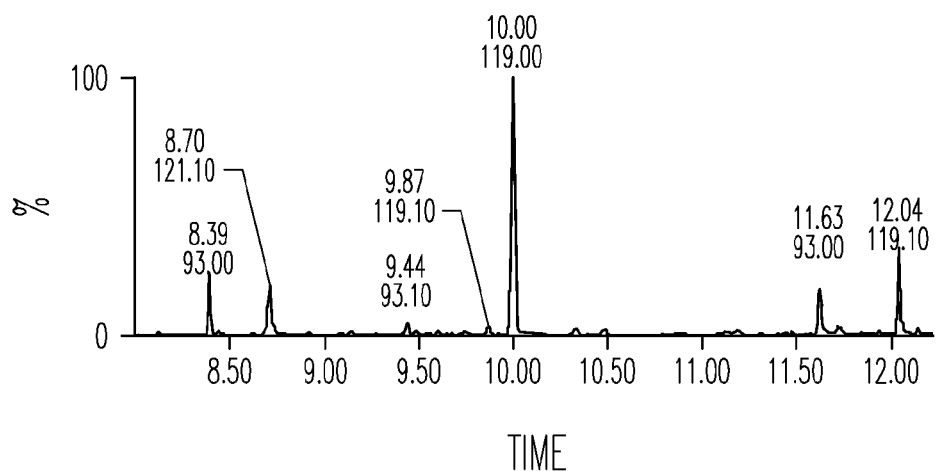

Results:

As shown in FIG. 1, *Solanum habrochaites* accession LA2167 leaf dip extracts contain a major peak eluting at about 10 minutes. The ion fragmentation pattern of the material in the 10 minute peak was substantially identical to the ion fragmentation pattern of a known sample of zingiberene (FIG. 2).

EXAMPLE 2

Isolation of *Solanum habrochaites* Zingiberene-Synthesizing Genes

This Example describes the isolation of cDNAs from *Solanum habrochaites* that encode enzymes that synthesize zingiberene.

Trichome Isolation and Gene Cloning

Greenhouse-grown plants were used for RNA collection. Stems and petioles from 2-3 fully grown plants from the same accession were pooled. Total trichomes were collected by fast-freezing the tissue and scraping the frozen trichomes in liquid nitrogen. Trichomes were ground before RNA isolation with the RNeasy kit (QIAGEN Inc. Valencia, Calif.). RNA quantity and quality were assessed with a ND-1000 Spectrophotometer. Complementary DNA was prepared with the Transcriptor First Strand cDNA Synthesis Kit (Roche Applied Science, Indianapolis, Ind.) using oligo (dT) as a primer. For cloning of PHS 1 orthologs from *S. habrochaites*, the same primers used for amplification of the full length cDNA in *S. lycopersicum* were used (see, Schilmiller et al., Proc Natl Acad Sci USA 106, 10865-10870 (2009)). These primers aligned without mismatches to the reported SBS sequences of *S. habrochaites* LA1777 (see, Sallaud et al., Plant Cell 21, 301-317 (2009)). cDNA fragments were amplified using either Pfu ultra DNA polymerase (Agilent Technologies, Santa Clara, Calif.) or KOD DNA polymerase (EMD4Biosciences, Rockland, Mass.). PCR fragments were purified using the Wizard® SV Gel and PCR Clean-Up System (Promega Corporation, Madison, Wis.) and cloned into the pCR®4Blunt-TOPO® vector (Invitrogen Corporation, Carlsbad, Calif.) using manufacturers protocols. Recombinant clones were verified by PCR colony screening followed by DNA sequence analysis.

Synthesis of Codon Optimized Genes, Recombinant Protein Expression and Activity Assays A codon optimized version of LA2167-ZIS lacking the chloroplast targeting sequence but containing BamHI and SalI restriction enzyme recognition sequences at the 5' and 3' ends respectively, was synthesized by Genscript Corporation. The synthetic gene was excised from the pUC57 cloning vector by digestion with BamHI and SalI and ligated into the pHIS8 vector previously linearized by digestion with the same enzymes. Recombinant clones were transformed into *E. coli* BL21 cells. A 5-mL log-phase culture of *E. coli* BL21 cells containing the expression vector was induced by addition of IPTG to a final concentration of 0.1 mM. The induced cells were incubated with agitation at 25° C. for 16 h, and then harvested by centrifugation at 10,000 g for 15 min. The cell pellet was resuspended in 1 mL extraction buffer (50 mM HEPES pH 8, 5% glycerol, 100 mM KCl, 7.5 mM MgCl$_2$ containing 1 mM dithiothreitol (DTT)) prior to sonication. Soluble proteins were harvested after centrifugation at 10,000 g for 20 min. The supernatant was used for subsequent enzyme assays.

Two micrograms of soluble protein were mixed with 10 µM of substrate (GPP, NPP, EE-FPP or 2Z, 6Z-FPP (Echelon Biosciences Inc., Salt Lake City, Utah)) in a 2-mL glass vial. Reactions were allowed to proceed for 30 min at 30° C., and the glass vial headspace was collected with a 65 µm polydimethylsiloxane-divinylbenzene solid-phase microextraction fiber (Supelco, Bellefonte, Pa.). After 5 min of exposure at 42° C., the SPME fiber was retracted and transferred to the GC injector port for desorption at 200° C. onto the GC column for 3 min. The terpenes were separated on a DB5 column (10 m length, inner diameter and 0.25 um). The GC-MS analysis was performed as described previously Schilmiller et al. (Plant Physiol 153, 1212-1223 (2010)).

Results cDNA clones from three accessions of *S. habrochaites* were identified that synthesize significant quantities of zingiberene. The sesquiterpene synthase from *Solanum habrochaites* accession LA2167, and the gene that encodes it, have been named LA2167-ZIS. The LA2167-ZIS enzyme is encoded by a nucleic acid with the following sequence (SEQ ID NO:1; FIG. 3A), where the bold and underlined codons are the start and stop codons.

```
   1 ATGATAGTTG GCTATAGAAG CACAATCATA ACCCTTTCTC
  41 ATCCTAAGCT AGGCAATGGG AAAACAATTT CATCCAATGC
  81 AATTTTCCGG AGATCATGTA GAGTAAGATG CAGCCACAGT
 121 ACCCCTTCAT CAATGAATGG TTTCGAAGAT GCAAGGGATA
 161 GAATAAGGGA AAGTTTTGGG AAAGTAGAGT TATCTCCTTC
 201 TTCCTATGAC ACAGCATGGG TAGCTATGGT CCCTTCAAAA
 241 CATTCACTAA ATGAGCCATG TTTTCCACAA TGTTTGGATT
 281 GGATTATTGA AAATCAAAGA GAAGATGGAT CTTGGGGACT
 321 AAACCCTAGC CATCCATTGC TTCTTAAGGA CTCACTTTCT
 361 TCCACTCTTG CATGTTTGCT TGCACTAACC AAATGGAGAG
 401 TTGGAGATGA GCAAATCAAA AGAGGCCTTG GCTTTATTGA
 441 AACCCAGAGT TGGGCAATTG ATAACAAGGA TCAAATTTCA
 481 CCTCTAGGAT TTGAAATTAT ATTTCCCAGT ATGATCAAGT
 521 CTGCAGAAAA ACTAAACTTA AATCTAGCAA TTAACAAAAG
 561 AGATTCAACA ATTAAAAGAG CATTACAGAA TGAGTTCACG
 601 AGGAATATTG AATATATGAG TGAAGGATTT GGTGAATTAT
 641 GTGATTGGAA GGAAATAATA AAGTTACATC AAAGGCAAAA
 681 TGGTTCATTA TTTGATTCAC CAGCCACTAC TGCAGCTGCC
 721 TTGATTTACC ATCAGCATGA TAAAAAATGC TATGAATATC
 761 TTAATTCAAT CTTGCAACAA CACAAAAATT GGGTTCCCAC
 801 TATGTATCCA ACAAAGATAC ATTCATTGCT TTGCTTGGTT
 841 GATACACTTC AAAATCTTGG AGTACATCGG CATTTAAAT
 881 CAGAAATAAA GAAAGCCCTA GATGAAATAT ACAGGCTATG
 921 GCAACAAAAG AATGAAGAAA TTTTCTCAAA TGTCACCCAT
 961 TGTGCTATGG CTTTTCGACT TCTAAGGATA AGCTACTATG
1001 ATGTCTCCTC AGATGAACTA GCAGAATTTG TGGATGAAGA
1041 ACATTTCTTT GCAACAAGTG GGAAATATAC AAGTCATGTT
1081 GAAATTCTTG AACTCCACAA AGCATCACAA TTGGCTATTG
1121 ATCATGAGAA AGATGACATT TTGGATAAGA TTAACAATTG
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACA TTTTAAAATC
1321 TTAAAAGCAG CTTATAGGTC ACCTAACATT AACAATAAGG
1361 ACTTGTTTAT ATTTTCAATA CGCGACTTTG AATTATGCCA
1401 AGCTCAACAC CAAGAAGAAC TTCAACAACT CAAGAGGTGG
1441 TTTGAAGATT GTAGATTGGA CCAACTCGGA CTTTCGGAAC
1481 AATTTATATC TGCTAGTTAC TTATGTGCTA TTCCTATTGT
1521 CCCCGGGCCT GAATTATCCG ATGCTCGTCT CGTGTACGCG
1561 AAATACGTCA TGCTCTTGAC TATTGTCGAT GATCATTTCG
1601 AGAGTTTTGC ATCTACAGAT GAATGTCTCA ACATCATTGA
1641 ATTAGTAGAA AGGTGGGATG ACTATGCAAG TGTAGGTTAT
1681 AAATCTGAGA GGGTTAAAGT TTTATTTTCA ATGTTTTACA
1721 AATCAATAGA GGAGATTGCA ACAATTGCTG AAATTAAACA
1761 AGGACGATCT GTCAAAAATC ACCTTATTAA TTTGTGGCTT
1801 AAAGTGATGA AGTTGATGTT GATGGAACGA GTAGAGTGGT
1841 GTTCTGGCAA GACAATACCA AGAATAGAAG AGTATTTGTA
1881 TGTTAGTTCT ATAACATTTG GTTCAAGATT GATTCCTCTC
1921 ACAACACAAT ATTTTATTGG AATAAAAATA TCCAAAGATC
1961 TTTTAGAAAG TGATGAAATT TATGGTTTAT GCAATTTTAC
2001 CGGTATAGTC TTGAGGCTCC TCAATGATTT ACAAGATTCC
2041 AAGAGAGAAC AAAAGGAGGG CTCAATAAAT TTAGTCACAT
2081 TACTAATGAA AAGTATCTCT GAGGAAGAAG CTATAATGAA
2121 GATGAAGGAA ATCTTGGAAA TGAAAAGAAG AGAGTTATTT
2161 AAAATGGTTT TAGTTCAAAA AAAGGGAAGC CAATTGCCTC
2201 AATTATGCAA AGAAATATTT TGGAGGACAT GCAAATGGGC
2241 TCATTTCACT TATTCACAAA CTGATAGATA TAGATTTCCA
2281 GAGGAAATGG AGAATCACAT TGATGAAGTC TTTTACAAAC
2321 CACTCAATCA TTAA
```

The SEQ ID NO:1 nucleotide sequence encodes the following LA2167-ZIS amino acid sequence (FIG. 3B, SEQ ID NO:6).

```
   1 MIVGYRSTII TLSHPKLGNG KTISSNAIFR RSCRVRCSHS
  41 TPSSMNGFED ARDRIRESFG KVELSPSSYD TAWVAMVPSK
  81 HSLNEPCFPQ CLDWIIENQR EDGSWGLNPS HPLLLKDSLS
 121 STLACLLALT KWRVGDEQIK RGLGFIETQS WAIDNKDQIS
 161 PLGFEIIFPS MIKSAEKLNL NLAINKRDST IKRALQNEFT
 201 RNIEYMSEGF GELCDWKEII KLHQRQNGSL FDSPATTAAA
 241 LIYHQHDKKC YEYLNSILQQ HKNWVPTMYP TKIHSLLCLV
 281 DTLQNLGVHR HFKSEIKKAL DEIYRLWQQK NEEIFSNVTH
 321 CAMAFRLLRI SYYDVSSDEL AEFVDEEHFF ATSGKYTSHV
 361 EILELHKASQ LAIDHEKDDI LDKINNWTRT FMEQKLLNNG
 401 FIDRMSKKEV ELALRNFYII SDLAENRRYI KSYEENNFKI
 441 LKAAYRSPNI NNKDLFIFSI RDFELCQAQH QEELQQLKRW
```

```
481 FEDCRLDQLG LSEQFISASY LCAIPIVPGP ELSDARLVYA
521 KYVMLLTIVD DHFESFASTD ECLNIIELVE RWDDYASVGY
561 KSERVKVLFS MFYKSIEEIA TIAEIKQGRS VKNHL1NLWL
601 KVMKLMLMER VEWCSGKTIP RIEEYLYVSS ITFGSRLIPL
641 TTQYFIGIKI SKDLLESDEI YGLCNFTGIV LRLLNDLQDS
681 KREQKEGSIN LVTLLMKSIS EEEAIMKMKE ILEMKRRELF
721 KMVLVQKKGS QLPQLCKEIF WRTCKWAHFT YSQTDRYRFP
761 EEMENHIDEV FYKPLNH
```

Figure 4A:
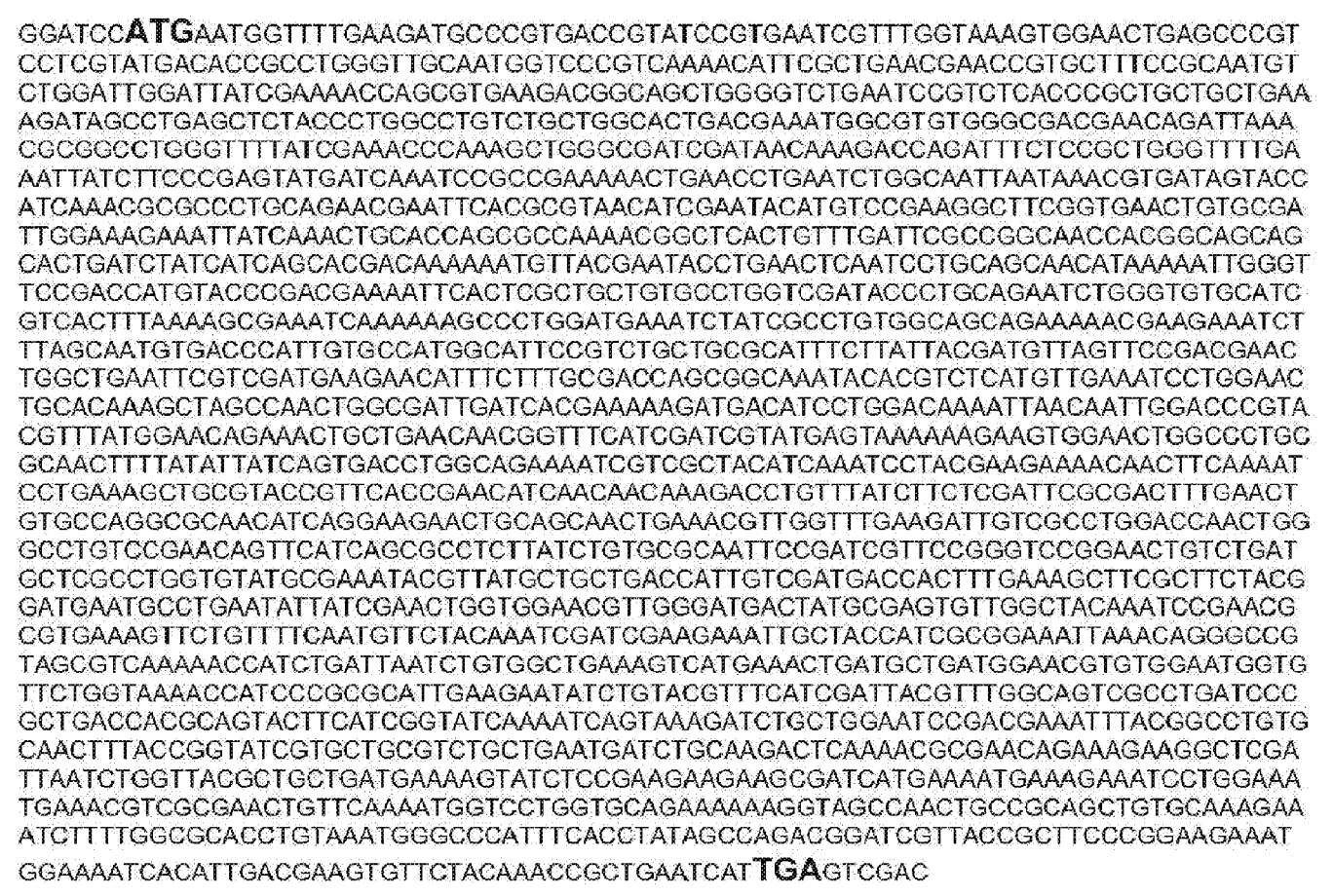

A codon optimized version of LA2167-ZIS open reading frame that lacks the predicted chloroplast targeting sequence from the N'-terminus was generated for expression in *E. coli*. The nucleotide sequence of this codon-optimized sequence is shown below as SEQ ID NO:3 (FIG. 4A), where the bold and underlined codons are the start and stop codons.

```
   1 GGATCcATGA ATGGTTTTGA AGATGCCCGT GACCGTATCC
  41 GTGAATCGTT TGGTAAAGTG AACTGAGCC CGTCCTCGTA
  81 TGACACCGCC TGGGTTGCAA TGGTCCCGTC AAAACATTCG
 121 CTGAACGAAC CGTGCTTTCC GCAATGTCTG GATTGGATTA
 161 TCGAAAACCA GCGTGAAGAC GGCAGCTGGG GTCTGAATCC
 201 GTCTCACCCG CTGCTGCTGA AAGATAGCCT GAGCTCTACC
 241 CTGGCCTGTC TGCTGGCACT GACGAAATGG CGTGTGGGCG
 281 ACGAACAGAT TAAACGCGGC CTGGGTTTTA TCGAAACCCA
 321 AAGCTGGGCG ATCGATAACA AGACCAGAT TTCTCCGCTG
 361 GGTTTTGAAA TTATCTTCCC GAGTATGATC AAATCCGCCG
 401 AAAAACTGAA CCTGAATCTG GCAATTAATA AACGTGATAG
 441 TACCATCAAA CGCGCCCTGC AGAACGAATT CACGCGTAAC
 481 ATCGAATACA TGTCCGAAGG CTTCGGTGAA CTGTGCGATT
 521 GGAAAGAAAT TATCAAACTG CACCAGCGCC AAAACGGCTC
 561 ACTGTTTGAT TCGCCGGCAA CCACGGCAGC AGCACTGATC
 601 TATCATCAGC ACGACAAAAA ATGTTACGAA TACCTGAACT
 641 CAATCCTGCA GCAACATAAA AATTGGGTTC CGACCATGTA
 681 CCCGACGAAA ATTCACTCGC TGCTGTGCCT GGTCGATACC
 721 CTGCAGAATC TGGGTGTGCA TCGTCACTTT AAAAGCGAAA
 761 TCAAAAAGC CCTGGATGAA ATCTATCGCC TGTGGCAGCA
 801 GAAAAACGAA GAAATCTTTA GCAATGTGAC CCATTGTGCC
 841 ATGGCATTCC GTCTGCTGCG CATTTCTTAT TACGATGTTA
 881 GTTCCGACGA ACTGGCTGAA TTCGTCGATG AAGAACATTT
 921 CTTTGCGACC AGCGGCAAAT ACACGTCTCA TGTTGAAATC
 961 CTGGAACTGC ACAAAGCTAG CCAACTGGCG ATTGATCACG
1001 AAAAAGATGA CATCCTGGAC AAAATTAACA ATTGGACCCG
1041 TACGTTTATG GAACAGAAAC TGCTGAACAA CGGTTTCATC
1081 GATCGTATGA GTAAAAAAGA AGTGGAACTG GCCCTGCGCA
1121 ACTTTTATAT TATCAGTGAC CTGGCAGAAA ATCGTCGCTA
1161 CATCAAATCC TACGAAGAAA ACAACTTCAA AATCCTGAAA
1201 GCTGCGTACC GTTCACCGAA CATCAACAAC AAAGACCTGT
1241 TTATCTTCTC GATTCGCGAC TTTGAACTGT GCCAGGCGCA
1281 ACATCAGGAA GAACTGCAGC AACTGAAACG TTGGTTTGAA
1321 GATTGTCGCC TGGACCAACT GGGCCTGTCC GAACAGTTCA
1361 TCAGCGCCTC TTATCTGTGC GCAATTCCGA TCGTTCCGGG
1401 TCCGGAACTG TCTGATGCTC GCCTGGTGTA TGCGAAATAC
1441 GTTATGCTGC TGACCATTGT CGATGACCAC TTTGAAAGCT
1481 TCGCTTCTAC GGATGAATGC CTGAATATTA TCGAACTGGT
1521 GGAACGTTGG GATGACTATG CGAGTGTTGG CTACAAATCC
1561 GAACGCGTGA AAGTTCTGTT TTCAATGTTC TACAAATCGA
1601 TCGAAGAAAT TGCTACCATC GCGGAAATTA AACAGGGCCG
1641 TAGCGTCAAA AACCATCTGA TTAATCTGTG GCTGAAAGTC
1681 ATGAAACTGA TGCTGATGGA ACGTGTGGAA TGGTGTTCTG
1721 GTAAAACCAT CCCGCGCATT GAAGAATATC TGTACGTTTC
1761 ATCGATTACG TTTGGCAGTC GCCTGATCCC GCTGACCACG
1801 CAGTACTTCA TCGGTATCAA AATCAGTAAA GATCTGCTGG
1841 AATCCGACGA AATTTACGGC CTGTGCAACT TTACCGGTAT
1881 CGTGCTGCGT CTGCTGAATG ATCTGCAAGA CTCAAAACGC
1921 GAACAGAAAG AAGGCTCGAT TAATCTGGTT ACGCTGCTGA
1961 TGAAAAGTAT CTCCGAAGAA GAAGCGATCA TGAAAATGAA
2001 AGAAATCCTG GAAATGAAAC GTCGCGAACT GTTCAAAATG
2041 GTCCTGGTGC AGAAAAAAGG TAGCCAACTG CCGCAGCTGT
2081 GCAAAGAAAT CTTTTGGCGC ACCTGTAAAT GGGCCCATTT
2121 CACCTATAGC CAGACGGATC GTTACCGCTT CCCGGAAGAA
2161 ATGGAAAATC ACATTGACGA AGTGTTCTAC AAACCGCTGA
2201 ATTGAGT CGAC
```

The SEQ ID NO:3 nucleotide sequence encodes the following LA2167-ZIS 'codon optimized' amino acid sequence that lacks a chloroplast transit sequence (SEQ ID NO:4; FIG. 4B).

```
 1 MNGFEDARDR IRESFGKVEL SPSSYDTAWV AMVPSKHSLN
41 EPCFPQCLDW IIENQREDGS WGLNPSHPLL LKDSLSSTLA
81 CLLALTKWRV GDEQIKRGLG FIETQSWAID NKDQISPLGF
```

```
121 EIIFPSMIKS AEKLNLNLAI NKRDSTIKRA LQNEFTRNIE
161 YMSEGFGELC DWKEIIKLHQ RQNGSLFDSP ATTAAALIYH
201 QHDKKCYEYL NSILQQHKNW VPTMYPTKIH SLLCLVDTLQ
241 NLGVHRHFKS EIKKALDEIY RLWQQKNEEI FSNVTHCAMA
281 FRLLRISYYD VSSDELAEFV DEEHFFATSG KYTSHVEILE
321 LHKASQLAID HEKDDILDKI NNWTRTFMEQ KLLNNGFIDR
361 MSKKEVELAL RNFYIISDLA ENRRYIKSYE ENNFKILKAA
401 YRSPNINNKD LFIFSIRDFE LCQAQHQEEL QQLKRWFEDC
441 RLDQLGLSEQ FISASYLCAI PIVPGPELSD ARLVYAKYVM
481 LLTIVDDHFE SFASTDECLN IIELVERWDD YASVGYKSER
521 VKVLFSMFYK SIEEIATIAE IKQGRSVKNH LINLWLKVMK
561 LMLMERVEWC SGKTIPRIEE YLYVSSITFG SRLIPLTTQY
601 FIGIKISKDL LESDEIYGLC NFTGIVLRLL NDLQDSKREQ
641 KEGSINLVTL LMKSISEEEA IMKMKEILEM KRRELFKMVL
681 VQKKGSQLPQ LCKEIFWRTC KWAHFTYSQT DRYRFPEEME
721 NHIDEVFYKP LNH
```

The LA2167-ZIS 'codon optimized' enzyme with SEQ ID NO:4 can also be used or synthesized without an N-terminal methionine. Such a amino acid sequence that lacks the N-terminal methionine can have the following sequence (SEQ ID NO:11).

```
  2 NGFEDARDR IRESFGKVEL SPSSYDTAWV AMVPSKHSLN
 41 EPCFPQCLDW IIENQREDGS WGLNPSHPLL LKDSLSSTLA
 81 CLLALTKWRV GDEQIKRGLG FIETQSWAID NKDQISPLGF
121 EIIFPSMIKS AEKLNLNLAI NKRDSTIKRA LQNEFTRNIE
161 YMSEGFGELC DWKEIIKLHQ RQNGSLFDSP ATTAAALIYH
201 QHDKKCYEYL NSILQQHKNW VPTMYPTKIH SLLCLVDTLQ
241 NLGVHRHFKS EIKKALDEIY RLWQQKNEEI FSNVTHCAMA
281 FRLLRISYYD VSSDELAEFV DEEHFFATSG KYTSHVEILE
321 LHKASQLAID HEKDDILDKI NNWTRTFMEQ KLLNNGFIDR
361 MSKKEVELAL RNFYIISDLA ENRRYIKSYE ENNFKILKAA
401 YRSPNINNKD LFIFSIRDFE LCQAQHQEEL QQLKRWFEDC
441 RLDQLGLSEQ FISASYLCAI PIVPGPELSD ARLVYAKYVM
481 LLTIVDDHFE SFASTDECLN IIELVERWDD YASVGYKSER
521 VKVLFSMFYK SIEEIATIAE IKQGRSVKNH LINLWLKVMK
561 LMLMERVEWC SGKTIPRIEE YLYVSSITFG SRLIPLTTQY
601 FIGIKISKDL LESDEIYGLC NFTGIVLRLL NDLQDSKREQ
641 KEGSINLVTL LMKSISEEEA IMKMKEILEM KRRELFKMVL
681 VQKKGSQLPQ LCKEIFWRTC KWAHFTYSQT DRYRFPEEME
721 NHIDEVFYKP LNH
```

A nucleic acid with the codon-optimized SEQ ID NO:3 open reading frame was cloned into an expression vector pHIS8 and expressed in *E. coli* BL21 DE3 cells. Induced *E. coli* cell cultures were supplied with the substrate 2Z,6Z-Farnesyl diphosphate. Several sesquiterpenes were synthesized in these cultures (FIG. 6) and zingiberene constituted greater than 95% of the products that were obtained, as illustrated in the following Table 1 (see also FIG. 7).

TABLE 1

| Peak # | Compound | Quality of Match to Library | Retention time | Peak Height | Peak Area | Peak Area % |
|---|---|---|---|---|---|---|
| 1 | bergamotene | 50 | 4.488 | 7761 | 156.27 | 0.273 |
| 2 | AR-curcumene | 98 | 4.623 | 38198 | 564.736 | 0.986 |
| 3 | α-zingiberene | 94 | 4.667 | 4143568 | 56020.18 | 97.839 |
| 4 | Bisabolene beta | 60 | 4.714 | 4306 | 61.219 | 0.107 |
| 5 | Sesquiphellandrene beta | 96 | 4.769 | 25093 | 324.618 | 0.567 |
| 6 | Sesquilavandulol <Z> | 86 | 5.191 | 9029 | 130.73 | 0.228 |

Comparison of the ion fragmentation pattern of the sesquiterpene synthesized by the recombinant LA2167-ZIS enzyme (FIG. 8A) with the ion fragmentation pattern for zingiberene obtained from a library of reference compounds (FIG. 8B) demonstrated that the LA2167-ZIS enzyme makes zingiberene.

Furthermore, upon supplying either neryl diphosphate (NPP) or geranyl diphosphate (GPP) as substrates, LA2167-ZIS failed to synthesize any products (FIG. 5). These data indicate that the LA2167-ZIS enzyme is a sesquiterpene synthase that has specificity for a C15 substrate rather than for C10 substrates.

Figure 9A:
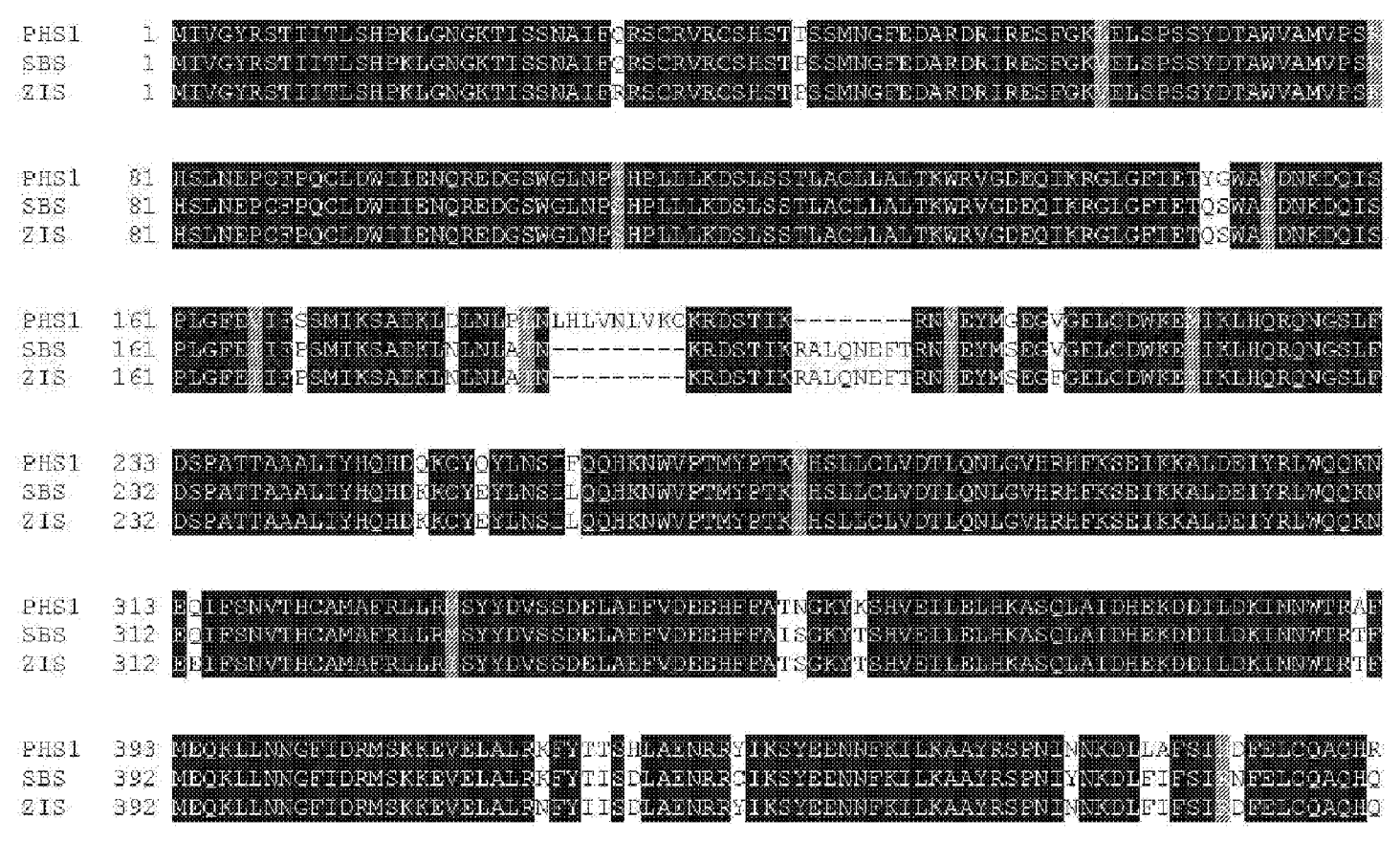
Figure 9B:
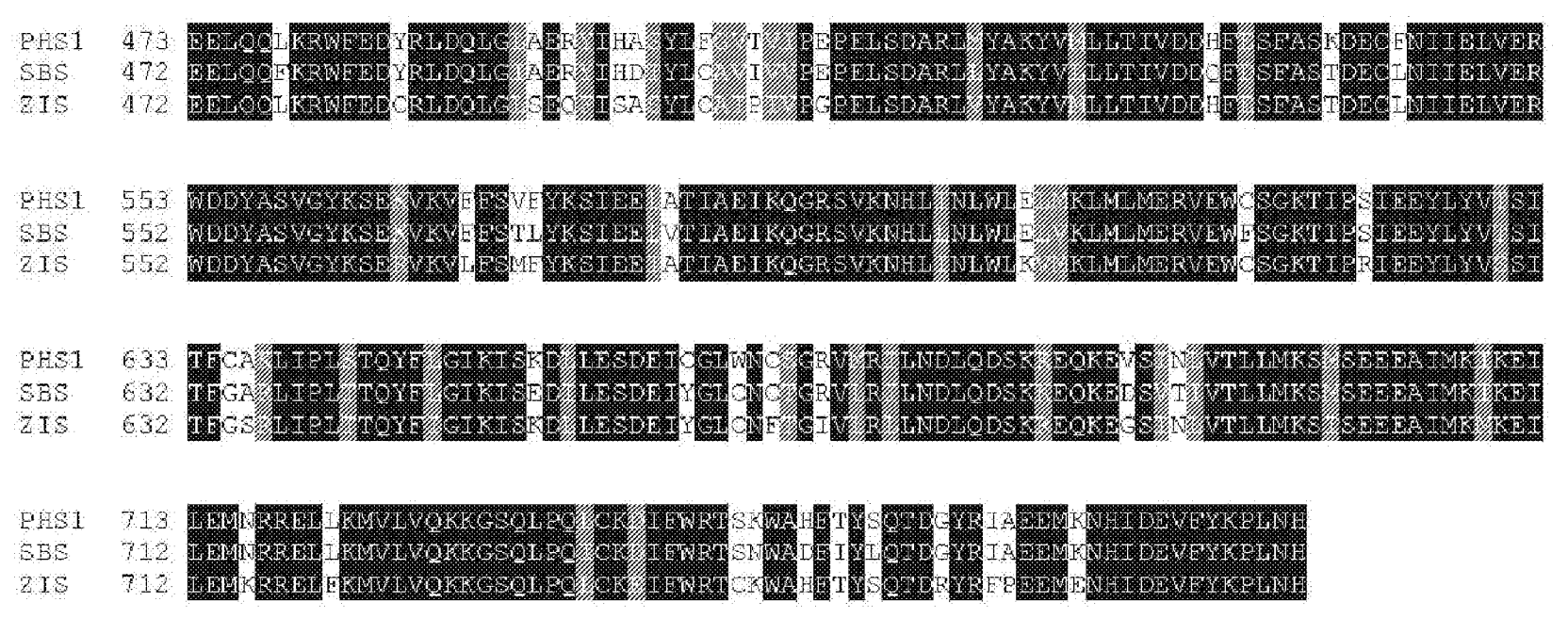
Figure 9C:
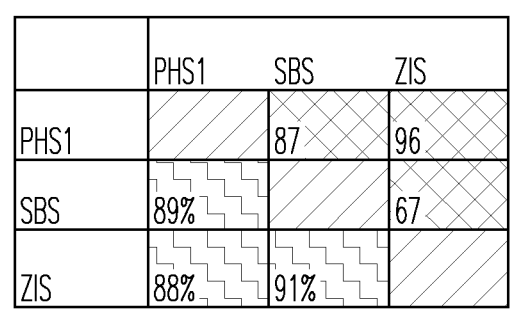

FIG. 9A-B illustrates the differences in sequence of two terpene synthases compared to the LA2167-ZIS synthase described herein. In particular, the sequences of the phellandrene synthase (PHS1) (Schilmiller et al., Proc Natl Acad Sci USA 106, 10865-10870 (2009)), the santalene and bergamotene synthase (SBS) (Sallaud et al., Plant Cell 21, 301-317 (2009)), are shown in juxtaposition to the LA2167-ZIS zingiberene synthase (ZIS).

EXAMPLE 3

Isolation of Other *Solanum habrochaites* Zingiberene-Synthase Genes

This Example describes the isolation of additional cDNAs from *Solanum habrochaites* that encode zingiberene synthase enzymes.

Procedures like those described in the foregoing Examples were used for isolation of zingiberene synthase cDNAs from *Solanum habrochaites* accessions LA1731, LA2196, LA2106 and LA1352.

The *Solanum habrochaites* accession LA1731 zingiberene synthase has the following amino acid sequence (SEQ ID NO:12).

```
  1 MIVGYRSTII TLSHPKLGNG KTISSNAIFR RSCRVRCSHS
 41 TPSSMNGFED ARDRIRESFG KVELSPSSYD TAWVAMVPSK
 81 HSLNEPCFPQ CLDWIIENQR EDGSWGLNPS HPLLLKDSLS
121 STLACLLALT KWRVGDEQIK RGLGFIETQS WAIDNKDQIS
161 PLGFEIIFPS MIKSAEKLNL NLAINKRDST IKRALQNEFT
201 RNIEYMSEGF GELCDWKEIM KLHQRQNGSL FDSPATTAAA
241 LIYHQHDKKC YEYLNSILQQ HKNWVPTMYP TKIHSLLCLV
281 DTLQNLGVHR HFKSEIKKAL DEIYRLWQQK NEEIFSNVTH
321 CAMVFRLLRI SYYDVSSDEL AEFVDEEHFF ATSGKYTSHV
361 EILELHKASQ LAIDHEKDDI LDKINNWTRT FMEQKLLNNG
401 FIDRMSKKEV ELALRNFYII SDLAENRRYI KSYEENNFKI
441 LKAAYRSPNI NNKDLFIFSI RDFELCQAQH QEELQQLKRW
481 FEDCRLDQLG LSEQFISASY LCAIPIVPGP ELSDARLVYA
521 KYVMLLTIVD DHFESFASTD ECLNIIELVE RWDDYASVGY
561 KSERVKVLFS MFYKSIEEIA TIAEIKQGRS VKNHLINLWL
601 KVMKLMLMER VEWCSGKTIP RIEEYLYVSS ITFGSRLIPL
641 TTQYFLGIKI SKDLLESDEI YGLCNFTGIV LRLLNDLQDS
681 KREQKEGSIN LVTLLMKSIS EEEAIMKMKE ILEMKRRELF
721 KMVLVQKKGS QLPQLCKEIF WRTCKWAHFT YSQTDRYRFP
761 EEMENHIDEV FYKPLNH
```

The *Solanum habrochaites* accession LA1731 zingiberene synthase enzyme with the foregoing amino acid sequence SEQ ID NO:12 is encoded by the following nucleotide sequence (SEQ ID NO:13).

```
   1 ATGATAGTTG GCTATAGAAG CACAATCATA ACCCTTTCTC
  41 ATCCTAAGCT AGGCAATGGG AAAACAATTT CATCCAATGC
  81 AATTTTCCGG AGATCATGTA GAGTAAGATG CAGCCACAGT
 121 ACCCCTTCAT CAATGAATGG TTTTGAAGAT GCAAGGGATA
 161 GAATAAGGGA AAGTTTTGGG AAAGTAGAGT TATCTCCTTC
 201 TTCCTATGAC ACAGCATGGG TAGCTATGGT CCCTTCAAAA
 241 CATTCACTAA ATGAGCCATG TTTTCCACAA TGTTTGGATT
 281 GGATTATTGA AAATCAAAGA GAAGATGGAT CTTGGGGACT
 321 AAACCCTAGC CATCCATTGC TTCTCAAGGA CTCACTTTCT
 361 TCCACTCTTG CATGTTTGCT TGCACTAACC AAATGGAGAG
 401 TTGGAGATGA GCAAATCAAA AGAGGCCTTG GCTTTATTGA
 441 AACCCAGAGT TGGGCAATTG ATAACAAGGA TCAAATTTCA
 481 CCTCTAGGAT TTGAAATTAT ATTTCCCAGT ATGATCAAGT
 521 CTGCAGAAAA ACTAAACTTA AATCTAGCAA TTAACAAAAG
 561 AGATTCAACA ATTAAAAGAG CATTACAGAA TGAGTTCACG
 601 AGGAATATTG AATATATGAG TGAAGGATTT GGTGAATTAT
 641 GTGATTGGAA GGAAATAATG AAGTTACATC AAAGGCAAAA
 681 TGGTTCATTA TTTGATTCAC CAGCCACTAC TGCAGCTGCC
 721 TTGATTTACC ATCAGCATGA TAAAAAATGC TATGAATATC
 761 TTAATTCAAT CTTGCAACAA CACAAAAATT GGGTTCCCAC
 801 TATGTATCCA ACAAAGATAC ATTCATTGCT TTGCTTGGTT
 841 GATACACTTC AAAATCTTGG AGTACATCGG CATTTTAAAT
 881 CAGAAATAAA GAAAGCCCTA GATGAAATAT ACAGGCTATG
 921 GCAACAAAAG AATGAAGAAA TTTTCTCAAA TGTCACCCAT
 961 TGTGCTATGG TTTTTCGACT TCTAAGGATA AGCTACTATG
1001 ATGTCTCCTC AGATGAACTA GCAGAATTTG TGGATGAAGA
1041 ACATTTCTTT GCAACAAGTG GGAAATATAC AAGTCATGTT
1081 GAAATTCTTG AACTCCACAA AGCATCACAA TTGGCTATTG
1121 ATCATGAAAA AGATGACATT TTGGATAAGA TTAACAATTG
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACAA TTTTAAAATC
1321 TTAAAAGCAG CTTATAGGTC ACCTAACATT AACAATAAGG
```

```
1361 ACTTGTTTAT ATTTTCAATA CGCGACTTTG AATTATGCCA

1401 AGCTCAACAC CAAGAAGAAC TTCAACAACT CAAGAGGTGG

1441 TTTGAAGATT GTAGATTGGA CCAACTCGGA CTTTCGGAAC

1481 AATTTATATC TGCTAGTTAC TTATGTGCTA TTCCTATTGT

1521 CCCCGGGCCT GAATTATCCG ATGCTCGTCT CGTGTACGCG

1561 AAATACGTCA TGCTCTTGAC TATTGTCGAT GATCATTTCG

1601 AGAGTTTTGC ATCTACAGAT GAATGTCTCA ACATCATTGA

1641 ATTAGTAGAA AGGTGGGATG ACTATGCAAG TGTAGGTTAT

1681 AAATCTGAGA GGGTTAAAGT TTTATTTTCA ATGTTTTACA

1721 AATCAATAGA GGAGATTGCA ACAATTGCTG AAATTAAACA

1761 AGGACGATCT GTCAAAAATC ACCTTATTAA TTTGTGGCTT

1801 AAAGTGATGA AGTTGATGTT GATGGAACGA GTAGAGTGGT

1841 GTTCTGGCAA GACAATACCA AGAATAGAAG AGTATTTGTA

1881 TGTTAGTTCT ATAACATTTG GTTCAAGATT GATTCCTCTC

1921 ACAACACAAT ATTTTCTTGG AATAAAAATA TCCAAAGATC

1961 TTTTAGAAAG TGATGAAATT TATGGTTTAT GCAATTTTAC

2001 CGGTATAGTC TTGAGGCTCC TCAATGATTT ACAAGATTCC

2041 AAGAGAGAAC AAAAGGAGGG CTCAATAAAT TTAGTCACAT

2081 TACTAATGAA AAGTATCTCT GAGGAAGAAG CTATAATGAA

2121 GATGAAGGAA ATCTTGGAAA TGAAAGAAG AGAGTTATTT

2161 AAAATGGTTT TAGTTCAAAA AAAGGGAAGC CAATTGCCTC

2201 AATTATGCAA AGAAATATTT TGGAGGACAT GCAAATGGGC

2241 TCATTTCACT TATTCACAAA CTGATAGATA TAGATTTCCA

2281 GAGGAAATGG AGAATCACAT TGATGAAGTC TTTTACAAAC

2321 CACTCAATCA TTAA
```

The *Solanum habrochaites* accession LA2196 zingiberene synthase has the following amino acid sequence (SEQ ID NO:14).

```
  1 MIVGYRSTII ILSHPKLGNG KTISSNAIFQ RSCRVRCSHS
 41 TTSSMNGFED ARDRIRESFG KLELSPSSYD TAWVAMVPSN
 81 HSLNEPCFPQ CLDWIIENQR EDGSWGLNPS HPLLLKDSLS
121 STLACLLALT KWRVGDEQIK RGLGFIETQS WAIDNKDQIS
161 PLGFEIIFPS MIKSAEKLNL NLAINKRDST IKRALQNEFT
201 RNIEYMSEGV GELCDWKEII KLHQRQNGSL FDSPATTAAA
241 LIYHQHDKKC YEYLNSILQQ HKNWVPTMYP TKIHSLLCLV
281 DTLQNLGVHR HFKSEIKKAL DEIYRLWQQK NEEIFSNVTH
321 CAMAFRLLRI SYYDVSSDEL AEFVDEEHFF ATSGKYTSHV
361 EILELHKASQ LAIDHEKDDI LDKINNWTRT FMEQKLLNNG
401 FIDRMSKKEV ELALRNFYII SDLAENRRYI KSYEENNFKI
441 LKAAYRSPNI NNKDLFIFSI RDFELCQAQH QEELQQLKRW
481 FEDCRLDQLG LSEQFISASY LCAIPIVPGP ELSDARLMYA
521 KYVMLLTIVD DHFESFASTD ECLNIIELVE RWDDYASVGY
561 KSERVKVLFS MFYKSIEEIA TIAEIKQGRS VKNHLINLWL
601 KVMKLMLMER VEWCSGKTIP RIEEYLYVTS ITFGSRLIPL
641 TTQYFLGIKI SKDLLESDEI YGLCNCTGIV LRLLNDLQDS
681 KREQKEGSIN LVTLLMKSIS EEEAIMKMKE ILEMKRRELF
721 KMVLVQKKGS QLPQLCKEIF WRTCKWAHFT YSQTDRYRFP
761 EEMENHIDEV FYKPLNH
```

The *Solanum habrochaites* accession LA2196 zingiberene synthase enzyme with the foregoing amino acid sequence SEQ ID NO:14 is encoded by the following nucleotide sequence (SEQ ID NO:15).

```
   1 ATGATAGTTG GCTATAGAAG CACAATCATA ATCCTTTCTC
  41 ATCCTAAGCT AGGCAATGGG AAAACAATTT CATCCAATGC
  81 AATTTTCCAG AGATCATGTA GAGTAAGATG CAGCCACAGT
 121 ACCACTTCAT CAATGAATGG TTTCGAAGAT GCAAGGGATA
 161 GAATAAGGGA AAGTTTTGGG AAATTAGAGT TATCTCCTTC
 201 TTCCTATGAC ACAGCATGGG TAGCTATGGT CCCTTCAAAT
 241 CATTCACTAA ATGAGCCATG TTTTCCACAA TGTTTGGATT
 281 GGATTATTGA AAATCAAAGA GAAGATGGAT CTTGGGGACT
 321 AAACCCTAGC CATCCATTGC TTCTCAAGGA CTCACTTTCT
 361 TCCACTCTTG CATGTTTGCT TGCACTAACC AAATGGAGAG
 401 TTGGAGATGA GCAAATCAAA AGAGGCCTTG GCTTTATTGA
 441 AACCCAGAGT TGGGCAATTG ATAACAAGGA TCAAATTTCA
 481 CCTCTAGGAT TTGAAATTAT ATTTCCCAGT ATGATCAAGT
 521 CTGCAGAAAA ACTAAACTTA AATCTAGCAA TTAACAAAAG
 561 AGATTCAACA ATTAAAAGAG CATTGCAGAA TGAATTCACG
 601 AGGAATATTG AATATATGAG TGAAGGAGTT GGTGAATTAT
 641 GTGATTGGAA GGAAATAATA AAGTTACATC AAAGGCAAAA
 681 TGGTTCATTA TTTGATTCAC CAGCCACTAC TGCAGCTGCC
 721 TTGATTTACC ATCAGCATGA TAAAAAATGC TATGAATATC
 761 TTAATTCAAT CTTGCAACAA CACAAAAATT GGGTTCCCAC
 801 TATGTATCCA ACAAAGATAC ATTCATTGCT TTGCTTGGTT
 841 GATACACTTC AAAATCTTGG AGTACATCGG CATTTTAAAT
 881 CAGAAATAAA GAAAGCCCTA GATGAAATAT ACAGGCTATG
 921 GCAACAAAAG AATGAAGAAA TTTTCTCAAA TGTCACCCAT
 961 TGTGCTATGG CTTTTCGACT TCTAAGGATA AGCTACTATG
1001 ATGTCTCCTC GGATGAACTA GCAGAATTTG TGGATGAAGA
1041 ACATTTTTTT GCAACAAGTG GGAAATATAC AAGTCATGTT
1081 GAAATTCTTG AACTCCACAA AGCATCACAA TTGGCTATTG
1121 ATCATGAGAA AGATGACATT TTGGATAAGA TTAACAATTG
```

```
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACAA TTTTAAAATC
1321 TTAAAAGCAG CTTATAGGTC ACCTAACATT AACAATAAGG
1361 ACTTGTTTAT ATTTCAATA CGCGACTTTG AATTATGCCA
1401 AGCTCAACAC CAAGAAGAAC TTCAACAACT CAAGAGGTGG
1441 TTTGAAGATT GTAGATTGGA CCAACTCGGA CTTTCGGAAC
1481 AATTTATATC TGCTAGTTAC TTATGTGCTA TTCCTATTGT
1521 CCCCGGGCCT GAATTATCCG ATGCTCGTCT CATGTACGCG
1561 AAATACGTCA TGCTCTTGAC TATTGTCGAT GATCATTTCG
1601 AGAGTTTTGC ATCTACAGAT GAATGTCTCA ACATCATTGA
1641 ATTAGTAGAA AGGTGGGATG ACTATGCAAG TGTAGGTTAT
1681 AAATCTGAGA GGGTTAAAGT TTTATTTTCA ATGTTTTACA
1721 AATCAATAGA GGAGATTGCA ACAATTGCTG AAATTAAACA
1761 AGGACGATCT GTCAAAAATC ACCTTATTAA TTTGTGGCTT
1801 AAAGTGATGA AGTTGATGTT GATGGAACGA GTAGAGTGGT
1841 GTTCTGGCAA GACAATACCA AGAATAGAAG AGTATTTGTA
1881 TGTTACTTCT ATAACATTTG GTTCAAGATT GATTCCTCTC
1921 ACAACACAAT ATTTTCTTGG AATAAAAATA TCCAAAGATC
1961 TTTTAGAAAG TGATGAAATT TATGGTTTAT GCAATTGTAC
2001 CGGTATAGTC TTGAGGCTCC TCAATGATTT ACAAGATTCC
2041 AAGAGAGAAC AAAAGGAGGG CTCAATAAAT TTAGTCACAT
2081 TACTAATGAA AAGTATCTCT GAGGAAGAAG CTATAATGAA
2121 GATGAAGGAA ATCTTGGAAA TGAAAAGAAG AGAGTTATTT
2161 AAAATGGTTT TAGTTCAAAA AAAGGGAAGC CAATTGCCTC
2201 AATTATGCAA AGAAATATTT TGGAGGACAT GCAAATGGGC
2241 TCATTTCACT TATTCACAAA CTGATAGATA TAGATTTCCA
2281 GAGGAAATGG AGAATACACAT TGATGAAGTC TTTTACAAAC
2321 CACTCAATCA TTAA
```

The *Solanum habrochaites* accession LA2106 zingiberene synthase has the following amino acid sequence (SEQ ID NO:16).

```
  1 MIVGYRSTII ILSHPKLGNG KTISSNAIFQ RSCRVRCSHS
 41 TTSSMNGFED ARDRIRESFG KLELSPSSYD TAWVAMVPSK
 81 HSLNEPCFPQ CLDWIIENQR EDGSWGLNPT HPLLLKDSLS
121 STLACLLALT KWRVGDEQIK RGLGFIETQS WAIDNKDQIS
161 PLGFEIIFPS MIKSAEKLSL NLAINKRDST IKRALQNEFT
201 RNIEYMSEGV GELCDWKEII KLHQRQNGSL FDSPATTAAA
241 LIYHQHDKKC YEYLNSILQQ HKNWVPTMYP TKIHSLLCLV
281 DTLQNLGVHR HFKSEIKKAL DEIYRLWQQK NEEIFSNATH
321 CAMAFRLLRM SYYDVSSDEL AEFVDEEHFF ATSGKYTSHV
361 EILELHKASQ LAIDHEKDDI LDKINNWTRT FMEQKLLNNG
401 FIDRMSKKEV ELALRNFYII SDLAENRRYI KSYEENNFKI
441 LKAAYRSPNI NNKDLFIFSI RDFELCQAQH QEELQQLKRW
481 FEDCRLDQLG LSEQFISASY LCAIPIVPGP ELSDARLMYA
521 KYVILLTIVD DHFESFASTD ECLNIIELVE RWDDYASVGY
561 KSERVKVLFS MFYKSIEEIA TIAEIKQGRS VKNHLINLWL
601 KVMKLMLMER VEWCSGKTIP RIEEYLYVTS ITFGSRLIPL
641 TTQYFLGIKI SKDLLESDEI YGLCNCTGIV LRLLNDLQDS
681 KREQKEGSIN LVTLLMKSIS EEEAVMKMKE ILEMKRRELF
721 KMVLVQKKGS QLPQLCKEIF WRTCKWAHFT YSQTDRYRFP
761 EEMENHIDEV FYKPLNH
```

The *Solanum habrochaites* accession LA2106 zingiberene synthase enzyme with the foregoing amino acid sequence SEQ ID NO:16 is encoded by the following nucleotide sequence (SEQ ID NO:17).

```
  1 ATGATAGTTG GCTATAGAAG CACAATCATA ATCCTTTCTC
 41 ATCCTAAGCT AGGCAATGGG AAAACAATTT CATCCAATGC
 81 AATTTTCCAG AGATCATGTA GAGTAAGATG CAGCCACAGT
121 ACCACTTCAT CAATGAATGG TTTCGAAGAT GCAAGGGATA
161 GAATAAGGGA AAGTTTTGGG AAATTAGAGT TATCTCCTTC
201 TTCCTATGAC ACAGCATGGG TAGCTATGGT CCCTTCAAAA
241 CATTCACTAA ATGAGCCATG TTTTCCACAA TGTTTGGATT
281 GGATTATTGA AAATCAAAGA GAAGATGGAT CTTGGGGACT
321 AAACCCTACC CATCCATTGC TTCTCAAGGA CTCACTTTCT
361 TCCACTCTTG CATGTTTGCT TGCACTAACC AAATGGAGAG
401 TTGGGGATGA GCAAATCAAA AGAGGCCTTG GCTTTATTGA
441 AACCCAGAGT TGGGCAATTG ATAACAAGGA TCAAATTTCA
481 CCTCTAGGAT TTGAAATTAT ATTTCCCAGT ATGATCAAGT
521 CTGCAGAAAA ACTAAGCTTA AATCTAGCAA TTAACAAAAG
561 AGATTCAACA ATTAAAAGAG CATTACAGAA TGAATTCACG
601 AGGAATATTG AATATATGAG TGAAGGAGTT GGTGAATTAT
641 GTGATTGGAA GGAAATAATA AAGTTACATC AAAGGCAAAA
681 TGGTTCATTA TTTGATTCAC CAGCCACTAC TGCAGCTGCC
721 TTGATTTACC ATCAGCATGA TAAAAAATGC TATGAATATC
761 TTAATTCAAT CTTGCAACAA CACAAAAATT GGGTTCCCAC
801 TATGTATCCA ACAAAGATAC ATTCATTGCT TTGCTTGGTT
841 GATACACTTC AAAATCTTGG AGTACATCGG CATTTTAAAT
881 CAGAAATAAA GAAAGCCCTA GATGAAATAT ACAGGCTATG
921 GCAACAAAAG AATGAAGAAA TTTTCTCAAA TGCCACCCAT
```

```
 961 TGTGCTATGG CTTTTCGACT TCTAAGGATG AGCTACTATG
1001 ATGTCTCCTC GGATGAACTA GCAGAATTTG TGGATGAAGA
1041 ACATTTCTTT GCAACAAGTG GGAAATATAC AAGTCATGTT
1081 GAAATTCTTG AACTCCACAA AGCATCACAA TTGGCTATTG
1121 ATCATGAGAA AGATGACATT TTGGATAAGA TTAACAATTG
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACAA TTTTAAAATC
1321 TTAAAAGCAG CTTATAGGTC ACCTAACATT AACAATAAGG
1361 ACTTGTTTAT ATTTTCAATA CGCGACTTTG AATTATGCCA
1401 AGCTCAACAC CAAGAAGAAC TTCAACAACT CAAGAGGTGG
1441 TTTGAAGATT GTAGATTGGA CCAACTCGGA CTTTCGGAAC
1481 AATTTATATC TGCTAGTTAC TTATGTGCTA TTCCTATTGT
1521 CCCCGGGCCT GAATTATCCG ATGCTCGTCT CATGTACGCG
1561 AAATACGTCA TTCTCTTGAC TATTGTCGAT GATCATTTCG
1601 AGAGTTTTGC ATCTACAGAT GAATGTCTCA ACATCATTGA
1641 ATTAGTAGAA AGGTGGGATG ACTATGCAAG TGTAGGTTAT
1681 AAATCTGAGA GGGTTAAAGT TTTATTTTCA ATGTTTTACA
1721 AATCAATAGA GGAGATTGCA ACAATTGCTG AAATTAAACA
1761 AGGACGATCT GTCAAAAATC ACCTTATTAA TTTGTGGCTT
1801 AAAGTGATGA AGTTGATGTT GATGGAACGA GTAGAGTGGT
1841 GTTCTGGCAA GACAATACCA AGAATAGAAG AGTATTTGTA
1881 TGTTACTTCT ATAACATTTG GTTCAAGATT GATTCCTCTC
1921 ACAACACAAT ATTTTCTTGG AATAAAAATA TCCAAAGATC
1961 TTTTAGAAAG TGATGAAATT TATGGTTTAT GCAATTGTAC
2001 CGGTATAGTC TTGAGGCTCC TCAATGATTT ACAAGATTCC
2041 AAGAGAGAAC AAAAGGAGGG CTCAATAAAT TTAGTCACAT
2081 TACTAATGAA AAGTATCTCT GAGGAAGAAG CTGTAATGAA
2121 GATGAAGGAA ATCTTGGAAA TGAAAAGAAG AGAGTTATTT
2161 AAAATGGTTT TAGTTCAAAA AAAGGGAAGC CAATTGCCTC
2201 AATTATGCAA AGAAATATTT TGGAGGACAT GCAAATGGGC
2241 TCATTTCACT TATTCACAAA CTGATAGATA TAGATTTCCA
2281 GAGGAAATGG AGAATCACAT TGATGAAGTC TTTTACAAAC
2321 CACTCAATCA TTAA
```

The *Solanum habrochaites* accession LA1352 zingiberene synthase has the following amino acid sequence (SEQ ID NO:18).

```
  1 MIVGYRSTII ILSHPKLGNG KTISSNAIFQ RSCRVRCSHS
 41 TTSSMNGFED ARDRIRESFG KLELSPSSYD TAWVAMVPSK
 81 HSLNEPCFPQ CLDWIIENQR EDGSWGLNPT HPLLLKDSLS
121 STLACLLALT KWRVGDEQIK RGLGFIETQS WAIDNKDQIS
161 PLGFEIIFPS MIKSAEKLSL NLAINKRDST IKRALQNEFT
201 RNIEYMSEGV GELCDWKEII KLHQRQNGSL FDSPATTAAA
241 LIYHQHDKKC YEYLNSILQQ HKNWVPTMYP TKIHSLLCLV
281 DTLQNLGVHR HFKSEIKKAL DEIYRLWQQK NEEIFSNATH
321 CAMAFRLLRM SYYDVSSDEL AEFVDEEHFF ATSGKYTSHV
361 EILELHKASQ LAIDHEKDDI LDKINNWTRT FMEQKLLNNG
401 FIDRMSKKEV ELALRNFYII SDLAENRRYI KSYEENNFKI
441 LKAAYRSPNI NNKDLFIFSI RDFELCQAQH QEELQQLKRW
481 FEDCRLDQLG LSEQFISASY LCAIPIVPGP ELSDARLMYA
521 KYVILLTIVD DHFESFASTD ECLNIIELVE RWDDYASVGY
561 KSERVKVLFS MFYKSIEEIA TIAEIKQGRS VKNHLINLWL
601 KVMKLMLMER VEWCSGKTIP RIEEYLYVTS ITFGSRLIPL
641 TTQYFLGIKI SKDLLESDEI YGLCNCTGIV LRLLNDLQDS
681 KREQKEGSIN LVTLLMKSIS EEEAVMKMKE ILEMKRRELF
721 KMVLVQKKGS QLPQLCKEIF WRTCKWAHFT YSQTDRYRFP
761 EEMENHIDEV FYKPLNH
```

The *Solanum habrochaites* accession LA1352 zingiberene synthase enzyme with the foregoing amino acid sequence SEQ ID NO:18 is encoded by the following nucleotide sequence (SEQ ID NO:19).

```
  1 ATGATAGTTG GCTATAGAAG CACAATCATA ATCCTTTCTC
 41 ATCCTAAGCT AGGCAATGGG AAAACAATTT CATCCAATGC
 81 AATTTTCCAG AGATCATGTA GAGTAAGATG CAGCCACAGT
121 ACCACTTCAT CAATGAATGG TTTCGAAGAT GCAAGGGATA
161 GAATAAGGGA AAGTTTTGGG AAATTAGAGT TATCTCCTTC
201 TTCCTATGAC ACAGCATGGG TAGCTATGGT CCCTTCAAAA
241 CATTCACTAA ATGAGCCATG TTTTCCACAA TGTTTGGATT
281 GGATTATTGA AAATCAAAGA GAAGATGGAT CTTGGGGACT
321 AAACCCTACC CATCCATTGC TTCTCAAGGA CTCACTTTCT
361 TCCACTCTTG CATGTTTGCT TGCACTAACC AAATGGAGAG
401 TTGGGGATGA GCAAATCAAA AGAGGCCTTG GCTTTATTGA
441 AACCCAGAGT TGGGCAATTG ATAACAAGGA TCAAATTTCA
481 CCTCTAGGAT TTGAAATTAT ATTTCCCAGT ATGATCAAGT
521 CTGCAGAAAA ACTAAGCTTA AATCTAGCAA TTAACAAAAG
561 AGATTCAACA ATTAAAAGAG CATTACAGAA TGAATTCACG
601 AGGAATATTG AATATATGAG TGAAGGAGTT GGTGAATTAT
641 GTGATTGGAA GGAAATAATA AAGTTACATC AAAGGCAAAA
681 TGGTTCATTA TTTGATTCAC CAGCCACTAC TGCAGCTGCC
721 TTGATTTACC ATCAGCATGA CAAAAAATGC TATGAATATC
```

```
761  TTAATTCAAT CTTGCAACAA CACAAAAATT GGGTTCCCAC
801  TATGTATCCA ACAAAGATAC ATTCATTGCT TTGCTTGGTT
841  GATACACTTC AAAATCTTGG AGTACATCGG CATTTTAAAT
881  CAGAAATAAA GAAAGCCCTA GATGAAATAT ACAGGCTATG
921  GCAACAAAAG AATGAAGAAA TTTTCTCAAA TGCCACCCAT
961  TGTGCTATGG CTTTTCGACT TCTAAGGATG AGCTACTATG
1001 ATGTCTCCTC GGATGAACTA GCAGAATTTG TGGATGAAGA
1041 ACATTTCTTT GCAACAAGTG GGAAATATAC AAGTCATGTT
1081 GAAATTCTTG AACTCCACAA AGCATCACAA TTGGCTATTG
1121 ATCATGAGAA AGATGACATT TTGGATAAGA TTAACAATTG
1161 GACAAGAACA TTTATGGAGC AAAAACTCTT AAACAATGGC
1201 TTCATAGATA GGATGTCAAA AAAGGAGGTG GAACTTGCTT
1241 TGAGGAATTT TTATATCATA TCTGATCTAG CAGAAAATAG
1281 AAGATATATA AAGTCATACG AAGAGAACAA TTTTAAAATC
1321 TTAAAAGCAG CTTATAGGTC ACCTAACATT AACAATAAGG
1361 ACTTGTTTAT ATTTTCAATA CGCGACTTTG AATTATGCCA
1401 AGCTCAACAC CAAGAAGAAC TTCAACAACT CAAGAGGTGG
1441 TTTGAAGATT GTAGATTGGA CCAACTCGGA CTTTCGGAAC
1481 AATTTATATC TGCTAGTTAC TTATGTGCTA TTCCTATTGT
1521 CCCCGGGCCT GAATTATCCG ATGCTCGTCT CATGTACGCG
1561 AAATACGTCA TTCTCTTGAC TATTGTCGAT GATCATTTCG
1601 AGAGTTTTGC ATCTACAGAT GAATGTCTCA ACATCATTGA
1641 ATTAGTAGAA AGGTGGGATG ACTATGCAAG TGTAGGTTAT
1681 AAATCTGAGA GGGTTAAAGT TTTATTTTCA ATGTTTTACA
1721 AATCAATAGA GGAGATTGCA ACAATTGCTG AAATTAAACA
1761 AGGACGATCT GTCAAAAATC ACCTTATTAA TTTGTGGCTT
1801 AAAGTGATGA AGTTGATGTT GATGGAACGA GTAGAGTGGT
1841 GTTCTGGCAA GACAATACCA AGAATAGAAG AGTATTTGTA
1881 TGTTACTTCT ATAACATTTG GTTCAAGATT GATTCCTCTC
1921 ACAACACAAT ATTTTCTTGG AATAAAAATA TCCAAAGATC
1961 TTTTAGAAAG TGATGAAATT TATGGTTTAT GCAATTGTAC
2001 CGGTATAGTC TTGAGGCTCC TCAATGATTT ACAAGATTCC
2041 AAGAGAGAAC AAAAGGAGGG CTCAATAAAT TTAGTCACAT
2081 TACTAATGAA AAGTATCTCT GAGGAAGAAG CTGTAATGAA
2121 GATGAAGGAA ATCTTGGAAA TGAAAAGAAG AGAGTTATTT
2161 AAAATGGTTT TAGTTCAAAA AAAGGGAAGC CAATTGCCTC
2201 AATTATGCAA AGAAATATTT TGGAGGACAT GCAAATGGGC
2241 TCATTTCACT TATTCACAAA CTGATAGATA TAGATTTCCA
2281 GAGGAAATGG AGAATCACAT TGATGAAGTC TTTTACAAAC
2321 CACTCAATCA TTAA
```

The foregoing zingiberene synthase enzyme sequences exhibit significant sequence identity, as is illustrated by the following Table 2. Table 2 shows the number of amino acid differences between the indicated enzyme sequences above the diagonal and the percentage amino acid identity between the indicated sequences below the diagonal.

TABLE 2

Sequence Identities of Zingiberene Synthase Enzymes

|        | LA1352 | LA1731 | LA2106 | LA2167 | LA2196 |
|--------|--------|--------|--------|--------|--------|
| LA1352 |        | 16     | 0      | 15     | 7      |
| LA1731 | 97.9%  |        | 16     | 3      | 11     |
| LA2106 | 100.0% | 97.9%  |        | 15     | 7      |
| LA2167 | 98.0%  | 99.6%  | 98.0%  |        | 10     |
| LA2196 | 99.1%  | 98.6%  | 99.1%  | 98.7%  |        |

Thus, for example, the zingiberene synthase enzyme of *Solanum habrochaites* accession LA1352 has 100% sequence identity with the LA 2106 zingiberene synthase. But the zingiberene synthases from *Solanum habrochaites* accessions LA1731 and LA1352 have 16 amino acid differences and only 97.9% amino acid sequence identity.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative and exemplary and not intended as limitations on the scope of the invention. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. In this document, the term "or" is used to refer to a nonexclusive or, such that "A or B" includes "A but not B," "B but not A," and "A and B," unless otherwise indicated.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to summarize embodiments of the invention according to the foregoing description given in the specification. Because this application is a provisional application, these statements may become changed upon preparation and filing of a nonprovisional application. Such changes are not intended to affect the scope of equivalents according to the claims issuing from the nonprovisional application, if such changes occur. According to 35 U.S.C. §111(b), claims are not required for a provisional application. Consequently, the statements of the invention cannot be interpreted to be claims pursuant to 35 U.S.C. §112.

Statements Describing Embodiments of the Invention

1. An isolated nucleic acid encoding a zingiberene synthase wherein the nucleic acid encodes a zingiberene synthase with an amino acid sequence selected from the group consisting of SEQ ID NOs: 2, 4, 6, 8, 11, 12, 14, 16, 18, an amino acid sequence with at least 90% sequence identity to any of SEQ ID NOs: 2, 4, 6, 8, 11, 12, 14, 16, 18, and a combination thereof
2. The isolated nucleic acid of statement 1, wherein the nucleic acid selectively hybridizes to a DNA with any of SEQ ID NOs: 1, 3, 5, 7, 13, 15, 17, or 19, under stringent hybridization conditions.
3. The isolated nucleic acid of statement 2, wherein the stringent hybridization conditions comprise a wash in 0.1× SSC, 0.1% SDS at 65° C.
4. The isolated nucleic acid of any of statements 1-3, wherein the nucleic acid has about at least about 80% sequence identity with a nucleic acid having a nucleotide sequence selected from the group consisting of any of SEQ ID NO:1, 3, 5, 7, 13, 15, 17, 19, or a combination thereof.
5. The isolated nucleic acid of any of statements 1-4, wherein the nucleic acid encodes a zingiberene synthase.
6. The isolated nucleic acid of any of statements 1-5, wherein the nucleic acid encodes a zingiberene synthase that can catalyze the synthesis of zingiberene from 2Z,6Z-farnesyl diphosphate.
7. The isolated nucleic acid of statements 6, wherein the zingiberene synthase does not synthesize sesquiterpenes from neryl diphosphate (NPP).
8. The isolated nucleic acid of any of statements 1-7, wherein the nucleic acid encodes a zingiberene synthase that can catalyze the synthesis of zingiberene from 2Z,6Z-Farnesol diphosphate with at least about 50%, of the activity of a zingiberene synthase with any of amino acid sequences SEQ ID NO: 2, 4, 6, 8, 11, 12, 14, 16, or 18.
9. The isolated nucleic acid of any of statements 1-7, wherein the nucleic acid encodes a zingiberene synthase that can catalyze the synthesis of zingiberene from 2Z,6Z-Farnesol diphosphate with at least about 50%, of the activity of a zingiberene synthase with any of the SEQ ID NO:2 or 4.
10. An expression cassette comprising the nucleic acid of any of statements 1-9 operably linked to a promoter functional in a host cell.
11. The expression cassette of statement 10, which further comprises a selectable marker gene.
12. The expression cassette of statement 10 or 11, further comprising plasmid DNA.
13. The expression cassette of statement 10, 11 or 12, within an expression vector.
14. The expression cassette of statement 10, 11, 12 or 13, wherein the promoter is a promoter functional in a microorganism and/or during plant development or growth.
15. A transgenic plant cell comprising the isolated nucleic acid of any of statements 1-9 and/or the expression cassette of any of statements 10-14.
16. The plant cell of statement 15, wherein the plant cell is a monocot cell.
17. The plant cell of statement 15, wherein the plant cell is a dicot cell.
18. The plant cell of any of statements 15-17, wherein the plant cell is from a vegetable-producing plant, grain-producing plant, sugar-producing plant, nut-producing plant, fruit-producing plant, flowering plant, fuel-producing plant or wood-producing plant.
19. The plant cell of any of statements 15-18, wherein the plant cell is from an ornamental plant, a tomato, a broccoli, a green bean, a sweet pea, a squash, an eggplant, an asparagus, an artichoke, an avocado, a celery, a carrot, a radish, a cucumber, a potato, a lettuce, a spinach, a soybean, a grape, an orange, a lemon, a grapefruit, a corn, a tobacco, a cotton, a canola, an alfalfa, a rice, a wheat, an oat, a sorghum and/or a flax plant.
20. A microorganism comprising the isolated nucleic acid of any of statements 1-9 and/or the expression cassette of any of statements 10-14.
21. The microorganism of statement 20, wherein the microorganism is a bacterial or yeast cell.
22. A transgenic plant comprising the isolated nucleic acid of any of statements 1-9 and/or the expression cassette of any of statements 10-14 and/or the plant cell of any of statements 15-19.
23. The transgenic plant of statement 22, wherein the plant is a monocot.
24. The transgenic plant of statement 22, wherein the plant is a dicot.
25. The transgenic plant of any of statements 22-24, wherein the plant is a vegetable-producing plant, grain-producing plant, sugar-producing plant, nut-producing plant, fruit-producing plant, flowering plant, fuel-producing plant or wood-producing plant.
26. The transgenic plant of statements 22-25, wherein the plant is an ornamental plant, a tomato, a broccoli, a green bean, a sweet pea, a squash, an eggplant, an asparagus, an artichoke, an avocado, a celery, a carrot, a radish, a cucumber, a potato, a lettuce, a spinach, a soybean, a grape, an orange, a lemon, a grapefruit, a corn, a tobacco, a cotton, a canola, an alfalfa, a rice, a wheat, an oat, a sorghum and/or a flax plant.
27. The transgenic plant any of statements 22-26, wherein the plant is a vegetable-producing plant.
28. The transgenic plant of any of statements 22-27, wherein the plant is a tomato plant.

29. A method for generating a plant, comprising:
   a) stably transforming plant cells with the nucleic acid of any of statements 1-14 or the expression cassette of any of statements 15-19 to generate transformed plant cells;
   b) regenerating the transformed plant cells into at least one transgenic plant, wherein a zingiberene synthase is expressed in the at least one transgenic plant in an amount sufficient to synthesize zingiberene by the transgenic plant.
30. The method of statement 29, wherein the transgenic plant is fertile.
31. The method of statement 29 or 30, further comprising recovering transgenic seeds from the transgenic plant, wherein the transgenic seeds comprise the nucleic acid encoding a zingiberene synthase.
32. The method of any of statements 29-31, wherein the plant is a monocot.
33. The method of any of statements 29-31, wherein the plant is a dicot.
34. The method of any of statement 29-33, wherein the plant is a vegetable-producing plant, grain-producing plant, sugar-producing plant, nut-producing plant, fruit-producing plant, flowering plant, fuel-producing plant or wood-producing plant.
35. The method of any of statement 29-33, wherein the plant is an ornamental plant, a tomato, a broccoli, a green bean, a sweet pea, a squash, an eggplant, an asparagus, an artichoke, an avocado, a celery, a carrot, a radish, a cucumber, a potato, a lettuce, a spinach, a soybean, a grape, an orange, a lemon, a grapefruit, a corn, a tobacco, a cotton, a canola, an alfalfa, a rice, a wheat, an oat, a sorghum and/or a flax plant.
36. The method of any of statements 29-33, wherein the plant is a vegetable-producing plant.
37. The method of any of statements 29-33, 35 or 36, wherein the plant is a tomato plant.
38. The method of any of statements 29-37, wherein the terpenes synthesized by the plant comprises at least 1% zingiberene.
39. The method of any of statements 29-38, wherein the terpenes synthesized by the plant comprises at least 5% zingiberene.
40. The method of any of statements 29-39, wherein the terpenes synthesized by the plant comprises at least 10% zingiberene.
41. The method of any of statements 29-40, wherein the terpenes synthesized by the plant comprises at least 20% zingiberene.
42. The method of any of statements 29-41, further comprising breeding a fertile transgenic plant to yield a progeny plant that has an increase in the percentage of zingiberene synthesized by the progeny plant relative to the corresponding untransformed plant.
43. The method of any of statements 29-42, further comprising breeding the fertile transgenic plant to yield a progeny plant that has an increase in the percentage of zingiberene synthesized by the progeny plant as a dominant trait while still maintaining functional agronomic characteristics relative to the corresponding untransformed plant.
44. The method of any of statements 29-43, wherein the transformed plant cell is transformed by a method selected from the group consisting of electroporation, microinjection, microprojectile bombardment, and liposomal encapsulation.
45. The method of any of statements 29-44, further comprising stably transforming the plant cell with at least one selectable marker gene.
46. The method of any of statements 29-45, further comprising collecting the transgenic seeds.
47. A fertile transgenic plant capable of synthesizing an increased percent zingiberene, wherein the genome of which is stably transformed by the nucleic acid of any of statements 1-9 or the expression cassette of any of statements 10-14, wherein the terpene synthase nucleic acid is transmitted through a complete normal sexual cycle of the transgenic plant to the next generation.
48. The plant of statement 47, wherein the plant is a monocot.
49. The plant of statement 47, wherein the plant is a dicot.
50. The plant of any of statements 47-49, wherein the plant is a vegetable-producing plant, grain-producing plant, sugar-producing plant, nut-producing plant, fruit-producing plant, flowering plant, fuel-producing plant, ornamental plant or wood-producing plant.
51. The plant of any of statements 47-50, wherein the plant is a tomato, a broccoli, a green bean, a sweet pea, a squash, an eggplant, an asparagus, an artichoke, an avocado, a celery, a carrot, a radish, a cucumber, a potato, a lettuce, a spinach, a soybean, a grape, an orange, a lemon, a grapefruit, a corn, a tobacco, a cotton, a canola, an alfalfa, a rice, a wheat, an oat, a sorghum and/or a flax plant.
52. The plant of any of statements 47-51, wherein the plant is a vegetable-producing plant.
53. The plant of any of statements 47, 49, 50, 51 or 52, wherein the plant is a tomato or potato plant.
54. The plant of any of statements 47-53, wherein the percent zingiberene synthesized by the plant is increased relative to the corresponding untransformed plant.
55. The plant of any of statements 47-54, wherein the percent zingiberene synthesized by the plant is increased by at least 1% relative to the corresponding untransformed plant.
56. The plant of any of statements 47-55, wherein the percent zingiberene synthesized by the plant is increased by at least 2-5% relative to the corresponding untransformed plant.
57. The plant of any of statements 47-56, wherein the percent zingiberene synthesized by the plant comprises at least 1% of the plant terpenes.
58. The plant of any of statements 47-57, wherein the percent zingiberene synthesized by the plant comprises at least 5% of the plant terpenes.
59. The plant of any of statements 47-58, wherein the percent zingiberene synthesized by the plant comprises at least 10% of the plant terpenes.
60. The plant of any of statements 47-59, wherein the percent zingiberene synthesized by the plant comprises at least 20% of the plant terpenes.
61. The plant of any of statements 47-60, wherein the percent zingiberene synthesized by the plant comprises at least 25% of the plant terpenes.
62. The plant of any of statements 47-61, wherein the percent zingiberene synthesized by the plant comprises about 1-30% of the plant terpenes.
63. A method of making zingiberene comprising:
   a) culturing the microorganism of statement 20 or 21 under conditions sufficient for expression of the zingiberene synthase; and
   b) providing the microorganism with a substrate for the zingiberene synthase to thereby make the zingiberene.
64. The method of statement 63, wherein the substrate is 2Z,6Z-farnesyl diphosphate.
65. The method of any of statements 63 or 64, wherein the microorganism is a bacterial or yeast cell.
66. The method of any of statements 63-65, wherein the microorganism is *E. coli*.

67. An isolated zingiberene synthase comprising an amino acid sequence selected from the group consisting of SEQ ID NOs: 2, 4, 6, 8, 11, 12, 14, 16, 18, an amino acid sequence with at least 90% sequence identity to any of SEQ ID NOs: 2, 4, 6, 8, 11, 12, 14, 16, 18, and a combination thereof
68. A method of manufacturing zingiberene comprising: contacting the isolated zingiberene synthase of statement 67 with 2Z,6Z-farnesyl diphosphate to thereby manufacture a terpene.
69. A method for controlling insect destruction of a plant comprising applying a composition comprising an effective amount of zingiberene one or more times to the plants.
70. The method of statement 69, wherein the insect destruction of the plant is caused by whiteflies and/or thrips.
71. The isolated nucleic acid of statement 1, wherein the nucleic acid has selected from the group consisting of SEQ ID NOs: 2, 4, 6, 8, 11, 12, 14, 16, 18, an amino acid sequence with at least 96% sequence identity to any of SEQ ID NOs: 2, 4, 6, 8, 11, 12, 14, 16, 18, and a combination thereof.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are described within the following claims.

What is claimed:

1. An isolated nucleic acid comprising a cDNA encoding a zingiberene synthase with at least 97% sequence identity to any of amino acid sequences SEQ ID NO: 2, 4, 6, 8, 11, 12, 14, 16, or 18.

2. The isolated nucleic acid of claim 1, wherein the cDNA encoding the zingiberene synthase comprises a sequence with at least 97% sequence identity to any of nucleotide sequences SEQ ID NO: 1, 3, 5, 7, 13, 15, 17, or 19.

3. An expression cassette comprising a cDNA encoding a zingiberene synthase with at least 97% sequence identity to any of amino acid sequences SEQ ID NO: 2, 4, 6, 8, 11, 12, 14, 16, or 18 wherein the cDNA encoding the zingiberene synthase is operably linked to a heterologous promoter functional in a host cell.

4. A host cell comprising the expression cassette of claim 3.

5. The host cell of claim 4, wherein the host cell is a plant cell.

6. The host cell of claim 4, wherein the host cell is a microorganism.

7. A plant tissue comprising the nucleic acid of claim 1.

8. A plant tissue comprising the host cell of claim 5.

9. A plant comprising the nucleic acid of claim 1.

10. A plant comprising the plant tissue of claim 8.

* * * * *

```
                              SEQUENCE LISTING

<160> NUMBER OF SEQ ID NOS: 22

<210> SEQ ID NO 1
<211> LENGTH: 2334
<212> TYPE: DNA
<213> ORGANISM: Solanum habrochaites

<400> SEQUENCE: 1
atgatagttg gctatagaag cacaatcata acccttctc atcctaagct aggcaatggg      60
aaaacaattt catccaatgc aattttccgg agatcatgta gagtaagatg cagccacagt     120
accccttcat caatgaatgg tttcgaagat gcaagggata gaataaggga aagttttggg     180
aaagtagagt tatctccttc ttcctatgac acagcatggg tagctatggt cccttcaaaa     240
cattcactaa atgagccatg ttttccacaa tgtttggatt ggattattga aaatcaaga      300 gaagatggat cttggggact aaaccctagc catccattgc ttcttaagga ctcactttct     360
tccactcttg catgtttgct tgcactaacc aaatggagag ttggagatga gcaaatcaaa     420
agaggccttg gctttattga aacccagagt tgggcaattg ataacaagga tcaaatttca     480
cctctaggat ttgaaattat atttcccagt atgatcaagt ctgcagaaaa actaaactta     540
aatctagcaa ttaacaaaag agattcaaca attaaaagag cattacagaa tgagttcacg     600
aggaatattg aatatatgag tgaaggattt ggtgaattat gtgattggaa ggaaataata     660
aagttacatc aaaggcaaaa tggttcatta tttgattcac cagccactac tgcagctgcc     720
ttgatttacc atcagcatga taaaaaatgc tatgaatatc ttaattcaat cttgcaacaa     780
cacaaaaatt gggttcccac tatgtatcca acaaagatac attcattgct ttgcttggtt     840
gatacacttc aaaatcttgg agtacatcgg cattttaaat cagaaataaa gaaagcccta     900
gatgaaatat acaggctatg gcaacaaaag aatgaagaaa ttttctcaaa tgtcacccat     960
tgtgctatgg cttttcgact tctaaggata agctactatg atgtctcctc agatgaacta    1020
gcagaatttg tggatgaaga acatttcttt gcaacaagtg ggaaatatac aagtcatgtt    1080
gaaattcttg aactccacaa agcatcacaa ttggctattg atcatgagaa agatgacatt    1140
ttggataaga ttaacaattg gacaagaaca tttatggagc aaaaactctt aaacaatggc    1200
ttcatagata ggatgtcaaa aaaggaggtg gaacttgctt tgaggaattt ttatatcata    1260
tctgatctag cagaaaatag aagatatata aagtcatacg aagagaacaa ttttaaaatc    1320
ttaaaagcag cttataggtc acctaacatt aacaataagg acttgtttat attttcaata    1380
```

```
cgcgactttg aattatgcca agctcaacac caagaagaac ttcaacaact caagaggtgg    1440
tttgaagatt gtagattgga ccaactcgga ctttcggaac aatttatatc tgctagttac    1500
ttatgtgcta ttcctattgt ccccgggcct gaattatccg atgctcgtct cgtgtacgcg    1560
aaatacgtca tgctcttgac tattgtcgat gatcatttcg agagttttgc atctacagat    1620
gaatgtctca acatcattga attagtagaa aggtgggatg actatgcaag tgtaggttat    1680
aaatctgaga gggttaaagt tttatttttca atgttttaca aatcaataga ggagattgca    1740
acaattgctg aaattaaaca aggacgatct gtcaaaaatc accttattaa tttgtggctt    1800
aaagtgatga agttgatgtt gatggaacga gtagagtggt gttctggcaa gacaatacca    1860
agaatagaag agtatttgta tgttagttct ataacatttg gttcaagatt gattcctctc    1920
acaacacaat attttattgg aataaaaata tccaaagatc ttttagaaag tgatgaaatt    1980
tatggtttat gcaattttac cggtatagtc ttgaggctcc tcaatgattt acaagattcc    2040
aagagagaac aaaaggaggg ctcaataaat ttagtcacat tactaatgaa aagtatctct    2100
gaggaagaag ctataatgaa gatgaaggaa atccttggaaa tgaaaagaag agagttattt    2160
aaaatggttt tagttcaaaa aaagggaagc caattgcctc aattatgcaa agaaatattt    2220
tggaggacat gcaaatgggc tcatttcact tattcacaaa ctgatagata tagatttcca    2280
gaggaaatgg agaatcacat tgatgaagtc ttttacaaac cactcaatca ttaa          2334
```

<210> SEQ ID NO 2
<211> LENGTH: 777
<212> TYPE: PRT
<213> ORGANISM: Solanum habrochaites

<400> SEQUENCE: 2

```
Met Ile Val Gly Tyr Arg Ser Thr Ile Ile Thr Leu Ser His Pro Lys
  1               5                  10                  15

Leu Gly Asn Gly Lys Thr Ile Ser Ser Asn Ala Ile Phe Arg Arg Ser
             20                  25                  30

Cys Arg Val Arg Cys Ser His Ser Thr Pro Ser Ser Met Asn Gly Phe
         35                  40                  45

Glu Asp Ala Arg Asp Arg Ile Arg Glu Ser Phe Gly Lys Val Glu Leu
     50                  55                  60

Ser Pro Ser Ser Tyr Asp Thr Ala Trp Val Ala Met Val Pro Ser Lys
 65                  70                  75                  80

His Ser Leu Asn Glu Pro Cys Phe Pro Gln Cys Leu Asp Trp Ile Ile
                 85                  90                  95

Glu Asn Gln Arg Glu Asp Gly Ser Trp Gly Leu Asn Pro His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
                165                 170                 175

Lys Leu Asn Leu Asn Leu Ala Ile Asn Lys Arg Asp Ser Thr Ile Lys
            180                 185                 190

Arg Ala Leu Gln Asn Glu Phe Thr Arg Asn Ile Glu Tyr Met Ser Glu
        195                 200                 205
```

```
Gly Phe Gly Glu Leu Cys Asp Trp Lys Glu Ile Ile Lys Leu His Gln
    210                 215                 220

Arg Gln Asn Gly Ser Leu Phe Asp Ser Pro Ala Thr Thr Ala Ala Ala
225                 230                 235                 240

Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
    290                 295                 300

Arg Leu Trp Gln Gln Lys Asn Glu Glu Ile Phe Ser Asn Val Thr His
305                 310                 315                 320

Cys Ala Met Ala Phe Arg Leu Leu Arg Ile Ser Tyr Tyr Asp Val Ser
                325                 330                 335

Ser Asp Glu Leu Ala Glu Phe Val Asp Glu Glu His Phe Phe Ala Thr
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
    370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Asn
                405                 410                 415

Phe Tyr Ile Ile Ser Asp Leu Ala Glu Asn Arg Arg Tyr Ile Lys Ser
            420                 425                 430

Tyr Glu Glu Asn Asn Phe Lys Ile Leu Lys Ala Ala Tyr Arg Ser Pro
        435                 440                 445

Asn Ile Asn Asn Lys Asp Leu Phe Ile Phe Ser Ile Arg Asp Phe Glu
    450                 455                 460

Leu Cys Gln Ala Gln His Gln Glu Glu Leu Gln Gln Leu Lys Arg Trp
465                 470                 475                 480

Phe Glu Asp Cys Arg Leu Asp Gln Leu Gly Leu Ser Glu Gln Phe Ile
                485                 490                 495

Ser Ala Ser Tyr Leu Cys Ala Ile Pro Ile Val Pro Gly Pro Glu Leu
            500                 505                 510

Ser Asp Ala Arg Leu Val Tyr Ala Lys Tyr Val Met Leu Leu Thr Ile
        515                 520                 525

Val Asp Asp His Phe Glu Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560

Lys Ser Glu Arg Val Lys Val Leu Phe Ser Met Phe Tyr Lys Ser Ile
                565                 570                 575

Glu Glu Ile Ala Thr Ile Ala Glu Ile Lys Gln Gly Arg Ser Val Lys
            580                 585                 590

Asn His Leu Ile Asn Leu Trp Leu Lys Val Met Lys Leu Met Leu Met
        595                 600                 605

Glu Arg Val Glu Trp Cys Ser Gly Lys Thr Ile Pro Arg Ile Glu Glu
    610                 615                 620

Tyr Leu Tyr Val Ser Ser Ile Thr Phe Gly Ser Arg Leu Ile Pro Leu
```

```
                625               630               635               640
            Thr Thr Gln Tyr Phe Ile Gly Ile Lys Ile Ser Lys Asp Leu Leu Glu
                          645               650               655
            Ser Asp Glu Ile Tyr Gly Leu Cys Asn Phe Thr Gly Ile Val Leu Arg
                          660               665               670
            Leu Leu Asn Asp Leu Gln Asp Ser Lys Arg Glu Gln Lys Glu Gly Ser
                          675               680               685
            Ile Asn Leu Val Thr Leu Leu Met Lys Ser Ile Ser Glu Glu Ala
                690               695               700
            Ile Met Lys Met Lys Glu Ile Leu Glu Met Lys Arg Arg Glu Leu Phe
            705               710               715               720
            Lys Met Val Leu Val Gln Lys Lys Gly Ser Gln Leu Pro Gln Leu Cys
                          725               730               735
            Lys Glu Ile Phe Trp Arg Thr Cys Lys Trp Ala His Phe Thr Tyr Ser
                          740               745               750
            Gln Thr Asp Arg Tyr Arg Phe Pro Glu Glu Met Glu Asn His Ile Asp
                          755               760               765
            Glu Val Phe Tyr Lys Pro Leu Asn His
                770               775

<210> SEQ ID NO 3
<211> LENGTH: 2214
<212> TYPE: DNA
<213> ORGANISM: Solanum habrochaites

<400> SEQUENCE: 3
ggatccatga atggttttga agatgcccgt gaccgtatcc gtgaatcgtt tggtaaagtg      60
gaactgagcc cgtcctcgta tgacaccgcc tgggttgcaa tggtcccgtc aaaacattcg     120
ctgaacgaac cgtgctttcc gcaatgtctg gattggatta tcgaaaacca gcgtgaagac     180
ggcagctggg gtctgaatcc gtctcacccg ctgctgctga agatagcct gagctctacc      240 ctggcctgtc tgctggcact gacgaaatgg cgtgtgggcg acgaacagat taaacgcggc     300
ctgggtttta tcgaaaccca aagctgggcg atcgataaca aagaccagat ttctccgctg     360
ggttttgaaa ttatcttccc gagtatgatc aaatccgccg aaaaactgaa cctgaatctg     420
gcaattaata acgtgatag taccatcaaa cgcgccctgc agaacgaatt cacgcgtaac     480
atcgaataca tgtccgaagg cttcggtgaa ctgtgcgatt ggaagaaat tatcaaactg     540 caccagcgcc aaaacggctc actgtttgat tcgccggcaa ccacggcagc agcactgatc     600
tatcatcagc acgacaaaaa atgttacgaa tacctgaact caatcctgca gcaacataaa     660
aattgggttc cgaccatgta cccgacgaaa attcactcgc tgctgtgcct ggtcgatacc     720
ctgcagaatc tgggtgtgca tcgtcacttt aaaagcgaaa tcaaaaaagc cctggatgaa     780
atctatcgcc tgtggcagca gaaaaacgaa gaaatcttta gcaatgtgac ccattgtgcc     840
atggcattcc gtctgctgcg catttcttat tacgatgtta gttccgacga actggctgaa     900
ttcgtcgatg aagaacattt ctttgcgacc agcggcaaat acacgtctca tgttgaaatc     960
ctggaactgc acaaagctag ccaactggcg attgatcacg aaaagatga catcctggac    1020 aaaattaaca attggacccg tacgtttatg aacagaaac tgctgaacaa cggtttcatc    1080
gatcgtatga gtaaaaaaga gtggaactg ccctgcgca actttatat atcagtgac       1140 ctggcagaaa atcgtcgcta catcaaatcc tacgaagaaa acaacttcaa atcctgaaa    1200 gctgcgtacc gttcaccgaa catcaacaac aaagacctgt tatcttctc gattcgcgac    1260
```

-continued

```
tttgaactgt gccaggcgca acatcaggaa gaactgcagc aactgaaacg ttggtttgaa    1320
gattgtcgcc tggaccaact gggcctgtcc gaacagttca tcagcgcctc ttatctgtgc    1380
gcaattccga tcgttccggg tccggaactg tctgatgctc gcctggtgta tgcgaaatac    1440
gttatgctgc tgaccattgt cgatgaccac tttgaaagct cgcttctac ggatgaatgc     1500 ctgaatatta tcgaactggt ggaacgttgg gatgactatg cgagtgttgg ctacaaatcc    1560
gaacgcgtga agttctgtt ttcaatgttc tacaaatcga tcgaagaaat tgctaccatc     1620
gcggaaatta acagggccg tagcgtcaaa aaccatctga ttaatctgtg ctgaaagtc      1680 atgaaactga tgctgatgga acgtgtggaa tggtgttctg gtaaaaccat cccgcgcatt   1740
gaagaatatc tgtacgtttc atcgattacg tttggcagtc gcctgatccc gctgaccacg   1800
cagtacttca tcggtatcaa aatcagtaaa gatctgctgg aatccgacga aatttacggc   1860
ctgtgcaact ttaccggtat cgtgctgcgt ctgctgaatg atctgcaaga ctcaaaacgc   1920
gaacagaaag aaggctcgat taatctggtt acgctgctga tgaaaagtat ctccgaagaa   1980
gaagcgatca tgaaaatgaa agaaatcctg gaaatgaaac gtcgcgaact gttcaaaatg   2040
gtcctggtgc agaaaaaagg tagccaactg ccgcagctgt gcaaagaaat cttttggcgc   2100
acctgtaaat gggcccattt cacctatagc cagacggatc gttaccgctt cccggaagaa   2160
atggaaaatc acattgacga agtgttctac aaaccgctga atcattgagt cgac          2214
```

<210> SEQ ID NO 4
<211> LENGTH: 733
<212> TYPE: PRT
<213> ORGANISM: Solanum habrochaites

<400> SEQUENCE: 4

```
Met Asn Gly Phe Glu Asp Ala Arg Asp Arg Ile Arg Glu Ser Phe Gly
 1               5                  10                  15

Lys Val Glu Leu Ser Pro Ser Ser Tyr Asp Thr Ala Trp Val Ala Met
                20                  25                  30

Val Pro Ser Lys His Ser Leu Asn Glu Pro Cys Phe Pro Gln Cys Leu
            35                  40                  45

Asp Trp Ile Ile Glu Asn Gln Arg Glu Asp Gly Ser Trp Gly Leu Asn
        50                  55                  60

Pro Ser His Pro Leu Leu Leu Lys Asp Ser Leu Ser Ser Thr Leu Ala
 65                  70                  75                  80

Cys Leu Leu Ala Leu Thr Lys Trp Arg Val Gly Asp Glu Gln Ile Lys
                 85                  90                  95

Arg Gly Leu Gly Phe Ile Glu Thr Gln Ser Trp Ala Ile Asp Asn Lys
            100                 105                 110

Asp Gln Ile Ser Pro Leu Gly Phe Glu Ile Ile Phe Pro Ser Met Ile
        115                 120                 125

Lys Ser Ala Glu Lys Leu Asn Leu Asn Leu Ala Ile Asn Lys Arg Asp
    130                 135                 140

Ser Thr Ile Lys Arg Ala Leu Gln Asn Glu Phe Thr Arg Asn Ile Glu
145                 150                 155                 160

Tyr Met Ser Glu Gly Phe Gly Glu Leu Cys Asp Trp Lys Glu Ile Ile
                165                 170                 175

Lys Leu His Gln Arg Gln Asn Gly Ser Leu Phe Asp Ser Pro Ala Thr
            180                 185                 190

Thr Ala Ala Ala Leu Ile Tyr His Gln His Asp Lys Lys Cys Tyr Glu
        195                 200                 205
```

```
Tyr Leu Asn Ser Ile Leu Gln Gln His Lys Asn Trp Val Pro Thr Met
    210                 215                 220
Tyr Pro Thr Lys Ile His Ser Leu Leu Cys Leu Val Asp Thr Leu Gln
225                 230                 235                 240
Asn Leu Gly Val His Arg His Phe Lys Ser Glu Ile Lys Lys Ala Leu
                245                 250                 255
Asp Glu Ile Tyr Arg Leu Trp Gln Gln Lys Asn Glu Glu Ile Phe Ser
            260                 265                 270
Asn Val Thr His Cys Ala Met Ala Phe Arg Leu Leu Arg Ile Ser Tyr
        275                 280                 285
Tyr Asp Val Ser Ser Asp Glu Leu Ala Glu Phe Val Asp Glu Glu His
    290                 295                 300
Phe Phe Ala Thr Ser Gly Lys Tyr Thr Ser His Val Glu Ile Leu Glu
305                 310                 315                 320
Leu His Lys Ala Ser Gln Leu Ala Ile Asp His Glu Lys Asp Asp Ile
                325                 330                 335
Leu Asp Lys Ile Asn Asn Trp Thr Arg Thr Phe Met Glu Gln Lys Leu
            340                 345                 350
Leu Asn Asn Gly Phe Ile Asp Arg Met Ser Lys Lys Glu Val Glu Leu
        355                 360                 365
Ala Leu Arg Asn Phe Tyr Ile Ile Ser Asp Leu Ala Glu Asn Arg Arg
    370                 375                 380
Tyr Ile Lys Ser Tyr Glu Glu Asn Asn Phe Lys Ile Leu Lys Ala Ala
385                 390                 395                 400
Tyr Arg Ser Pro Asn Ile Asn Asn Lys Asp Leu Phe Ile Phe Ser Ile
                405                 410                 415
Arg Asp Phe Glu Leu Cys Gln Ala Gln His Gln Glu Glu Leu Gln Gln
            420                 425                 430
Leu Lys Arg Trp Phe Glu Asp Cys Arg Leu Asp Gln Leu Gly Leu Ser
        435                 440                 445
Glu Gln Phe Ile Ser Ala Ser Tyr Leu Cys Ala Ile Pro Ile Val Pro
    450                 455                 460
Gly Pro Glu Leu Ser Asp Ala Arg Leu Val Tyr Ala Lys Tyr Val Met
465                 470                 475                 480
Leu Leu Thr Ile Val Asp Asp His Phe Glu Ser Phe Ala Ser Thr Asp
                485                 490                 495
Glu Cys Leu Asn Ile Ile Glu Leu Val Glu Arg Trp Asp Asp Tyr Ala
            500                 505                 510
Ser Val Gly Tyr Lys Ser Glu Arg Val Lys Val Leu Phe Ser Met Phe
        515                 520                 525
Tyr Lys Ser Ile Glu Glu Ile Ala Thr Ile Ala Glu Ile Lys Gln Gly
    530                 535                 540
Arg Ser Val Lys Asn His Leu Ile Asn Leu Trp Leu Lys Val Met Lys
545                 550                 555                 560
Leu Met Leu Met Glu Arg Val Glu Trp Cys Ser Gly Lys Thr Ile Pro
                565                 570                 575
Arg Ile Glu Glu Tyr Leu Tyr Val Ser Ser Ile Thr Phe Gly Ser Arg
            580                 585                 590
Leu Ile Pro Leu Thr Thr Gln Tyr Phe Ile Gly Ile Lys Ile Ser Lys
        595                 600                 605
Asp Leu Leu Glu Ser Asp Glu Ile Tyr Gly Leu Cys Asn Phe Thr Gly
    610                 615                 620
Ile Val Leu Arg Leu Leu Asn Asp Leu Gln Asp Ser Lys Arg Glu Gln
```

```
Lys Glu Gly Ser Ile Asn Leu Val Thr Leu Leu Met Lys Ser Ile Ser
625                 630                 635                 640

Glu Glu Glu Ala Ile Met Lys Met Lys Glu Ile Leu Glu Met Lys Arg
            645                 650                 655

Arg Glu Leu Phe Lys Met Val Leu Val Gln Lys Lys Gly Ser Gln Leu
        660                 665                 670

Pro Gln Leu Cys Lys Glu Ile Phe Trp Arg Thr Cys Lys Trp Ala His
    675                 680                 685

Phe Thr Tyr Ser Gln Thr Asp Arg Tyr Arg Phe Pro Glu Glu Met Glu
690                 695                 700

Asn His Ile Asp Glu Val Phe Tyr Lys Pro Leu Asn His
705                 710                 715                 720

725                 730
```

<210> SEQ ID NO 5
<211> LENGTH: 2334
<212> TYPE: DNA
<213> ORGANISM: Solanum habrochaites

<400> SEQUENCE: 5

| | | | | |
|---|---|---|---|---|
| atgatagttg | gctatagaag | cacaatcata | acccttctc | atcctaagct | aggcaatggg | 60 |
| aaaacaattt | catccaatgc | aattttccgg | agatcatgta | gagtaagatg | cagccacagt | 120 |
| accccttcat | caatgaatgg | tttcgaagat | gcaaggcata | gaataaggga | aagttttggg | 180 |
| aaagtagagt | tatctccttc | ttcctatgac | acagcatggg | tagctatggt | cccttcaaaa | 240 |
| cattcactaa | atgagccatg | ttttccacaa | tgtttggatt | ggattattga | aaatcaaaga | 300 |
| gaagatggat | cttggggact | aaaccctagc | catccattgc | ttcttaagga | ctcactttct | 360 |
| tccactcttg | catgtttgct | tgcactaacc | aaatggagag | ttggagatga | gcaaatcaaa | 420 |
| agaggcettg | gctttattga | aacccagagt | tgggcaattg | ataacaagga | tcaaatttca | 480 |
| cctctaggat | ttgaaattat | atttcccagt | atgatcaagt | ctgcagaaaa | actaaactta | 540 |
| aatctagcaa | ttaacaaaag | agattcaaca | attaaagag | cattacagaa | tgagttcacg | 600 |
| aggaatattg | aatatatgag | tgaaggattt | ggtgaattat | gtgattggaa | ggaaataata | 660 |
| aagttacatc | aaaggcaaaa | tggttcatta | tttgattcac | cagccactac | tgcagctgcc | 720 |
| ttgatttacc | atcagcatga | taaaaaatgc | tatgaatatc | ttaattcaat | cttgcaacaa | 780 |
| cacaaaaatt | gggttcccac | tatgtatcca | acaaagatac | attcattgct | ttgcttggtt | 840 |
| gatacacttc | aaaatcttgg | agtacatcgg | catttaaaat | cagaaataaa | gaaagcccta | 900 |
| gatgaaatat | acaggctatg | caacaaaag | aatgaagaaa | ttttctcaaa | tgtcacccat | 960 |
| tgtgctatgg | cttttcgact | tctaaggata | agctactatg | atgtctcctc | agatgaacta | 1020 |
| gcagaatttg | tggatgaaga | acatttctt | gcaacaagtg | ggaaatatac | aagtcatgtt | 1080 |
| gaaattcttg | aactccacaa | agcatcacaa | ttggctattg | atcatgagaa | agatgacatt | 1140 |
| ttggataaga | ttaacaattg | gacaagaaca | tttatggagc | aaaaactctt | aaacaatggc | 1200 |
| ttcatagata | ggatgtcaaa | aaaggaggtg | gaacttgctt | tgaggaattt | ttatatcata | 1260 |
| tctgatctag | cagaaaatag | aagatatata | aagtcatacg | aagagaacaa | ttttaaaatc | 1320 |
| ttaaaagcag | cttataggtc | acctaacatt | aacaataagg | acttgtttat | atttcaata | 1380 |
| cgcgactttg | aattatgcca | agctcaacac | aagaagaac | ttcaacaact | caagaggtgg | 1440 |
| tttgaagatt | gtagattgga | ccaactcgga | ctttcggaac | aatttatatc | tgctagttac | 1500 |
| ttatgtgcta | ttcctattgt | ccccgggcct | gaattatccg | atgctcgtct | cgtgtacgcg | 1560 |

```
aaatacgtca tgctcttgac tattgtcgat gatcatttcg agagttttgc atctacagat   1620
gaatgtctca acatcattga attagtagaa aggtgggatg actatgcaag tgtaggttat   1680
aaatctgaga gggttaaagt tttatttca atgttttaca aatcaataga ggagattgca    1740
acaattgctg aaattaaaca aggacgatct gtcaaaaatc accttattaa tttgtggctt   1800
aaagtgatga agttgatgtt gatggaacga gtagagtggt gttctggcaa gacaatacca   1860
agaatagaag agtatttgta tgttagttct ataacatttg gttcaagatt gattcctctc   1920
acaacacaat attttattgg aataaaaata tccaagatc ttttagaaag tgatgaaatt    1980
tatggtttat gcaattttac cggtatagtc ttgaggctcc tcaatgattt acaagattcc   2040
aagagagaac aaaaggaggg ctcaataaat ttagtcacat tactaatgaa aagtatctct   2100
gaggaagaag ctataatgaa gatgaaggaa atccttggaaa tgaaaagaag agagttattt  2160
aaaatggttt tagttcaaaa aaagggaagc caattgcctc aattatgcaa agaaatattt   2220
tggaggacat gcaaatgggc tcatttcact tattcacaaa ctgatagata tagatttcca   2280
gaggaaatgg agaatcacat tgatgaagtc ttttacaaac cactcaatca ttaa          2334
```

```
<210> SEQ ID NO 6
<211> LENGTH: 777
<212> TYPE: PRT
<213> ORGANISM: Solanum habrochaites

<400> SEQUENCE: 6

Met Ile Val Gly Tyr Arg Ser Thr Ile Ile Thr Leu Ser His Pro Lys
  1               5                  10                  15

Leu Gly Asn Gly Lys Thr Ile Ser Ser Asn Ala Ile Phe Arg Arg Ser
             20                  25                  30

Cys Arg Val Arg Cys Ser His Ser Thr Pro Ser Ser Met Asn Gly Phe
         35                  40                  45

Glu Asp Ala Arg Asp Arg Ile Arg Glu Ser Phe Gly Lys Val Glu Leu
     50                  55                  60

Ser Pro Ser Ser Tyr Asp Thr Ala Trp Val Ala Met Val Pro Ser Lys
 65                  70                  75                  80

His Ser Leu Asn Glu Pro Cys Phe Pro Gln Cys Leu Asp Trp Ile Ile
                 85                  90                  95

Glu Asn Gln Arg Glu Asp Gly Ser Trp Gly Leu Asn Pro Ser His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
                165                 170                 175

Lys Leu Asn Leu Asn Leu Ala Ile Asn Lys Arg Asp Ser Thr Ile Lys
            180                 185                 190

Arg Ala Leu Gln Asn Glu Phe Thr Arg Asn Ile Glu Tyr Met Ser Glu
        195                 200                 205

Gly Phe Gly Glu Leu Cys Asp Trp Lys Glu Ile Ile Lys Leu His Gln
    210                 215                 220

Arg Gln Asn Gly Ser Leu Phe Asp Ser Pro Ala Thr Thr Ala Ala Ala
225                 230                 235                 240
```

```
Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
    290                 295                 300

Arg Leu Trp Gln Gln Lys Asn Glu Glu Ile Phe Ser Asn Val Thr His
305                 310                 315                 320

Cys Ala Met Ala Phe Arg Leu Leu Arg Ile Ser Tyr Tyr Asp Val Ser
                325                 330                 335

Ser Asp Glu Leu Ala Glu Phe Val Asp Glu Glu His Phe Phe Ala Thr
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
    370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Asn
                405                 410                 415

Phe Tyr Ile Ile Ser Asp Leu Ala Glu Asn Arg Arg Tyr Ile Lys Ser
            420                 425                 430

Tyr Glu Glu Asn Asn Phe Lys Ile Leu Lys Ala Ala Tyr Arg Ser Pro
        435                 440                 445

Asn Ile Asn Asn Lys Asp Leu Phe Ile Phe Ser Ile Arg Asp Phe Glu
    450                 455                 460

Leu Cys Gln Ala Gln His Gln Glu Leu Gln Gln Leu Lys Arg Trp
465                 470                 475                 480

Phe Glu Asp Cys Arg Leu Asp Gln Leu Gly Leu Ser Glu Gln Phe Ile
                485                 490                 495

Ser Ala Ser Tyr Leu Cys Ala Ile Pro Ile Val Pro Gly Pro Glu Leu
            500                 505                 510

Ser Asp Ala Arg Leu Val Tyr Ala Lys Tyr Val Met Leu Leu Thr Ile
        515                 520                 525

Val Asp Asp His Phe Glu Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560

Lys Ser Glu Arg Val Lys Val Leu Phe Ser Met Phe Tyr Lys Ser Ile
                565                 570                 575

Glu Glu Ile Ala Thr Ile Ala Glu Ile Lys Gln Gly Arg Ser Val Lys
            580                 585                 590

Asn His Leu Ile Asn Leu Trp Leu Lys Val Met Lys Leu Met Leu Met
        595                 600                 605

Glu Arg Val Glu Trp Cys Ser Gly Lys Thr Ile Pro Arg Ile Glu Glu
    610                 615                 620

Tyr Leu Tyr Val Ser Ser Ile Thr Phe Gly Ser Arg Leu Ile Pro Leu
625                 630                 635                 640

Thr Thr Gln Tyr Phe Ile Gly Ile Lys Ile Ser Lys Asp Leu Leu Glu
                645                 650                 655
```

```
Ser Asp Glu Ile Tyr Gly Leu Cys Asn Phe Thr Gly Ile Val Leu Arg
            660                 665                 670

Leu Leu Asn Asp Leu Gln Asp Ser Lys Arg Glu Gln Lys Glu Gly Ser
        675                 680                 685

Ile Asn Leu Val Thr Leu Leu Met Lys Ser Ile Ser Glu Glu Glu Ala
    690                 695                 700

Ile Met Lys Met Lys Glu Ile Leu Glu Met Lys Arg Arg Glu Leu Phe
705                 710                 715                 720

Lys Met Val Leu Val Gln Lys Lys Gly Ser Gln Leu Pro Gln Leu Cys
                725                 730                 735

Lys Glu Ile Phe Trp Arg Thr Cys Lys Trp Ala His Phe Thr Tyr Ser
            740                 745                 750

Gln Thr Asp Arg Tyr Arg Phe Pro Glu Glu Met Glu Asn His Ile Asp
        755                 760                 765

Glu Val Phe Tyr Lys Pro Leu Asn His
    770                 775

<210> SEQ ID NO 7
<211> LENGTH: 2214
<212> TYPE: DNA
<213> ORGANISM: Solanum habrochaites

<400> SEQUENCE: 7
```

| | | | | | |
|---|---|---|---|---|---|
| ggatccatga | atggttttga | agatgcccgt | gaccgtatcc | gtgaatcgtt | tggtaaagtg | 60 |
| gaactgagcc | cgtcctcgta | tgacaccgcc | tgggttgcaa | tggtcccgtc | aaaacattcg | 120 |
| ctgaacgaac | cgtgctttcc | gcaatgtctg | gattggatta | cgaaaaacca | gcgtgaagac | 180 |
| ggcagctggg | gtctgaatcc | gtctcacccg | ctgctgctga | agatagcct | gagctctacc | 240 |
| ctggcctgtc | tgctggcact | gacgaaatgg | cgtgtgggcg | acgaacagat | taaacgcggc | 300 |
| ctgggtttta | tcgaaaccca | aagctgggcg | atcgataaca | aagaccagat | ttctccgctg | 360 |
| ggttttgaaa | ttatcttccc | gagtatgatc | aaatccgccg | aaaaactgaa | cctgaatctg | 420 |
| gcaattaata | acgtgatag | taccatcaaa | cgcgccctgc | agaacgaatt | cacgcgtaac | 480 |
| atcgaataca | tgtccgaagg | cttcggtgaa | ctgtgcgatt | ggaaagaaat | tatcaaactg | 540 |
| caccagcgcc | aaaacggctc | actgtttgat | tcgccggcaa | ccacggcagc | agcactgatc | 600 |
| tatcatcagc | acgacaaaaa | atgttacgaa | tacctgaact | caatcctgca | gcaacataaa | 660 |
| aattgggttc | cgaccatgta | cccgacgaaa | attcactcgc | tgctgtgcct | ggtcgatacc | 720 |
| ctgcagaatc | tgggtgtgca | tcgtcacttt | aaaagcgaaa | tcaaaaaagc | cctggatgaa | 780 |
| atctatcgcc | tgtggcagca | gaaaaacgaa | gaaatcttta | gcaatgtgac | ccattgtgcc | 840 |
| atggcattcc | gtctgctgcg | catttcttat | tacgatgtta | gttccgacga | actggctgaa | 900 |
| ttcgtcgatg | aagaacattt | ctttgcgacc | agcggcaaat | acacgtctca | tgttgaaatc | 960 |
| ctggaactgc | acaaagctag | ccaactggcg | attgatcacg | aaaaagatga | catcctggac | 1020 |
| aaaattaaca | attggacccg | tacgtttatg | gaacagaaac | tgctgaacaa | cggtttcatc | 1080 |
| gatcgtatga | gtaaaaaaga | agtggaactg | gccctgcgca | acttttatat | tatcagtgac | 1140 |
| ctggcagaaa | atcgtcgcta | catcaaatcc | tacgaagaaa | acaacttcaa | aatcctgaaa | 1200 |
| gctgcgtacc | gttcaccgaa | catcaacaac | aaagacctgt | ttatcttctc | gattcgcgac | 1260 |
| tttgaactgt | gccaggcgca | acatcaggaa | gaactgcagc | aactgaaacg | ttggtttgaa | 1320 |
| gattgtcgcc | tggaccaact | gggcctgtcc | gaacagttca | tcagcgcctc | ttatctgtgc | 1380 |
| gcaattccga | tcgttccggg | tccggaactg | tctgatgctc | gcctggtgta | tgcgaaatac | 1440 |

-continued

```
gttatgctgc tgaccattgt cgatgaccac tttgaaagct tcgcttctac ggatgaatgc    1500
ctgaatatta tcgaactggt ggaacgttgg gatgactatg cgagtgttgg ctacaaatcc    1560
gaacgcgtga agttctgtt ttcaatgttc tacaaatcga tcgaagaaat tgctaccatc    1620
gcggaaatta acagggccg tagcgtcaaa accatctga ttaatctgtg ctgaaagtc       1680 atgaaactga tgctgatgga acgtgtggaa tggtgttctg gtaaaaccat cccgcgcatt    1740
gaagaatatc tgtacgtttc atcgattacg tttggcagtc gcctgatccc gctgaccacg    1800
cagtacttca tcggtatcaa aatcagtaaa gatctgctgg aatccgacga atttacggc    1860 ctgtgcaact ttaccggtat cgtgctgcgt ctgctgaatg atctgcaaga ctcaaaacgc    1920
gaacagaaag aaggctcgat taatctggtt acgctgctga tgaaaagtat ctccgaagaa    1980
gaagcgatca tgaaaatgaa agaaatcctg gaaatgaaac gtcgcgaact gttcaaaatg    2040
gtcctggtgc agaaaaaagg tagccaactg ccgcagctgt gcaagaaat cttttggcgc     2100 acctgtaaat gggcccattt cacctatagc cagacggatc gttaccgctt cccggaagaa    2160
atggaaaatc acattgacga agtgttctac aaaccgctga atcattgagt cgac          2214
```

<210> SEQ ID NO 8
<211> LENGTH: 733
<212> TYPE: PRT
<213> ORGANISM: Solanum habrochaites

<400> SEQUENCE: 8

```
Met Asn Gly Phe Glu Asp Ala Arg Asp Arg Ile Arg Glu Ser Phe Gly
 1               5                   10                  15

Lys Val Glu Leu Ser Pro Ser Ser Tyr Asp Thr Ala Trp Val Ala Met
                20                  25                  30

Val Pro Ser Lys His Ser Leu Asn Glu Pro Cys Phe Pro Gln Cys Leu
            35                  40                  45

Asp Trp Ile Ile Glu Asn Gln Arg Glu Asp Gly Ser Trp Gly Leu Asn
        50                  55                  60

Pro Ser His Pro Leu Leu Lys Asp Ser Leu Ser Ser Thr Leu Ala
65                  70                  75                  80

Cys Leu Leu Ala Leu Thr Lys Trp Arg Val Gly Asp Glu Gln Ile Lys
                85                  90                  95

Arg Gly Leu Gly Phe Ile Glu Thr Gln Ser Trp Ala Ile Asp Asn Lys
            100                 105                 110

Asp Gln Ile Ser Pro Leu Gly Phe Glu Ile Ile Phe Pro Ser Met Ile
        115                 120                 125

Lys Ser Ala Glu Lys Leu Asn Leu Asn Leu Ala Ile Asn Lys Arg Asp
    130                 135                 140

Ser Thr Ile Lys Arg Ala Leu Gln Asn Glu Phe Thr Arg Asn Ile Glu
145                 150                 155                 160

Tyr Met Ser Glu Gly Phe Gly Glu Leu Cys Asp Trp Lys Glu Ile Ile
                165                 170                 175

Lys Leu His Gln Arg Gln Asn Gly Ser Leu Phe Asp Ser Pro Ala Thr
            180                 185                 190

Thr Ala Ala Ala Leu Ile Tyr His Gln His Asp Lys Lys Cys Tyr Glu
        195                 200                 205

Tyr Leu Asn Ser Ile Leu Gln Gln His Lys Asn Trp Val Pro Thr Met
    210                 215                 220

Tyr Pro Thr Lys Ile His Ser Leu Leu Cys Leu Val Asp Thr Leu Gln
225                 230                 235                 240
```

```
Asn Leu Gly Val His Arg His Phe Lys Ser Glu Ile Lys Lys Ala Leu
                245                 250                 255

Asp Glu Ile Tyr Arg Leu Trp Gln Gln Lys Asn Glu Glu Ile Phe Ser
            260                 265                 270

Asn Val Thr His Cys Ala Met Ala Phe Arg Leu Leu Arg Ile Ser Tyr
        275                 280                 285

Tyr Asp Val Ser Ser Asp Glu Leu Ala Glu Phe Val Asp Glu Glu His
    290                 295                 300

Phe Phe Ala Thr Ser Gly Lys Tyr Thr Ser His Val Glu Ile Leu Glu
305                 310                 315                 320

Leu His Lys Ala Ser Gln Leu Ala Ile Asp His Glu Lys Asp Asp Ile
                325                 330                 335

Leu Asp Lys Ile Asn Asn Trp Thr Arg Thr Phe Met Glu Gln Lys Leu
            340                 345                 350

Leu Asn Asn Gly Phe Ile Asp Arg Met Ser Lys Lys Glu Val Glu Leu
        355                 360                 365

Ala Leu Arg Asn Phe Tyr Ile Ile Ser Asp Leu Ala Glu Asn Arg Arg
    370                 375                 380

Tyr Ile Lys Ser Tyr Glu Glu Asn Asn Phe Lys Ile Leu Lys Ala Ala
385                 390                 395                 400

Tyr Arg Ser Pro Asn Ile Asn Asn Lys Asp Leu Phe Ile Phe Ser Ile
                405                 410                 415

Arg Asp Phe Glu Leu Cys Gln Ala Gln His Gln Glu Glu Leu Gln Gln
            420                 425                 430

Leu Lys Arg Trp Phe Glu Asp Cys Arg Leu Asp Gln Leu Gly Leu Ser
        435                 440                 445

Glu Gln Phe Ile Ser Ala Ser Tyr Leu Cys Ala Ile Pro Ile Val Pro
    450                 455                 460

Gly Pro Glu Leu Ser Asp Ala Arg Leu Val Tyr Ala Lys Tyr Val Met
465                 470                 475                 480

Leu Leu Thr Ile Val Asp Asp His Phe Glu Ser Phe Ala Ser Thr Asp
                485                 490                 495

Glu Cys Leu Asn Ile Ile Glu Leu Val Glu Arg Trp Asp Asp Tyr Ala
            500                 505                 510

Ser Val Gly Tyr Lys Ser Glu Arg Val Lys Val Leu Phe Ser Met Phe
        515                 520                 525

Tyr Lys Ser Ile Glu Glu Ile Ala Thr Ile Ala Glu Ile Lys Gln Gly
    530                 535                 540

Arg Ser Val Lys Asn His Leu Ile Asn Leu Trp Leu Lys Val Met Lys
545                 550                 555                 560

Leu Met Leu Met Glu Arg Val Glu Trp Cys Ser Gly Lys Thr Ile Pro
                565                 570                 575

Arg Ile Glu Glu Tyr Leu Tyr Val Ser Ser Ile Thr Phe Gly Ser Arg
            580                 585                 590

Leu Ile Pro Leu Thr Thr Gln Tyr Phe Ile Gly Ile Lys Ile Ser Lys
        595                 600                 605

Asp Leu Leu Glu Ser Asp Glu Ile Tyr Gly Leu Cys Asn Phe Thr Gly
    610                 615                 620

Ile Val Leu Arg Leu Leu Asn Asp Leu Gln Asp Ser Lys Arg Glu Gln
625                 630                 635                 640

Lys Glu Gly Ser Ile Asn Leu Val Thr Leu Leu Met Lys Ser Ile Ser
                645                 650                 655
```

```
Glu Glu Glu Ala Ile Met Lys Met Lys Glu Ile Leu Glu Met Lys Arg
                660                 665                 670

Arg Glu Leu Phe Lys Met Val Leu Val Gln Lys Lys Gly Ser Gln Leu
            675                 680                 685

Pro Gln Leu Cys Lys Glu Ile Phe Trp Arg Thr Cys Lys Trp Ala His
        690                 695                 700

Phe Thr Tyr Ser Gln Thr Asp Arg Tyr Arg Phe Pro Glu Glu Met Glu
705                 710                 715                 720

Asn His Ile Asp Glu Val Phe Tyr Lys Pro Leu Asn His
                725                 730

<210> SEQ ID NO 9
<211> LENGTH: 472
<212> TYPE: PRT
<213> ORGANISM: Solanum habrochaites

<400> SEQUENCE: 9

Met Ile Val Gly Tyr Arg Ser Thr Ile Ile Thr Leu Ser His Pro Lys
  1               5                  10                  15

Leu Gly Asn Gly Lys Thr Ile Ser Ser Asn Ala Ile Phe Gln Arg Ser
             20                  25                  30

Cys Arg Val Arg Cys Ser His Ser Thr Thr Ser Ser Met Asn Gly Phe
         35                  40                  45

Glu Asp Ala Arg Asp Arg Ile Arg Glu Ser Phe Gly Lys Leu Glu Leu
     50                  55                  60

Ser Pro Ser Ser Tyr Asp Thr Ala Trp Val Ala Met Val Pro Ser Arg
 65                  70                  75                  80

His Ser Leu Asn Glu Pro Cys Phe Pro Gln Cys Leu Asp Trp Ile Ile
                 85                  90                  95

Glu Asn Gln Arg Glu Asp Gly Ser Trp Gly Leu Asn Pro Thr His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Tyr Gly Trp Ala Val Asp Asn Lys Asp Gln Ile Ser
145                 150                 155                 160

Pro Leu Gly Phe Glu Val Ile Phe Ser Ser Met Ile Lys Ser Ala Glu
                165                 170                 175

Lys Leu Asp Leu Asn Leu Pro Leu Asn Leu His Leu Val Asn Leu Val
            180                 185                 190

Lys Cys Lys Arg Asp Ser Thr Ile Lys Arg Asn Val Glu Tyr Met Gly
        195                 200                 205

Glu Gly Val Gly Glu Leu Cys Asp Trp Lys Glu Met Ile Lys Leu His
    210                 215                 220

Gln Arg Gln Asn Gly Ser Leu Phe Asp Ser Pro Ala Thr Thr Ala Ala
225                 230                 235                 240

Ala Leu Ile Tyr His Gln His Asp Gln Lys Cys Tyr Gln Tyr Leu Asn
                245                 250                 255

Ser Ile Phe Gln Gln His Lys Asn Trp Val Pro Thr Met Tyr Pro Thr
            260                 265                 270

Lys Val His Ser Leu Leu Cys Leu Val Asp Thr Leu Gln Asn Leu Gly
        275                 280                 285

Val His Arg His Phe Lys Ser Glu Ile Lys Lys Ala Leu Asp Glu Ile
    290                 295                 300
```

```
Tyr Arg Leu Trp Gln Gln Lys Asn Glu Gln Ile Phe Ser Asn Val Thr
305                 310                 315                 320

His Cys Ala Met Ala Phe Arg Leu Leu Arg Met Ser Tyr Tyr Asp Val
                325                 330                 335

Ser Ser Asp Glu Leu Ala Glu Phe Val Asp Glu Glu His Phe Phe Ala
            340                 345                 350

Thr Asn Gly Lys Tyr Lys Ser His Val Glu Ile Leu Glu Leu His Lys
        355                 360                 365

Ala Ser Gln Leu Ala Ile Asp His Glu Lys Asp Asp Ile Leu Asp Lys
370                 375                 380

Ile Asn Asn Trp Thr Arg Ala Phe Met Glu Gln Lys Leu Leu Asn Asn
385                 390                 395                 400

Gly Phe Ile Asp Arg Met Ser Lys Lys Glu Val Glu Leu Ala Leu Arg
                405                 410                 415

Lys Phe Tyr Thr Thr Ser His Leu Ala Glu Asn Arg Arg Tyr Ile Lys
            420                 425                 430

Ser Tyr Glu Glu Asn Asn Phe Lys Ile Leu Lys Ala Ala Tyr Arg Ser
        435                 440                 445

Pro Asn Ile Asn Asn Lys Asp Leu Leu Ala Phe Ser Ile His Asp Phe
    450                 455                 460

Glu Leu Cys Gln Ala Gln His Arg
465                 470

<210> SEQ ID NO 10
<211> LENGTH: 471
<212> TYPE: PRT
<213> ORGANISM: Solanum habrochaites

<400> SEQUENCE: 10

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Gln Arg Ser
                20                  25                  30

Cys Arg Val Arg Cys Ser His Ser Thr Pro Ser Ser Met Asn Gly Phe
            35                  40                  45

Glu Asp Ala Arg Asp Arg Ile Arg Glu Ser Phe Gly Lys Val Glu Leu
        50                  55                  60

Ser Pro Ser Ser Tyr Asp Thr Ala Trp Val Ala Met Val Pro Ser Lys
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Ser His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
                165                 170                 175

Lys Leu Asn Leu Asn Leu Ala Ile Asn Lys Arg Asp Ser Thr Ile Lys
            180                 185                 190

Arg Ala Leu Gln Asn Glu Phe Thr Arg Asn Ile Glu Tyr Met Ser Glu
```

```
                    195                 200                 205
Gly Val Gly Glu Leu Cys Asp Trp Lys Glu Ile Ile Lys Leu His Gln
    210                 215                 220

Arg Gln Asn Gly Ser Leu Phe Asp Ser Pro Ala Thr Thr Ala Ala Ala
225                 230                 235                 240

Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Ala Leu Asp Glu Ile Tyr
    290                 295                 300

Arg Leu Trp Gln Gln Lys Asn Glu Gln Ile Phe Ser Asn Val Thr His
305                 310                 315                 320

Cys Ala Met Ala Phe Arg Leu Leu Arg Met Ser Tyr Tyr Asp Val Ser
                325                 330                 335

Ser Asp Glu Leu Ala Glu Phe Val Asp Glu His Phe Phe Ala Ile
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Ile Leu Asp Lys Ile
    370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Lys
                405                 410                 415

Phe Tyr Thr Ile Ser Asp Leu Ala Glu Asn Arg Arg Cys Ile Lys Ser
            420                 425                 430

Tyr Glu Glu Asn Asn Phe Lys Ile Leu Lys Ala Ala Tyr Arg Ser Pro
        435                 440                 445

Asn Ile Tyr Asn Lys Asp Leu Phe Ile Phe Ser Ile Arg Asn Phe Glu
    450                 455                 460

Leu Cys Gln Ala Gln His Gln
465                 470

<210> SEQ ID NO 11
<211> LENGTH: 732
<212> TYPE: PRT
<213> ORGANISM: Solanum habrochaites

<400> SEQUENCE: 11

Asn Gly Phe Glu Asp Ala Arg Asp Arg Ile Arg Glu Ser Phe Gly Lys
1               5                   10                  15

Val Glu Leu Ser Pro Ser Ser Tyr Asp Thr Ala Trp Val Ala Met Val
            20                  25                  30

Pro Ser Lys His Ser Leu Asn Glu Pro Cys Phe Pro Gln Cys Leu Asp
        35                  40                  45

Trp Ile Ile Glu Asn Gln Arg Glu Asp Gly Ser Trp Gly Leu Asn Pro
    50                  55                  60

Ser His Pro Leu Leu Leu Lys Asp Ser Leu Ser Ser Thr Leu Ala Cys
65                  70                  75                  80

Leu Leu Ala Leu Thr Lys Trp Arg Val Gly Asp Glu Gln Ile Lys Arg
                85                  90                  95
```

Gly Leu Gly Phe Ile Glu Thr Gln Ser Trp Ala Ile Asp Asn Lys Asp
            100                 105                 110

Gln Ile Ser Pro Leu Gly Phe Glu Ile Ile Phe Pro Ser Met Ile Lys
        115                 120                 125

Ser Ala Glu Lys Leu Asn Leu Asn Leu Ala Ile Asn Lys Arg Asp Ser
130                 135                 140

Thr Ile Lys Arg Ala Leu Gln Asn Glu Phe Thr Arg Asn Ile Glu Tyr
145                 150                 155                 160

Met Ser Glu Gly Phe Gly Glu Leu Cys Asp Trp Lys Glu Ile Ile Lys
                165                 170                 175

Leu His Gln Arg Gln Asn Gly Ser Leu Phe Asp Ser Pro Ala Thr Thr
            180                 185                 190

Ala Ala Ala Leu Ile Tyr His Gln His Asp Lys Lys Cys Tyr Glu Tyr
        195                 200                 205

Leu Asn Ser Ile Leu Gln Gln His Lys Asn Trp Val Pro Thr Met Tyr
210                 215                 220

Pro Thr Lys Ile His Ser Leu Leu Cys Leu Val Asp Thr Leu Gln Asn
225                 230                 235                 240

Leu Gly Val His Arg His Phe Lys Ser Glu Ile Lys Lys Ala Leu Asp
                245                 250                 255

Glu Ile Tyr Arg Leu Trp Gln Gln Lys Asn Glu Glu Ile Phe Ser Asn
            260                 265                 270

Val Thr His Cys Ala Met Ala Phe Arg Leu Leu Arg Ile Ser Tyr Tyr
        275                 280                 285

Asp Val Ser Ser Asp Glu Leu Ala Glu Phe Val Asp Glu His Phe
290                 295                 300

Phe Ala Thr Ser Gly Lys Tyr Thr Ser His Val Glu Ile Leu Glu Leu
305                 310                 315                 320

His Lys Ala Ser Gln Leu Ala Ile Asp His Glu Lys Asp Asp Ile Leu
                325                 330                 335

Asp Lys Ile Asn Asn Trp Thr Arg Thr Phe Met Glu Gln Lys Leu Leu
            340                 345                 350

Asn Asn Gly Phe Ile Asp Arg Met Ser Lys Lys Glu Val Glu Leu Ala
        355                 360                 365

Leu Arg Asn Phe Tyr Ile Ile Ser Asp Leu Ala Glu Asn Arg Arg Tyr
370                 375                 380

Ile Lys Ser Tyr Glu Glu Asn Asn Phe Lys Ile Leu Lys Ala Ala Tyr
385                 390                 395                 400

Arg Ser Pro Asn Ile Asn Asn Lys Asp Leu Phe Ile Phe Ser Ile Arg
                405                 410                 415

Asp Phe Glu Leu Cys Gln Ala Gln His Gln Glu Glu Leu Gln Gln Leu
            420                 425                 430

Lys Arg Trp Phe Glu Asp Cys Arg Leu Asp Gln Leu Gly Leu Ser Glu
        435                 440                 445

Gln Phe Ile Ser Ala Ser Tyr Leu Cys Ala Ile Pro Ile Val Pro Gly
450                 455                 460

Pro Glu Leu Ser Asp Ala Arg Leu Val Tyr Ala Lys Tyr Val Met Leu
465                 470                 475                 480

Leu Thr Ile Val Asp Asp His Phe Glu Ser Phe Ala Ser Thr Asp Glu
                485                 490                 495

Cys Leu Asn Ile Ile Glu Leu Val Glu Arg Trp Asp Asp Tyr Ala Ser
            500                 505                 510

Val Gly Tyr Lys Ser Glu Arg Val Lys Val Leu Phe Ser Met Phe Tyr

```
            515                 520                 525
Lys Ser Ile Glu Glu Ile Ala Thr Ile Ala Glu Ile Lys Gln Gly Arg
    530                 535                 540

Ser Val Lys Asn His Leu Ile Asn Leu Trp Leu Lys Val Met Lys Leu
545                 550                 555                 560

Met Leu Met Glu Arg Val Glu Trp Cys Ser Gly Lys Thr Ile Pro Arg
                565                 570                 575

Ile Glu Glu Tyr Leu Tyr Val Ser Ser Ile Thr Phe Gly Ser Arg Leu
            580                 585                 590

Ile Pro Leu Thr Thr Gln Tyr Phe Ile Gly Ile Lys Ile Ser Lys Asp
        595                 600                 605

Leu Leu Glu Ser Asp Glu Ile Tyr Gly Leu Cys Asn Phe Thr Gly Ile
    610                 615                 620

Val Leu Arg Leu Leu Asn Asp Leu Gln Asp Ser Lys Arg Glu Gln Lys
625                 630                 635                 640

Glu Gly Ser Ile Asn Leu Val Thr Leu Leu Met Lys Ser Ile Ser Glu
                645                 650                 655

Glu Glu Ala Ile Met Lys Met Lys Glu Ile Leu Glu Met Lys Arg Arg
            660                 665                 670

Glu Leu Phe Lys Met Val Leu Val Gln Lys Gly Ser Gln Leu Pro
        675                 680                 685

Gln Leu Cys Lys Glu Ile Phe Trp Arg Thr Cys Lys Trp Ala His Phe
    690                 695                 700

Thr Tyr Ser Gln Thr Asp Arg Tyr Arg Phe Pro Glu Glu Met Glu Asn
705                 710                 715                 720

His Ile Asp Glu Val Phe Tyr Lys Pro Leu Asn His
                725                 730

<210> SEQ ID NO 12
<211> LENGTH: 777
<212> TYPE: PRT
<213> ORGANISM: Solanum habrochaites

<400> SEQUENCE: 12

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Arg Arg Ser
            20                  25                  30

Cys Arg Val Arg Cys Ser His Ser Thr Pro Ser Ser Met Asn Gly Phe
        35                  40                  45

Glu Asp Ala Arg Asp Arg Ile Arg Glu Ser Phe Gly Lys Val Glu Leu
    50                  55                  60

Ser Pro Ser Ser Tyr Asp Thr Ala Trp Val Ala Met Val Pro Ser Lys
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Ser His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Gln Ser Trp Ala Ile Asp Asn Lys Asp Gln Ile Ser
145                 150                 155                 160
```

```
Pro Leu Gly Phe Glu Ile Ile Phe Pro Ser Met Ile Lys Ser Ala Glu
            165                 170                 175

Lys Leu Asn Leu Asn Leu Ala Ile Asn Lys Arg Asp Ser Thr Ile Lys
        180                 185                 190

Arg Ala Leu Gln Asn Glu Phe Thr Arg Asn Ile Glu Tyr Met Ser Glu
        195                 200                 205

Gly Phe Gly Glu Leu Cys Asp Trp Lys Glu Ile Met Lys Leu His Gln
    210                 215                 220

Arg Gln Asn Gly Ser Leu Phe Asp Ser Pro Ala Thr Ala Ala Ala
225                 230                 235                 240

Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
    290                 295                 300

Arg Leu Trp Gln Gln Lys Asn Glu Glu Ile Phe Ser Asn Val Thr His
305                 310                 315                 320

Cys Ala Met Val Phe Arg Leu Leu Arg Ile Ser Tyr Tyr Asp Val Ser
                325                 330                 335

Ser Asp Glu Leu Ala Glu Phe Val Asp Glu His Phe Phe Ala Thr
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
        370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Asn
                405                 410                 415

Phe Tyr Ile Ile Ser Asp Leu Ala Glu Asn Arg Arg Tyr Ile Lys Ser
            420                 425                 430

Tyr Glu Glu Asn Asn Phe Lys Ile Leu Lys Ala Ala Tyr Arg Ser Pro
        435                 440                 445

Asn Ile Asn Asn Lys Asp Leu Phe Ile Phe Ser Ile Arg Asp Phe Glu
    450                 455                 460

Leu Cys Gln Ala Gln His Gln Glu Leu Gln Gln Leu Lys Arg Trp
465                 470                 475                 480

Phe Glu Asp Cys Arg Leu Asp Gln Leu Gly Leu Ser Glu Gln Phe Ile
                485                 490                 495

Ser Ala Ser Tyr Leu Cys Ala Ile Pro Ile Val Pro Gly Pro Glu Leu
            500                 505                 510

Ser Asp Ala Arg Leu Val Tyr Ala Lys Tyr Val Met Leu Leu Thr Ile
        515                 520                 525

Val Asp Asp His Phe Glu Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560

Lys Ser Glu Arg Val Lys Val Leu Phe Ser Met Phe Tyr Lys Ser Ile
                565                 570                 575

Glu Glu Ile Ala Thr Ile Ala Glu Ile Lys Gln Gly Arg Ser Val Lys
```

```
               580                 585                 590
Asn His Leu Ile Asn Leu Trp Leu Lys Val Met Lys Leu Met Leu Met
            595                 600                 605

Glu Arg Val Glu Trp Cys Ser Gly Lys Thr Ile Pro Arg Ile Glu Glu
        610                 615                 620

Tyr Leu Tyr Val Ser Ser Ile Thr Phe Gly Ser Arg Leu Ile Pro Leu
625                 630                 635                 640

Thr Thr Gln Tyr Phe Leu Gly Ile Lys Ile Ser Lys Asp Leu Leu Glu
                645                 650                 655

Ser Asp Glu Ile Tyr Gly Leu Cys Asn Phe Thr Gly Ile Val Leu Arg
            660                 665                 670

Leu Leu Asn Asp Leu Gln Asp Ser Lys Arg Glu Gln Lys Glu Gly Ser
        675                 680                 685

Ile Asn Leu Val Thr Leu Leu Met Lys Ser Ile Ser Glu Glu Glu Ala
            690                 695                 700

Ile Met Lys Met Lys Glu Ile Leu Glu Met Lys Arg Arg Glu Leu Phe
705                 710                 715                 720

Lys Met Val Leu Val Gln Lys Lys Gly Ser Gln Leu Pro Gln Leu Cys
                725                 730                 735

Lys Glu Ile Phe Trp Arg Thr Cys Lys Trp Ala His Phe Thr Tyr Ser
            740                 745                 750

Gln Thr Asp Arg Tyr Arg Phe Pro Glu Glu Met Glu Asn His Ile Asp
        755                 760                 765

Glu Val Phe Tyr Lys Pro Leu Asn His
770                 775
```

<210> SEQ ID NO 13
<211> LENGTH: 2334
<212> TYPE: DNA
<213> ORGANISM: Solanum habrochaites

<400> SEQUENCE: 13

```
atgatagttg ctatagaag cacaatcata acccttctc atcctaagct aggcaatggg        60
aaaacaattt catccaatgc aattttccgg agatcatgta gagtaagatg cagccacagt      120
accccttcat caatgaatgg ttttgaagat gcaagggata gaataaggga aagttttggg      180
aaagtagagt tatctccttc ttcctatgac acagcatggg tagctatggt cccttcaaaa      240
cattcactaa atgagccatg ttttccacaa tgtttggatt ggattattga aaatcaaaga      300
gaagatggaa cttggggact aaaccctagc catccattgc ttctcaagga ctcacttttct    360 tccactcttg catgtttgct tgcactaacc aaatggagag ttggagatga gcaaatcaaa      420
agaggccttg gctttattga aacccagagt tgggcaattg ataacaagga tcaaatttca      480
cctctaggat ttgaaattat atttcccagt atgatcaagt ctgcagaaaa actaaactta      540
aatctagcaa ttaacaaaag agattcaaca attaaaagag cattcagaa tgagttcacg       600 aggaatattg aatatatgag tgaaggattt ggtgaattat gtgattggaa ggaaataatg      660
aagttacatc aaaggcaaaa tggttcatta tttgattcac cagccactac tgcagctgcc      720
ttgatttacc atcagcatga taaaaaatgc tatgaatatc ttaattcaat cttgcaacaa      780
cacaaaaatt gggttccac tatgtatcca acaagatac attcattgct ttgcttggtt       840
gatacacttc aaaatcttgg agtacatcgg cattttaaat cagaaataaa gaaagcccta      900
gatgaaatat acaggctatg gcaacaaaag aatgaagaaa ttttctcaaa tgtcacccat      960
tgtgctatgg tttttcgact tctaaggata agctactatg atgtctcctc agatgaacta    1020
```

```
gcagaatttg tggatgaaga acatttcttt gcaacaagtg ggaaatatac aagtcatgtt    1080
gaaattcttg aactccacaa agcatcacaa ttggctattg atcatgagaa agatgacatt    1140
ttggataaga ttaacaattg gacaagaaca tttatggagc aaaaactctt aaacaatggc    1200
ttcatagata ggatgtcaaa aaaggaggtg aacttgctt tgaggaattt ttatatcata     1260
tctgatctag cagaaaatag aagatatata aagtcatacg aagagaacaa ttttaaaatc    1320
ttaaaagcag cttataggtc acctaacatt aacaataagg acttgtttat attttcaata    1380
cgcgactttg aattatgcca agctcaacac caagaagaac ttcaacaact caagaggtgg    1440
tttgaagatt gtagattgga ccaactcgga ctttcggaac aatttatatc tgctagttac    1500
ttatgtgcta ttcctattgt ccccgggcct gaattatccg atgctcgtct cgtgtacgcg    1560
aaatacgtca tgctcttgac tattgtcgat gatcatttcg agagttttgc atctacagat    1620
gaatgtctca acatcattga attagtagaa aggtgggatg actatgcaag tgtaggttat    1680
aaatctgaga gggttaaagt tttattttca atgttttaca aatcaataga ggagattgca    1740
acaattgctg aaattaaaca aggacgatct gtcaaaaatc accttattaa tttgtggctt    1800
aaagtgatga agttgatgtt gatggaacga gtagagtggt gttctggcaa gacaatacca    1860
agaatagaag agtatttgta tgttagttct ataacatttg gttcaagatt gattcctctc    1920
acaacacaat attttcttgg aataaaaata tccaaagatc ttttagaaag tgatgaaatt    1980
tatggtttat gcaattttac cggtatagtc ttgaggctcc tcaatgattt acaagattcc    2040
aagagagaac aaaaggaggg ctcaataaat ttagtcacat tactaatgaa aagtatctct    2100
gaggaagaag ctataatgaa gatgaaggaa atcttggaaa tgaaagaag agagttattt     2160 aaaatggttt tagttcaaaa aaagggaagc caattgcctc aattatgcaa agaaatattt    2220
tggaggacat gcaaatgggc tcatttcact tattcacaaa ctgatagata tagatttcca    2280
gaggaaatgg agaatcacat tgatgaagtc ttttacaaac cactcaatca ttaa           2334
```

<210> SEQ ID NO 14
<211> LENGTH: 777
<212> TYPE: PRT
<213> ORGANISM: Solanum habrochaites

<400> SEQUENCE: 14

```
Met Ile Val Gly Tyr Arg Ser Thr Ile Ile Ile Leu Ser His Pro Lys
  1               5                  10                  15

Leu Gly Asn Gly Lys Thr Ile Ser Ser Asn Ala Ile Phe Gln Arg Ser
             20                  25                  30

Cys Arg Val Arg Cys Ser His Ser Thr Thr Ser Ser Met Asn Gly Phe
         35                  40                  45

Glu Asp Ala Arg Asp Arg Ile Arg Glu Ser Phe Gly Lys Leu Glu Leu
     50                  55                  60

Ser Pro Ser Ser Tyr Asp Thr Ala Trp Val Ala Met Val Pro Ser Asn
 65                  70                  75                  80

His Ser Leu Asn Glu Pro Cys Phe Pro Gln Cys Leu Asp Trp Ile Ile
                 85                  90                  95

Glu Asn Gln Arg Glu Asp Gly Ser Trp Gly Leu Asn Pro Ser His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140
```

```
Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
            165                 170                 175

Lys Leu Asn Leu Asn Leu Ala Ile Asn Lys Arg Asp Ser Thr Ile Lys
        180                 185                 190

Arg Ala Leu Gln Asn Glu Phe Thr Arg Asn Ile Glu Tyr Met Ser Glu
                195                 200                 205

Gly Val Gly Glu Leu Cys Asp Trp Lys Glu Ile Ile Lys Leu His Gln
210                 215                 220

Arg Gln Asn Gly Ser Leu Phe Asp Ser Pro Ala Thr Thr Ala Ala Ala
225                 230                 235                 240

Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
    290                 295                 300

Arg Leu Trp Gln Gln Lys Asn Glu Glu Ile Phe Ser Asn Val Thr His
305                 310                 315                 320

Cys Ala Met Ala Phe Arg Leu Leu Arg Ile Ser Tyr Tyr Asp Val Ser
                325                 330                 335

Ser Asp Glu Leu Ala Glu Phe Val Asp Glu His Phe Phe Ala Thr
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
    370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Asn
                405                 410                 415

Phe Tyr Ile Ile Ser Asp Leu Ala Glu Asn Arg Arg Tyr Ile Lys Ser
            420                 425                 430

Tyr Glu Glu Asn Asn Phe Lys Ile Leu Lys Ala Ala Tyr Arg Ser Pro
        435                 440                 445

Asn Ile Asn Asn Lys Asp Leu Phe Ile Phe Ser Ile Arg Asp Phe Glu
    450                 455                 460

Leu Cys Gln Ala Gln His Gln Glu Leu Gln Gln Leu Lys Arg Trp
465                 470                 475                 480

Phe Glu Asp Cys Arg Leu Asp Gln Leu Gly Leu Ser Glu Gln Phe Ile
                485                 490                 495

Ser Ala Ser Tyr Leu Cys Ala Ile Pro Ile Val Pro Gly Pro Glu Leu
            500                 505                 510

Ser Asp Ala Arg Leu Met Tyr Ala Lys Tyr Val Met Leu Leu Thr Ile
        515                 520                 525

Val Asp Asp His Phe Glu Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560
```

```
Lys Ser Glu Arg Val Lys Val Leu Phe Ser Met Phe Tyr Lys Ser Ile
            565                 570                 575
Glu Glu Ile Ala Thr Ile Ala Glu Ile Lys Gln Gly Arg Ser Val Lys
        580                 585                 590
Asn His Leu Ile Asn Leu Trp Leu Lys Val Met Lys Leu Met Leu Met
    595                 600                 605
Glu Arg Val Glu Trp Cys Ser Gly Lys Thr Ile Pro Arg Ile Glu Glu
610                 615                 620
Tyr Leu Tyr Val Thr Ser Ile Thr Phe Gly Ser Arg Leu Ile Pro Leu
625                 630                 635                 640
Thr Thr Gln Tyr Phe Leu Gly Ile Lys Ile Ser Lys Asp Leu Leu Glu
                645                 650                 655
Ser Asp Glu Ile Tyr Gly Leu Cys Asn Cys Thr Gly Ile Val Leu Arg
            660                 665                 670
Leu Leu Asn Asp Leu Gln Asp Ser Lys Arg Glu Gln Lys Glu Gly Ser
        675                 680                 685
Ile Asn Leu Val Thr Leu Leu Met Lys Ser Ile Ser Glu Glu Glu Ala
    690                 695                 700
Ile Met Lys Met Lys Glu Ile Leu Glu Met Lys Arg Arg Glu Leu Phe
705                 710                 715                 720
Lys Met Val Leu Val Gln Lys Lys Gly Ser Gln Leu Pro Gln Leu Cys
                725                 730                 735
Lys Glu Ile Phe Trp Arg Thr Cys Lys Trp Ala His Phe Thr Tyr Ser
            740                 745                 750
Gln Thr Asp Arg Tyr Arg Phe Pro Glu Glu Met Glu Asn His Ile Asp
        755                 760                 765
Glu Val Phe Tyr Lys Pro Leu Asn His
    770                 775
```

<210> SEQ ID NO 15
<211> LENGTH: 2334
<212> TYPE: DNA
<213> ORGANISM: Solanum habrochaites

<400> SEQUENCE: 15

```
atgatagttg gctatagaag cacaatcata atcctttctc atcctaagct aggcaatggg      60
aaaacaattt catccaatgc aattttccag agatcatgta gagtaagatg cagccacagt     120
accacttcat caatgaatgg tttcgaagat gcaagggata gaataaggga aagttttggg     180
aaattagagt tatctccttc ttcctatgac acagcatggg tagctatggt cccttcaaat     240
cattcactaa atgagccatg ttttccacaa tgtttggatt ggattattga aaatcaaaga     300
gaagatggat cttggggact aaaccctagc catccattgc ttctcaagga ctcacttttct    360
tccactcttg catgtttgct tgcactaacc aaatggagag ttggagatga gcaaatcaaa     420
agaggccttg gctttattga aacccagagt tgggcaattg ataacaagga tcaaatttca     480
cctctaggat ttgaaattat atttcccagt atgatcaagt ctgcagaaaa actaaactta     540
aatctagcaa ttaacaaaag agattcaaca attaaaagag cattgcagaa tgaattcacg     600
aggaatattg aatatatgag tgaaggagtt ggtgaattat gtgattggaa ggaaataata     660
aagttacatc aaaggcaaaa tggttcatta tttgattcac cagccactac tgcagctgcc     720
ttgatttacc atcagcatga taaaaaatgc tatgaatatc ttaattcaat cttgcaacaa     780
cacaaaaatt gggttcccac tatgtatcca acaaagatac attcattgct ttgcttggtt     840
gatacacttc aaaatcttgg agtacatcgg catttaaat cagaaataaa gaaagcccta     900
```

```
gatgaaatat acaggctatg caacaaaag aatgaagaaa ttttctcaaa tgtcacccat    960
tgtgctatgg cttttcgact tctaaggata agctactatg atgtctcctc ggatgaacta   1020
gcagaatttg tggatgaaga acatttttt gcaacaagtg ggaaatatac aagtcatgtt   1080
gaaattcttg aactccacaa agcatcacaa ttggctattg atcatgagaa agatgacatt   1140
ttggataaga ttaacaattg gacaagaaca tttatggagc aaaaactctt aaacaatggc   1200
ttcatagata ggatgtcaaa aaaggaggtg gaacttgctt tgaggaattt ttatatcata   1260
tctgatctag cagaaaatag aagatatata aagtcatacg aagagaacaa ttttaaaatc   1320
ttaaaagcag cttataggtc acctaacatt aacaataagg acttgtttat attttcaata   1380
cgcgactttg aattatgcca agctcaacac caagaagaac ttcaacaact caagaggtgg   1440
tttgaagatt gtagattgga ccaactcgga cttcggaac aatttatatc tgctagttac   1500
ttatgtgcta ttcctattgt ccccgggcct gaattatccg atgctcgtct catgtacgcg   1560
aaatacgtca tgctcttgac tattgtcgat gatcatttcg agagttttgc atctacagat   1620
gaatgtctca acatcattga attagtagaa aggtgggatg actatgcaag tgtaggttat   1680
aaatctgaga gggttaaagt tttattttca atgttttaca aatcaataga ggagattgca   1740
acaattgctg aaattaaaca aggacgatct gtcaaaaatc accttattaa tttgtggctt   1800
aaagtgatga agttgatgtt gatggaacga gtagagtggt gttctggcaa gacaatacca   1860
agaatagaag agtatttgta tgttacttct ataacatttg gttcaagatt gattcctctc   1920
acaacacaat attttcttgg aataaaaata tccaaagatc ttttagaaag tgatgaaatt   1980
tatggtttat gcaattgtac cggtatagtc ttgaggctcc tcaatgattt acaagattcc   2040
aagagagaac aaaaggaggg ctcaataaat ttagtcacat tactaatgaa aagtatctct   2100
gaggaagaag ctataatgaa gatgaaggaa atcttggaaa tgaaagaag agagttattt   2160
aaaatggttt tagttcaaaa aaagggaagc caattgcctc aattatgcaa agaaatattt   2220
tggaggacat gcaaatgggc tcatttcact tattcacaaa ctgatagata tagatttcca   2280
gaggaaatgg agaatcacat tgatgaagtc ttttacaaac cactcaatca ttaa           2334
```

<210> SEQ ID NO 16
<211> LENGTH: 777
<212> TYPE: PRT
<213> ORGANISM: Solanum habrochaites

<400> SEQUENCE: 16

Met Ile Val Gly Tyr Arg Ser Thr Ile Ile Leu Ser His Pro Lys
1               5                   10                  15

Leu Gly Asn Gly Lys Thr Ile Ser Ser Asn Ala Ile Phe Gln Arg Ser
            20                  25                  30

Cys Arg Val Arg Cys Ser His Ser Thr Thr Ser Ser Met Asn Gly Phe
        35                  40                  45

Glu Asp Ala Arg Asp Arg Ile Arg Glu Ser Phe Gly Lys Leu Glu Leu
    50                  55                  60

Ser Pro Ser Ser Tyr Asp Thr Ala Trp Val Ala Met Val Pro Ser Lys
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Thr His Pro
            100                 105                 110

Leu Leu Leu Lys Asp Ser Leu Ser Ser Thr Leu Ala Cys Leu Leu Ala

-continued

```
            115                 120                 125
Leu Thr Lys Trp Arg Val Gly Asp Glu Gln Ile Lys Arg Gly Leu Gly
    130                 135                 140
Phe Ile Glu Thr Gln Ser Trp Ala Ile Asp Asn Lys Asp Gln Ile Ser
145                 150                 155                 160
Pro Leu Gly Phe Glu Ile Ile Phe Pro Ser Met Ile Lys Ser Ala Glu
                165                 170                 175
Lys Leu Ser Leu Asn Leu Ala Ile Asn Lys Arg Asp Ser Thr Ile Lys
            180                 185                 190
Arg Ala Leu Gln Asn Glu Phe Thr Arg Asn Ile Glu Tyr Met Ser Glu
        195                 200                 205
Gly Val Gly Glu Leu Cys Asp Trp Lys Glu Ile Ile Lys Leu His Gln
    210                 215                 220
Arg Gln Asn Gly Ser Leu Phe Asp Ser Pro Ala Thr Thr Ala Ala Ala
225                 230                 235                 240
Leu Ile Tyr His Gln His Asp Lys Lys Cys Tyr Glu Tyr Leu Asn Ser
                245                 250                 255
Ile Leu Gln Gln His Lys Asn Trp Val Pro Thr Met Tyr Pro Thr Lys
            260                 265                 270
Ile His Ser Leu Leu Cys Leu Val Asp Thr Leu Gln Asn Leu Gly Val
        275                 280                 285
His Arg His Phe Lys Ser Glu Ile Lys Lys Ala Leu Asp Glu Ile Tyr
    290                 295                 300
Arg Leu Trp Gln Gln Lys Asn Glu Glu Ile Phe Ser Asn Ala Thr His
305                 310                 315                 320
Cys Ala Met Ala Phe Arg Leu Leu Arg Met Ser Tyr Tyr Asp Val Ser
                325                 330                 335
Ser Asp Glu Leu Ala Glu Phe Val Asp Glu His Phe Phe Ala Thr
            340                 345                 350
Ser Gly Lys Tyr Thr Ser His Val Glu Ile Leu Glu Leu His Lys Ala
        355                 360                 365
Ser Gln Leu Ala Ile Asp His Glu Lys Asp Asp Ile Leu Asp Lys Ile
    370                 375                 380
Asn Asn Trp Thr Arg Thr Phe Met Glu Gln Lys Leu Leu Asn Asn Gly
385                 390                 395                 400
Phe Ile Asp Arg Met Ser Lys Lys Glu Val Glu Leu Ala Leu Arg Asn
                405                 410                 415
Phe Tyr Ile Ile Ser Asp Leu Ala Glu Asn Arg Arg Tyr Ile Lys Ser
            420                 425                 430
Tyr Glu Glu Asn Asn Phe Lys Ile Leu Lys Ala Ala Tyr Arg Ser Pro
        435                 440                 445
Asn Ile Asn Asn Lys Asp Leu Phe Ile Phe Ser Ile Arg Asp Phe Glu
    450                 455                 460
Leu Cys Gln Ala Gln His Gln Glu Glu Leu Gln Gln Leu Lys Arg Trp
465                 470                 475                 480
Phe Glu Asp Cys Arg Leu Asp Gln Leu Gly Leu Ser Glu Gln Phe Ile
                485                 490                 495
Ser Ala Ser Tyr Leu Cys Ala Ile Pro Ile Val Pro Gly Pro Glu Leu
            500                 505                 510
Ser Asp Ala Arg Leu Met Tyr Ala Lys Tyr Val Ile Leu Leu Thr Ile
        515                 520                 525
Val Asp Asp His Phe Glu Ser Phe Ala Ser Thr Asp Glu Cys Leu Asn
    530                 535                 540
```

```
Ile Ile Glu Leu Val Glu Arg Trp Asp Asp Tyr Ala Ser Val Gly Tyr
545                 550                 555                 560

Lys Ser Glu Arg Val Lys Val Leu Phe Ser Met Phe Tyr Lys Ser Ile
            565                 570                 575

Glu Glu Ile Ala Thr Ile Ala Glu Ile Lys Gln Gly Arg Ser Val Lys
            580                 585                 590

Asn His Leu Ile Asn Leu Trp Leu Lys Val Met Lys Leu Met Leu Met
            595                 600                 605

Glu Arg Val Glu Trp Cys Ser Gly Lys Thr Ile Pro Arg Ile Glu Glu
        610                 615                 620

Tyr Leu Tyr Val Thr Ser Ile Thr Phe Gly Ser Arg Leu Ile Pro Leu
625                 630                 635                 640

Thr Thr Gln Tyr Phe Leu Gly Ile Lys Ile Ser Lys Asp Leu Leu Glu
                645                 650                 655

Ser Asp Glu Ile Tyr Gly Leu Cys Asn Cys Thr Gly Ile Val Leu Arg
            660                 665                 670

Leu Leu Asn Asp Leu Gln Asp Ser Lys Arg Glu Gln Lys Glu Gly Ser
        675                 680                 685

Ile Asn Leu Val Thr Leu Leu Met Lys Ser Ile Ser Glu Glu Ala
        690                 695                 700

Val Met Lys Met Lys Glu Ile Leu Glu Met Lys Arg Arg Glu Leu Phe
705                 710                 715                 720

Lys Met Val Leu Val Gln Lys Lys Gly Ser Gln Leu Pro Gln Leu Cys
                725                 730                 735

Lys Glu Ile Phe Trp Arg Thr Cys Lys Trp Ala His Phe Thr Tyr Ser
            740                 745                 750

Gln Thr Asp Arg Tyr Arg Phe Pro Glu Glu Met Glu Asn His Ile Asp
        755                 760                 765

Glu Val Phe Tyr Lys Pro Leu Asn His
770                 775

<210> SEQ ID NO 17
<211> LENGTH: 2334
<212> TYPE: DNA
<213> ORGANISM: Solanum habrochaites

<400> SEQUENCE: 17
atgatagttg gctatagaag cacaatcata atcctttctc atcctaagct aggcaatggg    60
aaaacaattt catccaatgc aattttccag agatcatgta gagtaagatg cagccacagt   120
accacttcat caatgaatgg tttcgaagat gcaagggata gaataaggga aagttttggg   180
aaattagagt tatctccttc ttcctatgac acagcatggg tagctatggt cccttcaaaa   240
cattcactaa atgagccatg ttttccacaa tgtttggatt ggattattga aaatcaaaga   300
gaagatggat cttggggact aaaccctacc catccattgc ttctcaagga ctcactttct   360
tccactcttg catgtttgct tgcactaacc aaatggagag ttggggatga gcaaatcaaa   420
agaggccttg gctttattga acccagagt tgggcaattg ataacaagga tcaaatttca   480
cctctaggat ttgaaattat atttcccagt atgatcaagt ctgcagaaaa actaagctta   540
aatctagcaa ttaacaaaag agattcaaca attaaaagag cattacagaa tgaattcacg   600
aggaatattg aatatatgag tgaaggagtt ggtgaattat gtgattggaa ggaaataata   660
aagttacatc aaaggcaaaa tggttcatta tttgattcac cagccactac tgcagctgcc   720
ttgatttacc atcagcatga taaaaaatgc tatgaatatc ttaattcaat cttgcaacaa   780
```

```
cacaaaaatt gggttcccac tatgtatcca acaaagatac attcattgct ttgcttggtt      840
gatacacttc aaaatcttgg agtacatcgg cattttaaat cagaaataaa gaaagcccta      900
gatgaaatat acaggctatg gcaacaaaag aatgaagaaa ttttctcaaa tgccacccat      960
tgtgctatgg cttttcgact tctaaggatg agctactatg atgtctcctc ggatgaacta     1020
gcagaatttg tggatgaaga acatttcttt gcaacaagtg ggaaatatac aagtcatgtt     1080
gaaattcttg aactccacaa agcatcacaa ttggctattg atcatgagaa agatgacatt     1140
ttggataaga ttaacaattg acaagaaca  tttatggagc aaaaactctt aaacaatggc     1200
ttcatagata ggatgtcaaa aaaggaggtg aacttgcttt gaggaatttt ttatatcata     1260
tctgatctag cagaaaatag aagatatata aagtcatacg aagagaacaa ttttaaaatc     1320
ttaaaagcag cttataggtc acctaacatt aacaataagg acttgtttat attttcaata     1380
cgcgactttg aattatgcca agctcaacac caagaagaac ttcaacaact caagaggtgg     1440
tttgaagatt gtagattgga ccaactcgga ctttcggaac aatttatatc tgctagttac     1500
ttatgtgcta ttcctattgt ccccgggcct gaattatccg atgctcgtct catgtacgcg     1560
aaatacgtca ttctcttgac tattgtcgat gatcatttcg agagttttgc atctacagat     1620
gaatgtctca acatcattga attagtagaa aggtgggatg actatgcaag tgtaggttat     1680
aaatctgaga gggttaaagt tttattttca atgttttaca aatcaataga ggagattgca     1740
acaattgctg aaattaaaca aggacgatct gtcaaaaatc accttattaa tttgtggctt     1800
aaagtgatga agttgatgtt gatggaacga gtagagtggt gttctggcaa gacaatacca     1860
agaatagaag agtatttgta tgttacttct ataacatttg gttcaagatt gattcctctc     1920
acaacacaat attttcttgg aataaaaata tccaaagatc ttttagaaag tgatgaaatt     1980
tatggtttat gcaattgtac cggtatagtc ttgaggctcc tcaatgattt acaagattcc     2040
aagagagaac aaaaggaggg ctcaataaat ttagtcacat tactaatgaa agtatctct      2100 gaggaagaag ctgtaatgaa gatgaaggaa atcttggaaa tgaaaagaag agagttattt     2160
aaaatggttt tagttcaaaa aaagggaagc caattgcctc aattatgcaa agaaatattt     2220
tggaggacat gcaaatgggc tcatttcact tattcacaaa ctgatagata tagatttcca     2280
gaggaaatgg agaatcacat tgatgaagtc ttttacaaac cactcaatca ttaa           2334
```

<210> SEQ ID NO 18
<211> LENGTH: 777
<212> TYPE: PRT
<213> ORGANISM: Solanum habrochaites

<400> SEQUENCE: 18

```
Met Ile Val Gly Tyr Arg Ser Thr Ile Ile Ile Leu Ser His Pro Lys
  1               5                  10                  15

Leu Gly Asn Gly Lys Thr Ile Ser Ser Asn Ala Ile Phe Gln Arg Ser
             20                  25                  30

Cys Arg Val Arg Cys Ser His Ser Thr Thr Ser Ser Met Asn Gly Phe
         35                  40                  45

Glu Asp Ala Arg Asp Arg Ile Arg Glu Ser Phe Gly Lys Leu Glu Leu
     50                  55                  60

Ser Pro Ser Ser Tyr Asp Thr Ala Trp Val Ala Met Val Pro Ser Lys
 65                  70                  75                  80

His Ser Leu Asn Glu Pro Cys Phe Pro Gln Cys Leu Asp Trp Ile Ile
                 85                  90                  95
```

```
Glu Asn Gln Arg Glu Asp Gly Ser Trp Gly Leu Asn Pro Thr His Pro
                100                 105                 110

Leu Leu Leu Lys Asp Ser Leu Ser Thr Leu Ala Cys Leu Leu Ala
        115                 120                 125

Leu Thr Lys Trp Arg Val Gly Asp Glu Gln Ile Lys Arg Gly Leu Gly
        130                 135                 140

Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
                165                 170                 175

Lys Leu Ser Leu Asn Leu Ala Ile Asn Lys Arg Asp Ser Thr Ile Lys
        180                 185                 190

Arg Ala Leu Gln Asn Glu Phe Thr Arg Asn Ile Glu Tyr Met Ser Glu
        195                 200                 205

Gly Val Gly Glu Leu Cys Asp Trp Lys Glu Ile Ile Lys Leu His Gln
        210                 215                 220

Arg Gln Asn Gly Ser Leu Phe Asp Ser Pro Ala Thr Thr Ala Ala Ala
225                 230                 235                 240

Leu Ile Tyr His Gln His Asp Lys Lys Cys Tyr Glu Tyr Leu Asn Ser
                245                 250                 255

Ile Leu Gln Gln His Lys Asn Trp Val Pro Thr Met Tyr Pro Thr Lys
        260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
        290                 295                 300

Arg Leu Trp Gln Gln Lys Asn Glu Glu Ile Phe Ser Asn Ala Thr His
305                 310                 315                 320

Cys Ala Met Ala Phe Arg Leu Leu Arg Met Ser Tyr Tyr Asp Val Ser
                325                 330                 335

Ser Asp Glu Leu Ala Glu Phe Val Asp Glu His Phe Phe Ala Thr
        340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
        370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Asn
                405                 410                 415

Phe Tyr Ile Ile Ser Asp Leu Ala Glu Asn Arg Arg Tyr Ile Lys Ser
                420                 425                 430

Tyr Glu Glu Asn Asn Phe Lys Ile Leu Lys Ala Ala Tyr Arg Ser Pro
        435                 440                 445

Asn Ile Asn Asn Lys Asp Leu Phe Ile Phe Ser Ile Arg Asp Phe Glu
        450                 455                 460

Leu Cys Gln Ala Gln His Gln Glu Leu Gln Gln Leu Lys Arg Trp
465                 470                 475                 480

Phe Glu Asp Cys Arg Leu Asp Gln Leu Gly Leu Ser Glu Gln Phe Ile
                485                 490                 495

Ser Ala Ser Tyr Leu Cys Ala Ile Pro Ile Val Pro Gly Pro Glu Leu
        500                 505                 510

Ser Asp Ala Arg Leu Met Tyr Ala Lys Tyr Val Ile Leu Leu Thr Ile
```

```
                515                 520                 525
Val Asp Asp His Phe Glu Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560

Lys Ser Glu Arg Val Lys Val Leu Phe Ser Met Phe Tyr Lys Ser Ile
                565                 570                 575

Glu Glu Ile Ala Thr Ile Ala Glu Ile Lys Gln Gly Arg Ser Val Lys
            580                 585                 590

Asn His Leu Ile Asn Leu Trp Leu Lys Val Met Lys Leu Met Leu Met
        595                 600                 605

Glu Arg Val Glu Trp Cys Ser Gly Lys Thr Ile Pro Arg Ile Glu Glu
    610                 615                 620

Tyr Leu Tyr Val Thr Ser Ile Thr Phe Gly Ser Arg Leu Ile Pro Leu
625                 630                 635                 640

Thr Thr Gln Tyr Phe Leu Gly Ile Lys Ile Ser Lys Asp Leu Leu Glu
                645                 650                 655

Ser Asp Glu Ile Tyr Gly Leu Cys Asn Cys Thr Gly Ile Val Leu Arg
            660                 665                 670

Leu Leu Asn Asp Leu Gln Asp Ser Lys Arg Glu Gln Lys Glu Gly Ser
        675                 680                 685

Ile Asn Leu Val Thr Leu Leu Met Lys Ser Ile Ser Glu Glu Ala
    690                 695                 700

Val Met Lys Met Lys Glu Ile Leu Glu Met Lys Arg Arg Glu Leu Phe
705                 710                 715                 720

Lys Met Val Leu Val Gln Lys Lys Gly Ser Gln Leu Pro Gln Leu Cys
                725                 730                 735

Lys Glu Ile Phe Trp Arg Thr Cys Lys Trp Ala His Phe Thr Tyr Ser
            740                 745                 750

Gln Thr Asp Arg Tyr Arg Phe Pro Glu Glu Met Glu Asn His Ile Asp
        755                 760                 765

Glu Val Phe Tyr Lys Pro Leu Asn His
    770                 775

<210> SEQ ID NO 19
<211> LENGTH: 2334
<212> TYPE: DNA
<213> ORGANISM: Solanum habrochaites

<400> SEQUENCE: 19
atgatagttg gctatagaag cacaatcata atcctttctc atcctaagct aggcaatggg      60
aaaacaattt catccaatgc aatttttccag agatcatgta gagtaagatg cagccacagt    120
accacttcat caatgaatgg tttcgaagat gcaagggata gaataaggga aagttttggg    180
aaattagagt tatctccttc ttcctatgac acagcatggg tagctatggt cccttcaaaa    240
cattcactaa atgagccatg ttttccacaa tgtttggatt ggattattga aaatcaaaga    300
gaagatggat cttggggact aaaccctacc catccattgc ttctcaagga ctcactttct    360
tccactcttg catgtttgct tgcactaacc aaatggagag ttggggatga gcaaatcaaa    420
agaggccttg gctttattga aacccagagt tgggcaattg ataacaagga tcaaatttca    480
cctctaggat ttgaaattat atttcccagt atgatcaagt ctgcagaaaa actaagctta    540
aatctagcaa ttaacaaaag agattcaaca attaaagag cattcagaa tgaattcacg    600 aggaatattg aatatatgag tgaaggagtt ggtgaattat gtgattggaa ggaaataata    660
```

```
aagttacatc aaaggcaaaa tggttcatta tttgattcac cagccactac tgcagctgcc      720
ttgatttacc atcagcatga caaaaaatgc tatgaatatc ttaattcaat cttgcaacaa      780
cacaaaaatt gggttcccac tatgtatcca acaaagatac attcattgct ttgcttggtt      840
gatacacttc aaaatcttgg agtacatcgg cattttaaat cagaaataaa gaaagcccta      900
gatgaaatat acaggctatg caacaaaag aatgaagaaa ttttctcaaa tgccacccat       960
tgtgctatgg cttttcgact tctaaggatg agctactatg atgtctcctc ggatgaacta     1020
gcagaatttg tggatgaaga acatttcttt gcaacaagtg ggaaatatac aagtcatgtt     1080
gaaattcttg aactccacaa agcatccaca ttggctattg atcatgagaa agatgacatt     1140
ttggataaga ttaacaattg acaagaaca tttatggagc aaaaactctt aaacaatggc      1200
ttcatagata ggatgtcaaa aaaggaggtg aacttgctt tgaggaattt ttatatcata      1260
tctgatctag cagaaaatag aagatatata aagtcatacg aagagaacaa ttttaaaatc     1320
ttaaaagcag cttataggtc acctaacatt aacaataagg acttgtttat attttcaata     1380
cgcgactttg aattatgcca agctcaacac caagaagaac ttcaacaact caagaggtgg     1440
tttgaagatt gtagattgga ccaactcgga cttttcgaac aatttatatc tgctagttac     1500
ttatgtgcta ttcctattgt ccccgggcct gaattatccg atgctcgtct catgtacgcg     1560
aaatacgtca ttctcttgac tattgtcgat gatcatttcg agagttttgc atctacagat     1620
gaatgtctca acatcattga attagtagaa aggtgggatg actatgcaag tgtaggttat     1680
aaatctgaga gggttaaagt tttattttca atgttttaca aatcaataga ggagattgca     1740
acaattgctg aaattaaaca aggacgatct gtcaaaaatc accttattaa tttgtggctt     1800
aaagtgatga agttgatgtt gatggaacga gtagagtggt gttctggcaa gacaatacca     1860
agaatagaag agtatttgta tgttacttct ataacatttg gttcaagatt gattcctctc     1920
acaacacaat atttcttgg aataaaaata tccaaagatc ttttagaaag tgatgaaatt      1980
tatggtttat gcaattgtac cggtatagtc ttgaggctcc tcaatgattt acaagattcc     2040
aagagagaac aaaaggaggg ctcaataaat ttagtcacat tactaatgaa aagtatctct     2100
gaggaagaag ctgtaatgaa gatgaaggaa atcttggaaa tgaaaagaag agagttattt     2160
aaaatggttt tagttcaaaa aaagggaagc caattgcctc aattatgcaa agaaatattt     2220
tggaggacat gcaaatgggc tcatttcact tattcacaaa ctgatagata tagatttcca     2280
gaggaaatgg agaatcacat tgatgaagtc ttttacaaac cactcaatca ttaa           2334
```

<210> SEQ ID NO 20
<211> LENGTH: 306
<212> TYPE: PRT
<213> ORGANISM: Solanum habrochaites

<400> SEQUENCE: 20

```
Glu Glu Leu Gln Gln Leu Lys Arg Trp Phe Glu Asp Tyr Arg Leu Asp
 1               5                  10                  15

Gln Leu Gly Leu Ala Glu Arg Tyr Ile His Ala Ser Tyr Leu Phe Gly
            20                  25                  30

Val Thr Val Ile Pro Glu Pro Glu Leu Ser Asp Ala Arg Leu Met Tyr
        35                  40                  45

Ala Lys Tyr Val Met Leu Leu Thr Ile Val Asp Asp His Phe Glu Ser
    50                  55                  60

Phe Ala Ser Lys Asp Glu Cys Phe Asn Ile Ile Glu Leu Val Glu Arg
65                  70                  75                  80
```

Trp Asp Asp Tyr Ala Ser Val Gly Tyr Lys Ser Glu Lys Val Lys Val
            85                  90                  95

Phe Phe Ser Val Phe Tyr Lys Ser Ile Glu Glu Leu Ala Thr Ile Ala
            100                 105                 110

Glu Ile Lys Gln Gly Arg Ser Val Lys Asn His Leu Ile Asn Leu Trp
            115                 120                 125

Leu Glu Leu Met Lys Leu Met Leu Met Glu Arg Val Glu Trp Cys Ser
130                 135                 140

Gly Lys Thr Ile Pro Ser Ile Glu Glu Tyr Leu Tyr Val Thr Ser Ile
145                 150                 155                 160

Thr Phe Cys Ala Lys Leu Ile Pro Leu Ser Thr Gln Tyr Phe Leu Gly
            165                 170                 175

Ile Lys Ile Ser Lys Asp Leu Leu Glu Ser Asp Glu Ile Cys Gly Leu
            180                 185                 190

Trp Asn Cys Ser Gly Arg Val Met Arg Ile Leu Asn Asp Leu Gln Asp
            195                 200                 205

Ser Lys Arg Glu Gln Lys Glu Val Ser Ile Asn Leu Val Thr Leu Leu
210                 215                 220

Met Lys Ser Met Ser Glu Glu Ala Ile Met Lys Ile Lys Glu Ile
225                 230                 235                 240

Leu Glu Met Asn Arg Arg Glu Leu Leu Lys Met Val Leu Val Gln Lys
            245                 250                 255

Lys Gly Ser Gln Leu Pro Gln Leu Cys Lys Asp Ile Phe Trp Arg Thr
            260                 265                 270

Ser Lys Trp Ala His Phe Thr Tyr Ser Gln Thr Asp Gly Tyr Arg Ile
            275                 280                 285

Ala Glu Glu Met Lys Asn His Ile Asp Glu Val Phe Tyr Lys Pro Leu
290                 295                 300

Asn His
305

<210> SEQ ID NO 21
<211> LENGTH: 306
<212> TYPE: PRT
<213> ORGANISM: Solanum habrochaites

<400> SEQUENCE: 21

Glu Glu Leu Gln Gln Phe Lys Arg Trp Phe Glu Asp Tyr Arg Leu Asp
 1               5                  10                  15

Gln Leu Gly Ile Ala Glu Arg Tyr Ile His Asp Thr Tyr Leu Cys Ala
            20                  25                  30

Val Ile Val Pro Glu Pro Glu Leu Ser Asp Ala Arg Leu Leu Tyr
            35                  40                  45

Ala Lys Tyr Val Leu Leu Leu Thr Ile Val Asp Asp Gln Phe Asp Ser
50                  55                  60

Phe Ala Ser Thr Asp Glu Cys Leu Asn Ile Ile Glu Leu Val Glu Arg
65                  70                  75                  80

Trp Asp Asp Tyr Ala Ser Val Gly Tyr Lys Ser Glu Lys Val Lys Val
            85                  90                  95

Phe Phe Ser Thr Leu Tyr Lys Ser Ile Glu Glu Leu Val Thr Ile Ala
            100                 105                 110

Glu Ile Lys Gln Gly Arg Ser Val Lys Asn His Leu Leu Asn Leu Trp
            115                 120                 125

Leu Glu Leu Val Lys Leu Met Leu Met Glu Arg Val Glu Trp Phe Ser

Gly Lys Thr Ile Pro Ser Ile Glu Glu Tyr Leu Tyr Val Thr Ser Ile
145                 150                 155                 160

Thr Phe Gly Ala Arg Leu Ile Pro Leu Thr Thr Gln Tyr Phe Leu Gly
                165                 170                 175

Ile Lys Ile Ser Glu Asp Ile Leu Glu Ser Asp Glu Ile Tyr Gly Leu
            180                 185                 190

Cys Asn Cys Thr Gly Arg Val Leu Arg Ile Leu Asn Asp Leu Gln Asp
                195                 200                 205

Ser Lys Lys Glu Gln Lys Glu Asp Ser Val Thr Ile Val Thr Leu Leu
            210                 215                 220

Met Lys Ser Met Ser Glu Glu Ala Ile Met Lys Ile Lys Glu Ile
225                 230                 235                 240

Leu Glu Met Asn Arg Arg Glu Leu Leu Lys Met Val Leu Val Gln Lys
                245                 250                 255

Lys Gly Ser Gln Leu Pro Gln Ile Cys Lys Asp Ile Phe Trp Arg Thr
                260                 265                 270

Ser Asn Trp Ala Asp Phe Ile Tyr Leu Gln Thr Asp Gly Tyr Arg Ile
            275                 280                 285

Ala Glu Glu Met Lys Asn His Ile Asp Glu Val Phe Tyr Lys Pro Leu
290                 295                 300

Asn His
305

<210> SEQ ID NO 22
<211> LENGTH: 306
<212> TYPE: PRT
<213> ORGANISM: Solanum habrochaites

<400> SEQUENCE: 22

Glu Glu Leu Gln Gln Leu Lys Arg Trp Phe Glu Asp Cys Arg Leu Asp
1               5                   10                  15

Gln Leu Gly Leu Ser Glu Gln Phe Ile Ser Ala Ser Tyr Leu Cys Ala
                20                  25                  30

Ile Pro Ile Val Pro Gly Pro Glu Leu Ser Asp Ala Arg Leu Val Tyr
            35                  40                  45

Ala Lys Tyr Val Met Leu Leu Thr Ile Val Asp Asp His Phe Glu Ser
50                  55                  60

Phe Ala Ser Thr Asp Glu Cys Leu Asn Ile Ile Glu Leu Val Glu Arg
65                  70                  75                  80

Trp Asp Asp Tyr Ala Ser Val Gly Tyr Lys Ser Glu Arg Val Lys Val
                85                  90                  95

Leu Phe Ser Met Phe Tyr Lys Ser Ile Glu Glu Ile Ala Thr Ile Ala
                100                 105                 110

Glu Ile Lys Gln Gly Arg Ser Val Lys Asn His Leu Ile Asn Leu Trp
            115                 120                 125

Leu Lys Val Met Lys Leu Met Leu Met Glu Arg Val Glu Trp Cys Ser
130                 135                 140

Gly Lys Thr Ile Pro Arg Ile Glu Glu Tyr Leu Tyr Val Ser Ser Ile
145                 150                 155                 160

Thr Phe Gly Ser Arg Leu Ile Pro Leu Thr Thr Gln Tyr Phe Ile Gly
                165                 170                 175

Ile Lys Ile Ser Lys Asp Leu Leu Glu Ser Asp Glu Ile Tyr Gly Leu
            180                 185                 190

-continued

```
Cys Asn Phe Thr Gly Ile Val Leu Arg Leu Leu Asn Asp Leu Gln Asp
    195                 200                 205

Ser Lys Arg Glu Gln Lys Glu Gly Ser Ile Asn Leu Val Thr Leu Leu
    210                 215                 220

Met Lys Ser Ile Ser Glu Glu Ala Ile Met Lys Met Lys Glu Ile
225                 230                 235                 240

Leu Glu Met Lys Arg Arg Glu Leu Phe Lys Met Val Leu Val Gln Lys
                245                 250                 255

Lys Gly Ser Gln Leu Pro Gln Leu Cys Lys Glu Ile Phe Trp Arg Thr
            260                 265                 270

Cys Lys Trp Ala His Phe Thr Tyr Ser Gln Thr Asp Arg Tyr Arg Phe
        275                 280                 285

Pro Glu Glu Met Glu Asn His Ile Asp Glu Val Phe Tyr Lys Pro Leu
    290                 295                 300

Asn His
305
```